(12) United States Patent
Perrow et al.

(10) Patent No.: US 10,159,514 B2
(45) Date of Patent: Dec. 25, 2018

(54) METHOD OF IMPLANTING A BONE PLATE

(71) Applicant: Pioneer Surgical Technology, Inc., Marquette, MI (US)

(72) Inventors: Scott J. Perrow, Ishpeming, MI (US); Reuben J. Robie, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 143 days.

(21) Appl. No.: 14/954,179

(22) Filed: Nov. 30, 2015

(65) Prior Publication Data

US 2016/0081723 A1  Mar. 24, 2016

Related U.S. Application Data

(63) Continuation of application No. 13/725,420, filed on Dec. 21, 2012, now Pat. No. 9,198,769.
(Continued)

(51) Int. Cl.
*A61B 17/80* (2006.01)
*A61B 17/70* (2006.01)
(Continued)

(52) U.S. Cl.
CPC ........ *A61B 17/7059* (2013.01); *A61B 17/808* (2013.01); *A61B 17/8014* (2013.01);
(Continued)

(58) Field of Classification Search
None
See application file for complete search history.

(56) References Cited

U.S. PATENT DOCUMENTS 3,413,741 A  12/1968 Fagan et al.
3,695,259 A  10/1972 Yost
(Continued)

FOREIGN PATENT DOCUMENTS

CA  2395609  2/2001
CA  2482403  9/2003
(Continued)

OTHER PUBLICATIONS

Depuy Spine, Inc., Charite Artificial Disc Centreline TDR Instrumentation Surgical Technique, Dec. 2004, 20 pp.
(Continued)

*Primary Examiner* — Samuel Hanna
(74) *Attorney, Agent, or Firm* — Fitch, Even, Tabin & Flannery LLP

(57) ABSTRACT

In one aspect, a bone anchor assembly is provided having a bone anchor with a head, a resilient locking cap extending about a portion of the bone anchor head, and a cap drive member having a depending annular wall. The annular wall and locking cap have engagement surfaces configured to engage and expand the locking cap as the cap drive member is shifted from an unlocked to a locked position. In another form, a bone plate system is provided including a bone plate having an elongated throughbore and a resilient support member received therein. The support member has an opening sized to receive a bone anchor head and an actuator device carried thereon. The bone plate and support member have interfering portions configured to be shifted to a locked orientation to lock the support member and the bone anchor head at an axial position in the throughbore.

21 Claims, 50 Drawing Sheets

Related U.S. Application Data

(60) Provisional application No. 61/580,055, filed on Dec. 23, 2011.

(51) Int. Cl.
*A61B 17/86* (2006.01)
*A61F 2/44* (2006.01)
*A61B 17/88* (2006.01)

(52) U.S. Cl.
CPC ...... *A61B 17/8038* (2013.01); *A61B 17/8042* (2013.01); *A61B 17/8047* (2013.01); *A61B 17/861* (2013.01); *A61B 17/8888* (2013.01); *A61F 2/442* (2013.01)

(56) References Cited

U.S. PATENT DOCUMENTS

| | | |
|---|---|---|
| 3,800,433 A | 4/1974 | Kubodera |
| 3,844,291 A | 10/1974 | Moen |
| 3,867,728 A | 2/1975 | Stubstad et al. |
| 3,875,595 A | 4/1975 | Froning et al. |
| 3,975,778 A | 8/1976 | Newton, III |
| 4,021,382 A | 5/1977 | Stoy |
| 4,081,402 A | 3/1978 | Levy |
| 4,147,764 A | 4/1979 | Levy |
| 4,309,777 A | 1/1982 | Patil |
| 4,349,921 A | 9/1982 | Kuntz |
| 4,388,921 A | 6/1983 | Sutter |
| 4,454,612 A | 6/1984 | McDaniel |
| 4,484,570 A | 11/1984 | Sutter |
| 4,650,490 A | 3/1987 | Figgie, III |
| 4,714,469 A | 12/1987 | Kenna |
| 4,728,561 A | 3/1988 | Crocker |
| 4,759,766 A | 7/1988 | Buettner-Janz |
| 4,759,769 A | 7/1988 | Hedman |
| 4,863,476 A | 9/1989 | Shepperd |
| 4,863,477 A | 9/1989 | Monson |
| 4,917,704 A | 4/1990 | Frey |
| 4,932,969 A | 6/1990 | Frey |
| 4,936,848 A | 6/1990 | Bagby |
| 4,946,378 A | 8/1990 | Hirayama |
| 4,997,432 A | 3/1991 | Keller |
| 5,002,576 A | 3/1991 | Fuhrmann |
| 5,020,519 A | 6/1991 | Hayes |
| 5,035,716 A | 7/1991 | Downey |
| 5,047,055 A | 9/1991 | Bao |
| 5,053,036 A | 10/1991 | Perren |
| 5,057,111 A | 10/1991 | Park |
| 5,071,437 A | 12/1991 | Steffee |
| 5,092,866 A | 3/1992 | Breard |
| 5,108,438 A | 4/1992 | Stone |
| 5,127,920 A | 7/1992 | MacArthur |
| 5,133,759 A | 7/1992 | Turner |
| 5,133,772 A | 7/1992 | Hack |
| 5,147,404 A | 9/1992 | Downey |
| 5,171,279 A | 12/1992 | Mathews |
| 5,171,281 A | 12/1992 | Parsons |
| 5,176,710 A | 1/1993 | Hahn |
| 5,192,326 A | 3/1993 | Bao |
| 5,242,443 A | 9/1993 | Kambin |
| 5,258,005 A | 11/1993 | Christian |
| 5,258,031 A | 11/1993 | Salib |
| 5,258,043 A | 11/1993 | Stone |
| 5,273,742 A | 12/1993 | Gould |
| 5,306,308 A | 4/1994 | Gross |
| 5,306,309 A | 4/1994 | Wagner |
| 5,314,477 A | 5/1994 | Marnay |
| 5,320,625 A | 6/1994 | Bertin |
| 5,320,644 A | 6/1994 | Baumgartner |
| 5,401,269 A | 3/1995 | Buttner-Janz |
| 5,423,826 A | 6/1995 | Coates |
| 5,425,773 A | 6/1995 | Boyd |
| 5,443,512 A | 8/1995 | Parr |
| 5,458,642 A | 10/1995 | Beer |
| 5,458,643 A | 10/1995 | Oka |
| 5,462,362 A | 10/1995 | Yuhta |
| 5,480,440 A | 1/1996 | Kambin |
| 5,480,449 A | 1/1996 | Hamilton |
| 5,507,772 A | 4/1996 | Shutt |
| 5,507,816 A | 4/1996 | Bullivant |
| 5,514,180 A | 5/1996 | Heggeness |
| 5,520,690 A | 5/1996 | Errico |
| 5,522,899 A | 6/1996 | Michelson |
| 5,531,746 A | 7/1996 | Errico |
| 5,534,028 A | 7/1996 | Bao |
| 5,549,612 A | 8/1996 | Yapp |
| 5,549,679 A | 8/1996 | Kuslich |
| 5,556,431 A | 9/1996 | Buttner-Janz |
| 5,556,433 A | 9/1996 | Gabriel |
| 5,562,736 A | 10/1996 | Ray |
| 5,562,738 A | 10/1996 | Boyd |
| 5,571,189 A | 11/1996 | Kuslich |
| 5,578,034 A | 11/1996 | Estes |
| 5,584,887 A | 12/1996 | Kambin |
| 5,595,563 A | 1/1997 | Moisdon |
| 5,601,553 A | 2/1997 | Trebing |
| 5,607,426 A | 3/1997 | Ralph |
| 5,609,643 A | 3/1997 | Colleran |
| 5,645,596 A | 7/1997 | Kim |
| 5,645,597 A | 7/1997 | Krapiva |
| 5,658,336 A | 8/1997 | Pisharodi |
| 5,665,122 A | 9/1997 | Kambin |
| 5,674,295 A | 10/1997 | Ray |
| 5,674,296 A | 10/1997 | Bryan |
| 5,676,701 A | 10/1997 | Yuan |
| 5,676,702 A | 10/1997 | Ratron |
| 5,681,311 A | 10/1997 | Foley |
| 5,683,392 A | 11/1997 | Richelsoph |
| 5,683,465 A | 11/1997 | Shinn |
| 5,693,100 A | 12/1997 | Pisharodi |
| 5,702,450 A | 12/1997 | Bisserie |
| 5,713,900 A | 2/1998 | Benzel |
| 5,716,416 A | 2/1998 | Lin |
| 5,720,751 A | 2/1998 | Jackson |
| 5,728,762 A | 3/1998 | Reich |
| 5,733,287 A | 3/1998 | Tepic |
| 5,735,853 A | 3/1998 | Olerud |
| 5,755,797 A | 5/1998 | Baumgartner |
| 5,755,798 A | 5/1998 | Papavero |
| 5,782,832 A | 7/1998 | Larsen |
| 5,782,833 A | 7/1998 | Haider |
| 5,797,912 A | 8/1998 | Runciman |
| 5,800,433 A | 9/1998 | Benzel |
| 5,824,093 A | 10/1998 | Ray |
| 5,824,094 A | 10/1998 | Serhan |
| 5,843,082 A | 12/1998 | Yuan |
| 5,860,980 A | 1/1999 | Axelson, Jr. |
| 5,863,293 A | 1/1999 | Richelsoph |
| 5,865,845 A | 2/1999 | Thalgott |
| 5,865,846 A | 2/1999 | Bryan |
| 5,888,223 A | 3/1999 | Bray, Jr. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima |
| 5,904,683 A | 5/1999 | Pohndorf |
| 5,919,235 A | 7/1999 | Husson |
| 5,941,885 A | 8/1999 | Jackson |
| 5,954,635 A | 9/1999 | Foley |
| 5,954,722 A | 9/1999 | Bono |
| 5,964,760 A | 10/1999 | Richelsoph |
| 5,964,761 A | 10/1999 | Kambin |
| 5,964,807 A | 10/1999 | Gan |
| 5,969,020 A | 10/1999 | Shalaby |
| 5,976,186 A | 11/1999 | Bao |
| 5,980,572 A | 11/1999 | Kim |
| 6,001,130 A | 12/1999 | Bryan |
| 6,010,503 A | 1/2000 | Richelsoph |
| 6,019,793 A | 2/2000 | Perren |
| 6,022,350 A | 2/2000 | Ganem |
| 6,022,376 A | 2/2000 | Assell |
| 6,030,389 A | 2/2000 | Wagner |
| 6,036,693 A | 3/2000 | Yuan |

(56) References Cited

U.S. PATENT DOCUMENTS

| | | | |
|---|---|---|---|
| 6,039,763 A | 3/2000 | Shelokov |
| RE36,758 E | 6/2000 | Fitz |
| 6,074,390 A | 6/2000 | Zucherman |
| 6,090,111 A | 7/2000 | Nichols |
| 6,093,205 A | 7/2000 | McLeod |
| 6,093,207 A | 7/2000 | Pisharodi |
| 6,096,044 A | 8/2000 | Boyd |
| 6,110,210 A | 8/2000 | Norton |
| 6,113,639 A | 9/2000 | Ray |
| 6,117,173 A | 9/2000 | Taddia |
| 6,127,597 A | 10/2000 | Beyar |
| 6,132,432 A | 10/2000 | Richelsoph |
| 6,132,465 A | 10/2000 | Ray |
| 6,136,031 A | 10/2000 | Middleton |
| 6,139,550 A | 10/2000 | Michelson |
| 6,139,579 A | 10/2000 | Steffee |
| 6,139,721 A | 10/2000 | Baldiraghi |
| 6,143,031 A | 11/2000 | Knothe |
| 6,146,422 A | 11/2000 | Lawson |
| 6,152,927 A | 11/2000 | Farris |
| 6,156,067 A | 12/2000 | Bryan |
| 6,162,252 A | 12/2000 | Kuras |
| 6,174,311 B1 | 1/2001 | Branch |
| 6,179,874 B1 | 1/2001 | Cauthen |
| 6,183,518 B1 | 2/2001 | Ross |
| 6,187,048 B1 | 2/2001 | Milner |
| 6,190,387 B1 | 2/2001 | Zucherman |
| 6,193,720 B1 | 2/2001 | Yuan |
| 6,193,721 B1 | 2/2001 | Michelson |
| 6,206,924 B1 | 3/2001 | Timm |
| 6,214,005 B1 | 4/2001 | Benzel |
| 6,224,630 B1 | 5/2001 | Bao |
| 6,226,548 B1 | 5/2001 | Foley |
| 6,228,085 B1 | 5/2001 | Theken |
| 6,235,033 B1 * | 5/2001 | Brace .............. A61B 17/8038 606/288 |
| 6,240,926 B1 | 6/2001 | ChinGan |
| 6,241,731 B1 | 6/2001 | Fiz |
| 6,251,140 B1 | 6/2001 | Marino |
| 6,258,089 B1 | 7/2001 | Campbell |
| 6,261,291 B1 | 7/2001 | Talaber |
| 6,264,695 B1 | 7/2001 | Stoy |
| 6,280,475 B1 | 8/2001 | Bao |
| 6,283,968 B1 | 9/2001 | Mehdizadeh |
| 6,283,998 B1 | 9/2001 | Eaton |
| 6,287,309 B1 * | 9/2001 | Baccelli ............. A61B 17/7007 606/292 |
| 6,287,313 B1 | 9/2001 | Sasso |
| 6,290,703 B1 | 9/2001 | Ganem |
| 6,306,136 B1 | 10/2001 | Baccelli |
| 6,309,393 B1 | 10/2001 | Tepic |
| 6,315,795 B1 | 11/2001 | Scarborough |
| 6,315,797 B1 | 11/2001 | Middleton |
| 6,331,179 B1 | 12/2001 | Freid |
| 6,342,055 B1 | 1/2002 | Eisermann |
| 6,348,071 B1 | 2/2002 | Steffee |
| 6,352,557 B1 | 3/2002 | Ferree |
| 6,355,040 B1 | 3/2002 | Richelsoph |
| 6,368,350 B1 | 4/2002 | Erickson |
| 6,371,990 B1 | 4/2002 | Ferree |
| 6,375,682 B1 | 4/2002 | Fleischmann |
| 6,383,186 B1 | 5/2002 | Michelson |
| 6,395,032 B1 | 5/2002 | Gauchet |
| 6,398,783 B1 | 6/2002 | Michelson |
| 6,402,784 B1 | 6/2002 | Wardlaw |
| 6,402,785 B1 | 6/2002 | Zdeblick |
| 6,413,259 B1 | 7/2002 | Lyons |
| 6,416,528 B1 | 7/2002 | Michelson |
| 6,419,704 B1 | 7/2002 | Ferree |
| 6,428,542 B1 | 8/2002 | Michelson |
| 6,428,544 B1 | 8/2002 | Ralph |
| 6,428,575 B2 | 8/2002 | Koo |
| 6,428,579 B1 | 8/2002 | Valentini |
| 6,432,106 B1 | 8/2002 | Fraser |
| 6,432,107 B1 | 8/2002 | Ferree |
| 6,432,140 B1 | 8/2002 | Lin |
| 6,436,098 B1 | 8/2002 | Michelson |
| 6,436,101 B1 | 8/2002 | Hamada |
| 6,436,102 B1 | 8/2002 | Ralph |
| 6,436,140 B1 | 8/2002 | Liu |
| 6,436,141 B2 | 8/2002 | Castro |
| 6,436,142 B1 | 8/2002 | Paes |
| 6,436,146 B1 | 8/2002 | Hassler |
| 6,440,133 B1 | 8/2002 | Beale |
| 6,440,168 B1 | 8/2002 | Cauthen |
| 6,440,170 B1 | 8/2002 | Jackson |
| 6,454,769 B2 | 9/2002 | Wagner |
| 6,454,771 B1 | 9/2002 | Michelson |
| 6,458,133 B1 | 10/2002 | Lin |
| 6,478,822 B1 | 11/2002 | Leroux |
| 6,485,491 B1 | 11/2002 | Farris |
| 6,485,591 B1 | 11/2002 | Nakao |
| 6,488,716 B1 | 12/2002 | Huang |
| 6,503,250 B2 | 1/2003 | Paul |
| 6,508,839 B1 | 1/2003 | Lambrecht |
| 6,517,580 B1 | 2/2003 | Ramadan |
| 6,527,776 B1 | 3/2003 | Michelson |
| 6,527,804 B1 | 3/2003 | Gauchet |
| 6,530,929 B1 | 3/2003 | Justis |
| 6,533,786 B1 | 3/2003 | Needham |
| 6,540,785 B1 | 4/2003 | Gill |
| 6,547,823 B2 | 4/2003 | Scarborough |
| 6,562,047 B2 | 5/2003 | Ralph |
| 6,565,565 B1 | 5/2003 | Yuan |
| 6,575,975 B2 | 6/2003 | Brace |
| 6,579,290 B1 | 6/2003 | Hardcastle |
| 6,579,320 B1 | 6/2003 | Gauchet |
| 6,579,321 B1 | 6/2003 | Gordon |
| 6,582,466 B1 | 6/2003 | Gauchet |
| 6,592,586 B1 | 7/2003 | Michelson |
| 6,592,624 B1 | 7/2003 | Fraser |
| 6,595,993 B2 | 7/2003 | Donno |
| 6,599,290 B2 | 7/2003 | Bailey |
| 6,602,255 B1 | 8/2003 | Campbell |
| 6,602,291 B1 | 8/2003 | Ray |
| 6,610,091 B1 | 8/2003 | Reiley |
| 6,613,053 B1 | 9/2003 | Collins |
| 6,616,666 B1 | 9/2003 | Michelson |
| 6,620,163 B1 | 9/2003 | Michelson |
| 6,626,907 B2 | 9/2003 | Campbell |
| 6,648,888 B1 | 11/2003 | Shluzas |
| 6,660,006 B2 | 12/2003 | Markworth |
| 6,663,635 B2 | 12/2003 | Frigg |
| 6,666,866 B2 | 12/2003 | Martz |
| 6,669,697 B1 | 12/2003 | Pisharodi |
| 6,669,700 B1 | 12/2003 | Farris |
| 6,679,883 B2 | 1/2004 | Hawkes |
| 6,679,915 B1 | 1/2004 | Cauthen |
| 6,682,562 B2 | 1/2004 | Viart |
| 6,695,846 B2 | 2/2004 | Richelsoph |
| 6,740,088 B1 | 5/2004 | Kozak |
| 6,743,257 B2 | 6/2004 | Castro |
| 6,749,614 B2 | 6/2004 | Teitelbaum |
| 6,755,829 B1 | 6/2004 | Bono |
| 6,755,833 B1 | 6/2004 | Paul |
| 6,770,095 B2 | 8/2004 | Grinberg |
| 6,783,550 B2 | 8/2004 | MacArthur |
| 6,793,656 B1 | 9/2004 | Mathews |
| 6,793,658 B2 | 9/2004 | LeHuec |
| 6,793,678 B2 | 9/2004 | Hawkins |
| 6,875,212 B2 | 4/2005 | Shaolian |
| 6,884,242 B2 | 4/2005 | LeHuec |
| 6,890,334 B2 | 5/2005 | Brace |
| 6,890,335 B2 | 5/2005 | Grabowski |
| 6,899,716 B2 | 5/2005 | Cragg |
| 6,916,320 B2 | 7/2005 | Michelson |
| 6,936,050 B2 | 8/2005 | Michelson |
| 6,936,051 B2 | 8/2005 | Michelson |
| 6,936,071 B1 | 8/2005 | Marnay |
| 6,951,538 B2 | 10/2005 | Ritland |
| 6,964,664 B2 | 11/2005 | Freid |
| 6,964,667 B2 | 11/2005 | Shaolian |
| 6,969,390 B2 | 11/2005 | Michelson |
| 7,001,387 B2 | 2/2006 | Farris |

(56) References Cited

U.S. PATENT DOCUMENTS

| | | |
|---|---|---|
| 7,001,389 B1 | 2/2006 | Navarro |
| 7,001,433 B2 | 2/2006 | Songer |
| 7,011,660 B2 | 3/2006 | Sherman |
| 7,048,739 B2 | 5/2006 | Konieczynski |
| 7,052,499 B2 | 5/2006 | Steger |
| 7,060,069 B2 | 6/2006 | Kozak |
| 7,063,701 B2 | 6/2006 | Michelson |
| 7,063,702 B2 | 6/2006 | Michelson |
| 7,074,221 B2 | 7/2006 | Michelson |
| 7,077,844 B2 | 7/2006 | Michelson |
| 7,081,117 B2 | 7/2006 | Bono |
| 7,083,621 B2 | 8/2006 | Shaolian |
| 7,090,674 B2 | 8/2006 | Doubler |
| 7,090,676 B2 | 8/2006 | Huebner |
| 7,125,426 B2 | 10/2006 | Moumene |
| 7,137,984 B2 | 11/2006 | Michelson |
| 7,141,051 B2 | 11/2006 | Janowski |
| 7,156,876 B2 | 1/2007 | Moumene |
| 7,175,624 B2 | 2/2007 | Konieczynski |
| 7,204,837 B2 | 4/2007 | Paul |
| 7,229,443 B2 | 6/2007 | Eberlein |
| 7,264,621 B2 | 9/2007 | Coates |
| 7,273,481 B2 | 9/2007 | Lombardo |
| 7,309,340 B2 | 12/2007 | Fallin |
| 7,476,239 B2 | 1/2009 | Jackson |
| 7,476,240 B2 | 1/2009 | Raymond |
| 7,618,418 B2 | 11/2009 | Malandain |
| 7,625,381 B2 | 12/2009 | Michelson |
| 7,641,676 B2 | 1/2010 | Mathieu |
| 7,648,520 B2 | 1/2010 | Markworth |
| 7,651,517 B2 | 1/2010 | Konieczynski |
| 7,699,880 B2 | 4/2010 | Orbay |
| 7,758,616 B2 | 7/2010 | LeHuec |
| 7,766,947 B2 | 8/2010 | Hawkes |
| 7,789,899 B2 | 9/2010 | Markworth |
| 7,794,482 B2 | 9/2010 | Mathieu |
| 7,846,190 B2 | 12/2010 | Ball |
| 7,857,839 B2 | 12/2010 | Duong |
| 7,909,859 B2 | 3/2011 | Mosca |
| 7,914,561 B2 | 3/2011 | Konieczynski |
| 7,918,878 B2 | 4/2011 | Songer |
| 7,922,727 B2 | 4/2011 | Songer |
| 7,931,678 B2 | 4/2011 | Konieczynski |
| 7,931,681 B2 | 4/2011 | Carls |
| 7,935,137 B2 | 5/2011 | Gorhan |
| 7,976,550 B2 | 7/2011 | Trudeau |
| 7,981,142 B2 | 7/2011 | Konieczynski |
| 8,007,523 B2 | 8/2011 | Wagner |
| 8,012,156 B2 | 9/2011 | MarquezAlvarez |
| 8,034,089 B2 | 10/2011 | Matthis |
| 8,075,602 B2 | 12/2011 | Lombardo |
| 8,100,955 B2 | 1/2012 | Blain |
| 8,114,160 B2 | 2/2012 | Janowski |
| 8,118,872 B2 | 2/2012 | Trudeau |
| 8,142,485 B2 | 3/2012 | Buhren |
| 8,152,838 B2 | 4/2012 | Ensign |
| 8,163,019 B2 | 4/2012 | Bao |
| 8,172,885 B2 | 5/2012 | Songer |
| 8,192,439 B2 | 6/2012 | Songer |
| 8,231,676 B2 | 7/2012 | Trudeau |
| 8,241,360 B2 | 8/2012 | Bao |
| 8,246,655 B2 | 8/2012 | Jackson |
| 8,257,396 B2 | 9/2012 | Jackson |
| 8,262,570 B2 | 9/2012 | White |
| 8,262,731 B2 | 9/2012 | Songer |
| 8,287,575 B2 | 10/2012 | Murner |
| 8,308,774 B2 | 11/2012 | Hoffman |
| 8,313,515 B2 | 11/2012 | Brennan |
| 8,343,165 B2 | 1/2013 | Berrevoets |
| 8,372,084 B2 | 2/2013 | Pernsteiner |
| 8,388,684 B2 | 3/2013 | Bao |
| 8,409,213 B2 | 4/2013 | Trudeau |
| 8,414,616 B2 | 4/2013 | Berrevoets |
| 8,425,529 B2 | 4/2013 | Milz et al. |
| 8,470,040 B2 | 6/2013 | Kovarik |
| 8,480,716 B2 | 7/2013 | Perrow |
| 8,512,344 B2 | 8/2013 | Hoffman |
| 8,551,141 B2 | 10/2013 | Gephart |
| 8,597,357 B2 | 12/2013 | Trudeau |
| 8,603,141 B2 | 12/2013 | Hochschuler |
| 8,623,019 B2 | 1/2014 | Perrow |
| 8,641,719 B2 | 2/2014 | Gephart |
| 8,702,600 B2 | 4/2014 | Perrow |
| 8,715,350 B2 | 5/2014 | Janowski |
| 8,808,382 B2 | 8/2014 | Bao |
| 9,033,988 B2 | 5/2015 | Gephart et al. |
| 9,072,609 B2 | 7/2015 | Kovarik |
| 9,089,437 B2 | 7/2015 | Ahn |
| 9,101,493 B2 | 8/2015 | Trudeau |
| 9,113,852 B2 | 8/2015 | Perrow |
| 9,113,972 B2 | 8/2015 | Trudeau |
| 9,132,021 B2 | 9/2015 | Mermuys |
| 9,198,769 B2 | 12/2015 | Perrow |
| 9,216,098 B2 | 12/2015 | Trudeau |
| 9,220,606 B2 | 12/2015 | Janowski |
| 9,233,011 B2 | 1/2016 | Trudeau |
| 9,241,807 B2 | 1/2016 | Mohar |
| 9,492,211 B2 | 11/2016 | Perrow |
| 2001/0010021 A1 | 7/2001 | Boyd |
| 2001/0012938 A1 | 8/2001 | Zucherman |
| 2001/0016772 A1 | 8/2001 | Lee |
| 2001/0016773 A1 | 8/2001 | Serhan |
| 2001/0016776 A1 | 8/2001 | Zuckerman |
| 2001/0020476 A1 | 9/2001 | Gan |
| 2001/0021851 A1 | 9/2001 | Eberlein |
| 2001/0027343 A1 | 10/2001 | Keller |
| 2001/0032019 A1 | 10/2001 | VanDyke |
| 2001/0032020 A1 | 10/2001 | Besselink |
| 2001/0037112 A1 | 11/2001 | Brace |
| 2001/0047208 A1 | 11/2001 | Michelson |
| 2001/0051829 A1 | 12/2001 | Middleton |
| 2002/0013600 A1 | 1/2002 | Scribner |
| 2002/0016595 A1 | 2/2002 | Michelson |
| 2002/0022843 A1 | 2/2002 | Michelson |
| 2002/0022883 A1 | 2/2002 | Burg |
| 2002/0022888 A1 | 2/2002 | Serhan |
| 2002/0026197 A1* | 2/2002 | Foley .................. A61B 17/025 606/105 |
| 2002/0026244 A1 | 2/2002 | Trieu |
| 2002/0029082 A1 | 3/2002 | Muhanna |
| 2002/0029083 A1 | 3/2002 | Zuckerman |
| 2002/0035400 A1 | 3/2002 | Bryan |
| 2002/0045942 A1 | 4/2002 | Ham |
| 2002/0045944 A1 | 4/2002 | Muhanna |
| 2002/0049498 A1 | 4/2002 | Yuksel |
| 2002/0058939 A1 | 5/2002 | Wagner |
| 2002/0072766 A1* | 6/2002 | Hunt ...................... A61B 17/29 606/205 |
| 2002/0082608 A1 | 6/2002 | Reiley |
| 2002/0082701 A1 | 6/2002 | Zdeblick |
| 2002/0087480 A1 | 7/2002 | Sauriol |
| 2002/0099444 A1 | 7/2002 | Boyd |
| 2002/0106393 A1 | 8/2002 | Bianchi |
| 2002/0107571 A1 | 8/2002 | Foley |
| 2002/0107572 A1 | 8/2002 | Foley |
| 2002/0107573 A1 | 8/2002 | Steinberg |
| 2002/0120269 A1 | 8/2002 | Lange |
| 2002/0120270 A1 | 8/2002 | Trieu |
| 2002/0120272 A1 | 8/2002 | Yuan |
| 2002/0120273 A1 | 8/2002 | Needham |
| 2002/0120334 A1 | 8/2002 | Crozet |
| 2002/0120336 A1 | 8/2002 | Santilli |
| 2002/0128655 A1 | 9/2002 | Michelson |
| 2002/0156474 A1 | 10/2002 | Wack |
| 2002/0156528 A1 | 10/2002 | Gau |
| 2002/0161368 A1 | 10/2002 | Foley |
| 2002/0165612 A1 | 11/2002 | Gerber |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0004519 A1 | 1/2003 | Torode |
| 2003/0009226 A1 | 1/2003 | Graf |
| 2003/0023311 A1 | 1/2003 | Trieu |

(56) References Cited

U.S. PATENT DOCUMENTS

| | | |
|---|---|---|
| 2003/0028197 A1 | 2/2003 | Hanson |
| 2003/0028251 A1 | 2/2003 | Mathews |
| 2003/0040799 A1 | 2/2003 | Boyd |
| 2003/0045939 A1 | 3/2003 | Casutt |
| 2003/0055427 A1 | 3/2003 | Graf |
| 2003/0060826 A1 | 3/2003 | Foley |
| 2003/0060828 A1 | 3/2003 | Michelson |
| 2003/0073998 A1 | 4/2003 | Pagliuca |
| 2003/0074076 A1 | 4/2003 | Ferree |
| 2003/0078583 A1 | 4/2003 | Biedermann |
| 2003/0100951 A1 | 5/2003 | Serhan |
| 2003/0125742 A1 | 7/2003 | Yuan |
| 2003/0135276 A1 | 7/2003 | Eckman |
| 2003/0135277 A1 | 7/2003 | Bryan |
| 2003/0135278 A1 | 7/2003 | Eckman |
| 2003/0149434 A1 | 8/2003 | Paul |
| 2003/0176921 A1 | 9/2003 | Lawson |
| 2003/0187440 A1 | 10/2003 | Richelsoph |
| 2003/0199876 A1 | 10/2003 | Brace |
| 2003/0204260 A1 | 10/2003 | Ferree |
| 2003/0204261 A1 | 10/2003 | Eisermann |
| 2003/0208203 A1* | 11/2003 | Lim .................. A61B 17/7083 606/86 A |
| 2003/0208204 A1 | 11/2003 | Bailey |
| 2003/0220691 A1 | 11/2003 | Songer |
| 2003/0225408 A1 | 12/2003 | Nichols |
| 2003/0225409 A1 | 12/2003 | Freid |
| 2003/0229347 A1 | 12/2003 | Sherman |
| 2003/0236447 A1 | 12/2003 | Ritland |
| 2004/0019356 A1 | 1/2004 | Fraser |
| 2004/0024462 A1 | 2/2004 | Ferree |
| 2004/0030391 A1 | 2/2004 | Ferree |
| 2004/0039384 A1 | 2/2004 | Boehm |
| 2004/0044410 A1 | 3/2004 | Ferree |
| 2004/0059333 A1 | 3/2004 | Carl |
| 2004/0073315 A1 | 4/2004 | Justin et al. |
| 2004/0082960 A1 | 4/2004 | Davison |
| 2004/0082999 A1 | 4/2004 | Mathys |
| 2004/0087951 A1 | 5/2004 | Khalili |
| 2004/0092952 A1 | 5/2004 | Newton |
| 2004/0093082 A1 | 5/2004 | Ferree |
| 2004/0097935 A1 | 5/2004 | Richelsoph |
| 2004/0102846 A1 | 5/2004 | Keller |
| 2004/0117019 A1 | 6/2004 | Trieu |
| 2004/0117022 A1 | 6/2004 | Marnay |
| 2004/0127897 A1 | 7/2004 | Freid |
| 2004/0127899 A1 | 7/2004 | Konieczynski |
| 2004/0127900 A1 | 7/2004 | Konieczynski |
| 2004/0127904 A1 | 7/2004 | Konieczynski |
| 2004/0133201 A1 | 7/2004 | Shluzas |
| 2004/0133278 A1 | 7/2004 | Marino |
| 2004/0138662 A1 | 7/2004 | Landry |
| 2004/0143265 A1 | 7/2004 | Landry |
| 2004/0143266 A1 | 7/2004 | Kozak |
| 2004/0147928 A1 | 7/2004 | Landry |
| 2004/0147937 A1 | 7/2004 | Dunbar |
| 2004/0153065 A1 | 8/2004 | Lim |
| 2004/0153069 A1 | 8/2004 | Paul |
| 2004/0153157 A1 | 8/2004 | Keller |
| 2004/0172022 A1 | 9/2004 | Landry |
| 2004/0204712 A1 | 10/2004 | Kolb |
| 2004/0204760 A1 | 10/2004 | Fitz |
| 2004/0210221 A1 | 10/2004 | Kozak |
| 2004/0215190 A1 | 10/2004 | Nguyen |
| 2004/0230100 A1 | 11/2004 | Shluzas |
| 2004/0230191 A1 | 11/2004 | Frey |
| 2004/0236334 A1 | 11/2004 | Michelson |
| 2005/0004519 A1 | 1/2005 | VanJaarsveldt |
| 2005/0004593 A1 | 1/2005 | Simonson |
| 2005/0021030 A1 | 1/2005 | Pagliuca |
| 2005/0021031 A1 | 1/2005 | Foley |
| 2005/0021042 A1 | 1/2005 | Marnay |
| 2005/0021143 A1 | 1/2005 | Keller |
| 2005/0021149 A1 | 1/2005 | Borruto |
| 2005/0027293 A1 | 2/2005 | LeHuec |
| 2005/0033297 A1 | 2/2005 | Davison |
| 2005/0033298 A1 | 2/2005 | Hawkes |
| 2005/0033299 A1 | 2/2005 | Shluzas |
| 2005/0033437 A1 | 2/2005 | Bao |
| 2005/0060034 A1 | 3/2005 | Berry |
| 2005/0065516 A1 | 3/2005 | Jahng |
| 2005/0065517 A1 | 3/2005 | Chin |
| 2005/0071011 A1 | 3/2005 | Ralph |
| 2005/0075540 A1 | 4/2005 | Shluzas |
| 2005/0075644 A1 | 4/2005 | DiPoto |
| 2005/0080418 A1 | 4/2005 | Simonson |
| 2005/0085813 A1 | 4/2005 | Spitler |
| 2005/0085911 A1 | 4/2005 | Link |
| 2005/0085917 A1 | 4/2005 | Marnay |
| 2005/0090822 A1 | 4/2005 | DiPoto |
| 2005/0090824 A1 | 4/2005 | Shluzas |
| 2005/0090833 A1 | 4/2005 | DiPoto |
| 2005/0090899 A1 | 4/2005 | DiPoto |
| 2005/0107789 A1 | 5/2005 | Sweeney |
| 2005/0131408 A1 | 6/2005 | Sicvol |
| 2005/0131419 A1 | 6/2005 | McCord |
| 2005/0131420 A1 | 6/2005 | Techiera |
| 2005/0131421 A1 | 6/2005 | Anderson |
| 2005/0131422 A1 | 6/2005 | Anderson |
| 2005/0137593 A1 | 6/2005 | Gray |
| 2005/0149022 A1 | 7/2005 | Shaolian |
| 2005/0149036 A1 | 7/2005 | Varieur |
| 2005/0149053 A1 | 7/2005 | Varieur |
| 2005/0154389 A1 | 7/2005 | Selover |
| 2005/0159651 A1 | 7/2005 | Raymond |
| 2005/0165485 A1 | 7/2005 | Trieu |
| 2005/0171540 A1 | 8/2005 | Lim |
| 2005/0171551 A1 | 8/2005 | Sukovich |
| 2005/0177156 A1 | 8/2005 | Timm |
| 2005/0177164 A1 | 8/2005 | Walters |
| 2005/0182409 A1 | 8/2005 | Callahan |
| 2005/0192570 A1 | 9/2005 | Jackson |
| 2005/0192579 A1 | 9/2005 | Jackson |
| 2005/0192580 A1 | 9/2005 | Dalton |
| 2005/0192589 A1 | 9/2005 | Raymond |
| 2005/0192671 A1 | 9/2005 | Bao |
| 2005/0215999 A1 | 9/2005 | Birkmeyer |
| 2005/0216002 A1 | 9/2005 | Simonson |
| 2005/0228380 A1 | 10/2005 | Moore |
| 2005/0228400 A1 | 10/2005 | Chao |
| 2005/0234456 A1 | 10/2005 | Malandain |
| 2005/0245942 A1 | 11/2005 | DiPoto |
| 2005/0251137 A1 | 11/2005 | Bail |
| 2005/0251192 A1 | 11/2005 | Shluzas |
| 2005/0266581 A1 | 12/2005 | Droit |
| 2005/0267474 A1 | 12/2005 | Dalton |
| 2005/0273105 A1 | 12/2005 | Konieczynski |
| 2005/0273131 A1 | 12/2005 | Shluzas |
| 2005/0273132 A1 | 12/2005 | Shluzas |
| 2005/0273133 A1* | 12/2005 | Shluzas .............. A61B 17/3439 606/198 |
| 2005/0283245 A1 | 12/2005 | Gordon et al. |
| 2005/0288671 A1 | 12/2005 | Yuan |
| 2006/0004453 A1 | 1/2006 | Bartish |
| 2006/0004455 A1* | 1/2006 | Leonard ............. A61B 17/8858 623/17.15 |
| 2006/0020342 A1 | 1/2006 | Ferree |
| 2006/0036244 A1 | 2/2006 | Spitler |
| 2006/0041260 A1 | 2/2006 | Orbay |
| 2006/0041614 A1 | 2/2006 | Oe |
| 2006/0074432 A1* | 4/2006 | Stad .................. A61F 2/4611 606/90 |
| 2006/0074445 A1 | 4/2006 | Gerber |
| 2006/0079900 A1 | 4/2006 | Mathieu |
| 2006/0089651 A1 | 4/2006 | Trudeau |
| 2006/0106387 A1 | 5/2006 | Fanger |
| 2006/0111714 A1 | 5/2006 | Foley |
| 2006/0116689 A1* | 6/2006 | Albans ................ A61B 17/025 606/92 |
| 2006/0122602 A1 | 6/2006 | Konieczynski |
| 2006/0122604 A1 | 6/2006 | Gorhan |
| 2006/0149256 A1 | 7/2006 | Wagner |
| 2006/0155278 A1 | 7/2006 | Warnick |
| 2006/0161157 A1 | 7/2006 | Mosca |

(56) References Cited

U.S. PATENT DOCUMENTS

| | | |
|---|---|---|
| 2006/0173456 A1 | 8/2006 | Hawkes |
| 2006/0200135 A1 | 9/2006 | Sherman |
| 2006/0200147 A1 | 9/2006 | Ensign |
| 2006/0212122 A1 | 9/2006 | Perera |
| 2006/0229614 A1 | 10/2006 | Foley |
| 2006/0235393 A1 | 10/2006 | Bono |
| 2006/0235399 A1 | 10/2006 | Cads |
| 2006/0235411 A1 | 10/2006 | Blain |
| 2006/0235426 A1 | 10/2006 | Lim et al. |
| 2006/0235527 A1 | 10/2006 | Buettner-Janz |
| 2006/0235528 A1 | 10/2006 | Buettner-Janz |
| 2006/0235531 A1 | 10/2006 | Buettner-Janz |
| 2006/0241600 A1 | 10/2006 | Ensign |
| 2006/0241616 A1 | 10/2006 | Konieczynski |
| 2006/0241618 A1 | 10/2006 | Gasser |
| 2006/0247630 A1 | 11/2006 | Iott |
| 2006/0247636 A1 | 11/2006 | Yuan |
| 2006/0264962 A1 | 11/2006 | Chin |
| 2006/0271087 A1 | 11/2006 | VonDyck |
| 2006/0276791 A1 | 12/2006 | Shluzas |
| 2006/0276792 A1 | 12/2006 | Ensign |
| 2007/0010817 A1 | 1/2007 | de Coninck |
| 2007/0027547 A1 | 2/2007 | Rydell |
| 2007/0055235 A1 | 3/2007 | Janowski |
| 2007/0078460 A1 | 4/2007 | Frigg |
| 2007/0093817 A1 | 4/2007 | Barrus |
| 2007/0093826 A1 | 4/2007 | Hawkes |
| 2007/0093827 A1 | 4/2007 | Warnick |
| 2007/0093838 A1 | 4/2007 | Khodadadyan-Klostermann et al. |
| 2007/0093850 A1 | 4/2007 | Harris et al. |
| 2007/0100454 A1 | 5/2007 | Burgess |
| 2007/0123879 A1 | 5/2007 | Songer |
| 2007/0142843 A1 | 6/2007 | Dye |
| 2007/0185491 A1 | 8/2007 | Foley |
| 2007/0198015 A1 | 8/2007 | Foley |
| 2007/0213714 A1 | 9/2007 | Justis |
| 2007/0225711 A1 | 9/2007 | Ensign |
| 2007/0225717 A1 | 9/2007 | Hawkes |
| 2007/0288004 A1 | 12/2007 | Alvarez |
| 2008/0009870 A1 | 1/2008 | Lombardo |
| 2008/0009880 A1 | 1/2008 | Warnick |
| 2008/0015597 A1 | 1/2008 | Whipple |
| 2008/0039839 A1 | 2/2008 | Songer |
| 2008/0039840 A1 | 2/2008 | Songer |
| 2008/0045956 A1 | 2/2008 | Songer |
| 2008/0077153 A1 | 3/2008 | Pernsteiner |
| 2008/0077241 A1 | 3/2008 | Nguyen |
| 2008/0109081 A1 | 5/2008 | Bao |
| 2008/0114359 A1 | 5/2008 | Murner |
| 2008/0140129 A1* | 6/2008 | Dalton .............. A61B 17/7059 606/280 |
| 2008/0154277 A1 | 6/2008 | Machalk |
| 2008/0172054 A1 | 7/2008 | Claypool |
| 2008/0172094 A1 | 7/2008 | Mathieu |
| 2008/0177330 A1 | 7/2008 | Ralph |
| 2008/0195155 A1 | 8/2008 | Hoffman |
| 2008/0208262 A1 | 8/2008 | Butler |
| 2008/0208263 A1 | 8/2008 | Butler |
| 2008/0228233 A1 | 9/2008 | Hoffman |
| 2008/0234750 A1 | 9/2008 | Woods |
| 2008/0243192 A1 | 10/2008 | Jacene |
| 2008/0269809 A1 | 10/2008 | Garamszegi |
| 2008/0288081 A1 | 11/2008 | Scrafton |
| 2008/0306488 A1 | 12/2008 | Altarac |
| 2008/0306489 A1 | 12/2008 | Altarac |
| 2008/0319488 A1 | 12/2008 | Helgerson |
| 2009/0036933 A1 | 2/2009 | Dube |
| 2009/0043390 A1 | 2/2009 | Meisel |
| 2009/0054901 A1 | 2/2009 | Oh |
| 2009/0164023 A1 | 6/2009 | Devine |
| 2009/0185904 A1 | 7/2009 | Landberg |
| 2009/0228054 A1 | 9/2009 | Hoffman |
| 2009/0270927 A1 | 10/2009 | Perrow |
| 2009/0326580 A1 | 12/2009 | Anderson |
| 2010/0160977 A1 | 6/2010 | Gephart |
| 2010/0249797 A1 | 9/2010 | Trudeau |
| 2010/0312279 A1 | 12/2010 | Gephart |
| 2011/0054621 A1 | 3/2011 | Lim |
| 2012/0185045 A1 | 7/2012 | Morris |
| 2012/0203344 A1 | 8/2012 | Trudeau |
| 2012/0310287 A1 | 12/2012 | Bao |
| 2013/0296941 A1 | 11/2013 | Perrow |
| 2014/0277473 A1 | 9/2014 | Perrow |
| 2014/0324104 A1 | 10/2014 | Kilpela |
| 2015/0100130 A1 | 4/2015 | Perrow |
| 2015/0265414 A1 | 9/2015 | Mermuys |
| 2016/0081723 A1 | 3/2016 | Perrow |

FOREIGN PATENT DOCUMENTS

| | | |
|---|---|---|
| CA | 2548780 | 7/2005 |
| CN | 1697633 | 11/2005 |
| DE | 9000094 | 1/1991 |
| DE | 9000094 U1 | 1/1991 |
| DE | 29911422 | 8/1999 |
| DE | 29911422 U1 | 8/1999 |
| DE | 10226496 | 6/2001 |
| DE | 10130825 | 3/2002 |
| EP | 0179695 | 4/1986 |
| EP | 03646129 | 12/1989 |
| EP | 0773008 | 5/1997 |
| EP | 0773008 A1 | 5/1997 |
| EP | 0919209 | 6/1999 |
| EP | 0988833 | 3/2000 |
| EP | 1104665 | 6/2001 |
| EP | 1205160 | 5/2002 |
| EP | 1336383 | 8/2003 |
| EP | 1340468 | 9/2003 |
| EP | 1346697 | 9/2003 |
| EP | 1858422 | 11/2007 |
| FR | 2372622 | 6/1978 |
| FR | 2723841 | 3/1996 |
| FR | 2787014 | 6/2000 |
| FR | 2797179 | 2/2001 |
| FR | 2799116 | 4/2001 |
| FR | 2805985 | 9/2001 |
| FR | 2824261 | 11/2002 |
| JP | 63300758 | 12/1988 |
| JP | 1308557 | 12/1989 |
| JP | 01142293 | 4/1990 |
| JP | 02111358 | 4/1990 |
| JP | 2215461 | 8/1990 |
| JP | 2224659 | 9/1990 |
| JP | 2224660 | 9/1990 |
| JP | 04303444 | 10/1992 |
| JP | 05277141 | 10/1993 |
| JP | 06285099 | 10/1994 |
| JP | 08098850 | 4/1996 |
| JP | 08098851 | 4/1996 |
| JP | 11009618 | 1/1999 |
| JP | 11137585 | 5/1999 |
| JP | 2008284348 | 11/2008 |
| WO | 8803781 | 6/1988 |
| WO | 198803781 | 6/1988 |
| WO | 9011740 | 10/1990 |
| WO | 9105521 | 5/1991 |
| WO | 9116867 | 11/1991 |
| WO | 9316664 | 9/1993 |
| WO | 9500082 | 5/1995 |
| WO | 9601598 | 1/1996 |
| WO | 9608206 | 3/1996 |
| WO | 199608206 | 3/1996 |
| WO | 9611642 | 4/1996 |
| WO | 9627339 | 9/1996 |
| WO | 9639975 | 12/1996 |
| WO | 199639975 | 12/1996 |
| WO | 9722306 | 6/1997 |
| WO | 199722306 | 6/1997 |
| WO | 9805274 | 2/1998 |
| WO | 9819617 | 5/1998 |
| WO | 9834553 | 8/1998 |
| WO | 9834556 | 8/1998 |
| WO | 199834553 | 8/1998 |
| WO | 199834556 | 8/1998 |

(56) References Cited

FOREIGN PATENT DOCUMENTS

| | | |
|---|---|---|
| WO | 9851226 | 11/1998 |
| WO | 199851226 | 11/1998 |
| WO | 9855053 | 12/1998 |
| WO | 9904718 | 2/1999 |
| WO | 199904718 | 2/1999 |
| WO | 9911203 | 3/1999 |
| WO | 9922675 | 5/1999 |
| WO | 9930651 | 6/1999 |
| WO | 0003653 | 1/2000 |
| WO | 200003653 | 1/2000 |
| WO | 0013619 | 3/2000 |
| WO | 0042953 | 7/2000 |
| WO | 0059412 | 10/2000 |
| WO | 0066011 | 11/2000 |
| WO | 200066011 | 11/2000 |
| WO | 0078238 | 12/2000 |
| WO | 200078238 | 12/2000 |
| WO | 0115638 | 3/2001 |
| WO | 0126566 | 4/2001 |
| WO | 200126566 | 4/2001 |
| WO | 0132100 | 5/2001 |
| WO | 0149191 | 7/2001 |
| WO | 200149191 | 7/2001 |
| WO | 0168003 | 9/2001 |
| WO | 02058574 | 8/2002 |
| WO | 2002058574 | 8/2002 |
| WO | 02087480 | 11/2002 |
| WO | 03035129 | 5/2003 |
| WO | 03063714 | 8/2003 |
| WO | 2003063714 | 8/2003 |
| WO | 03099172 | 12/2003 |
| WO | 2004017847 A2 | 3/2004 |
| WO | 2004047650 | 6/2004 |
| WO | 2004071339 | 8/2004 |
| WO | 2005009298 | 2/2005 |
| WO | 2005041818 | 5/2005 |
| WO | 2005051240 | 6/2005 |
| WO | 2005053550 | 6/2005 |
| WO | 2006016384 | 2/2006 |
| WO | 2006061114 | 6/2006 |
| WO | 2006091863 | 8/2006 |
| WO | 2008024937 | 2/2008 |
| WO | 2008051707 | 5/2008 |
| WO | 2008055648 | 5/2008 |

OTHER PUBLICATIONS

Depuy Spine, Inc., Charite Artificial Disc Product Catalog, Dec. 2004, 16 pp.
Feder, B., When F.D.A. Says Yes, But Insurers Say No, The New York Times, Jul. 6, 2005, 2 pp.
Zdeblick, T. et al, Cervical Interbody Cages, An Animal Mode With and Without Bone Morphogenetic Protein, Spine, 1998, vol. 23, No. 7, 11 pp.
Foley, M.D., Kevin T., Schwender, MD., James D., and Rouben, MD., David P., PyrametriX.RTM. Advance: Instrument Set Technique, surgical brochure provided by manufacturer Medtronic Sofamor Danek, Inc., 2005, (25 pages).
Bao et al., Artificial Disc Technology, Neurosurg. Focus 9(4), Oct. 2000, 7 pp.

\* cited by examiner

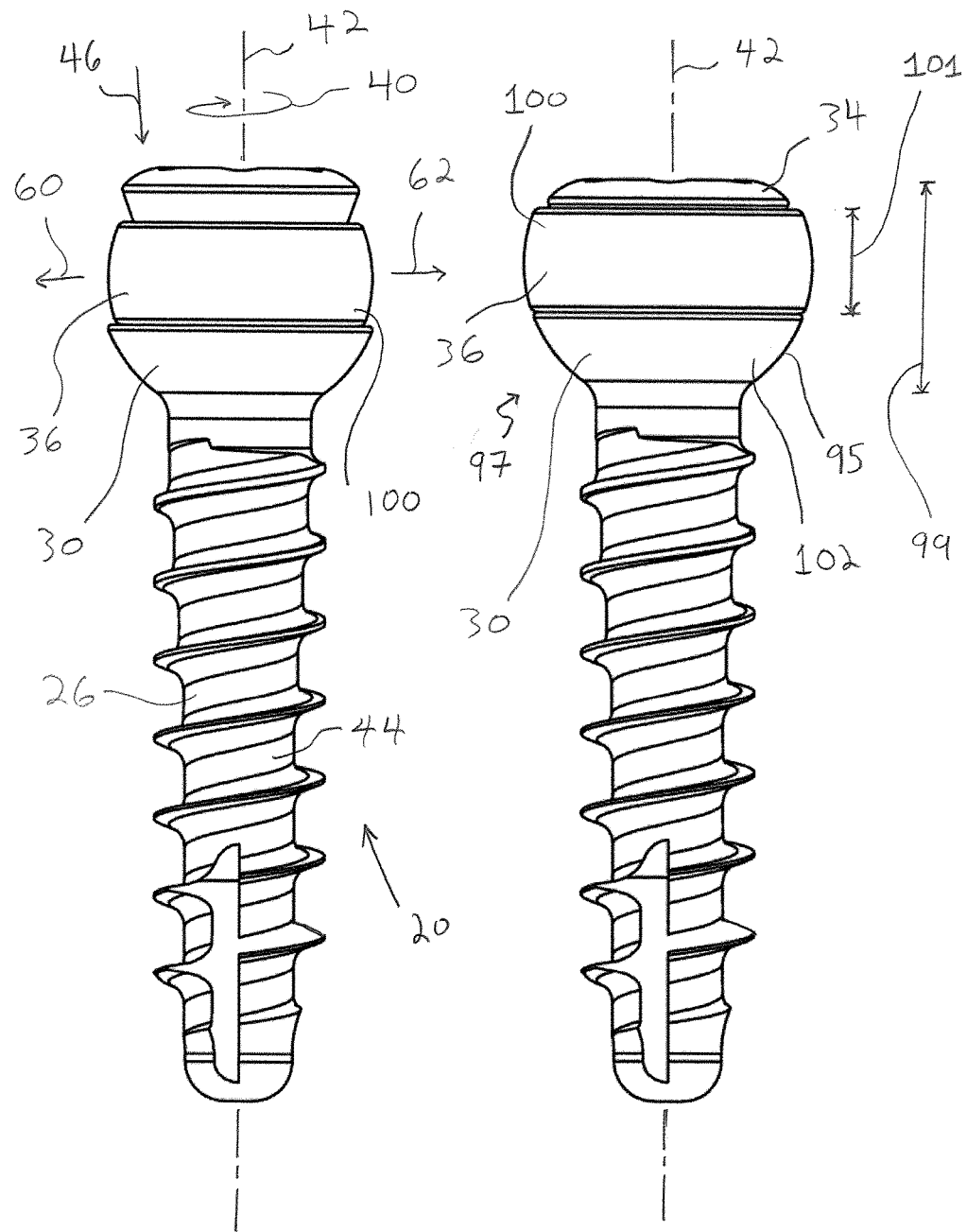

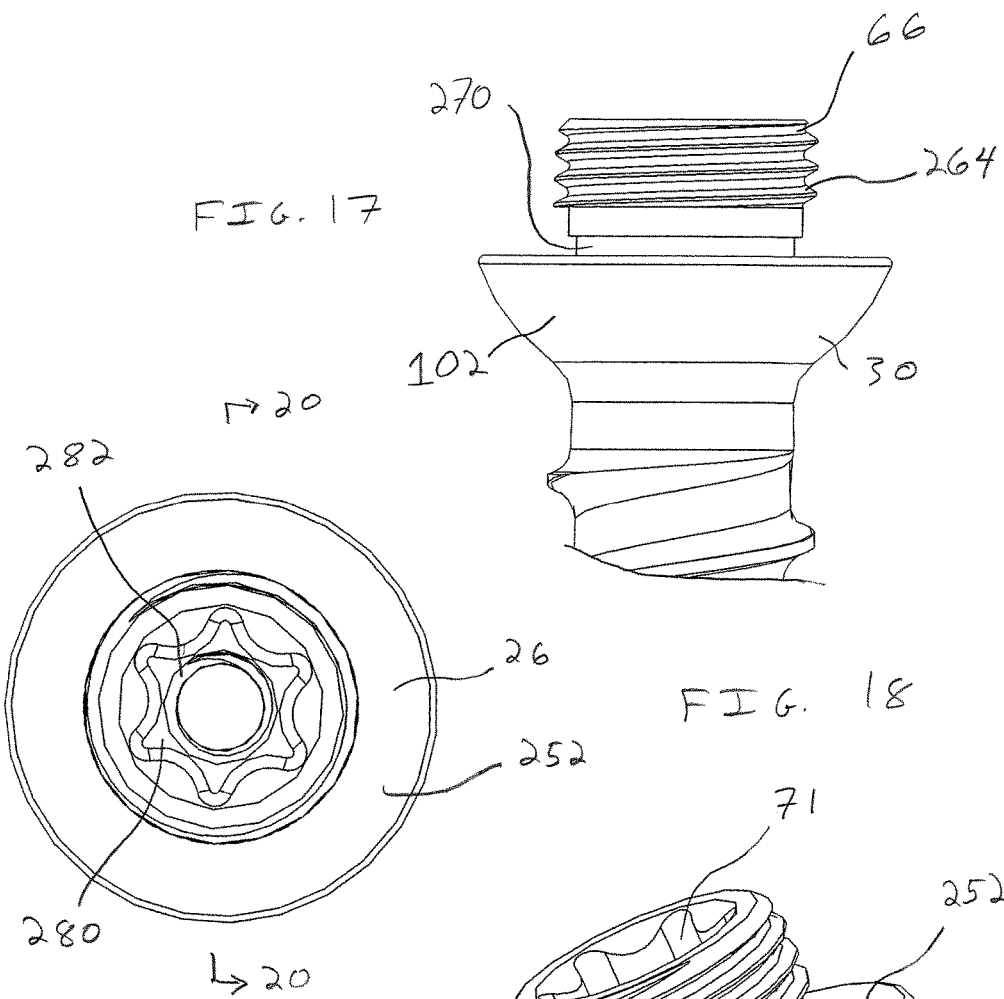
FIG. 17
FIG. 18
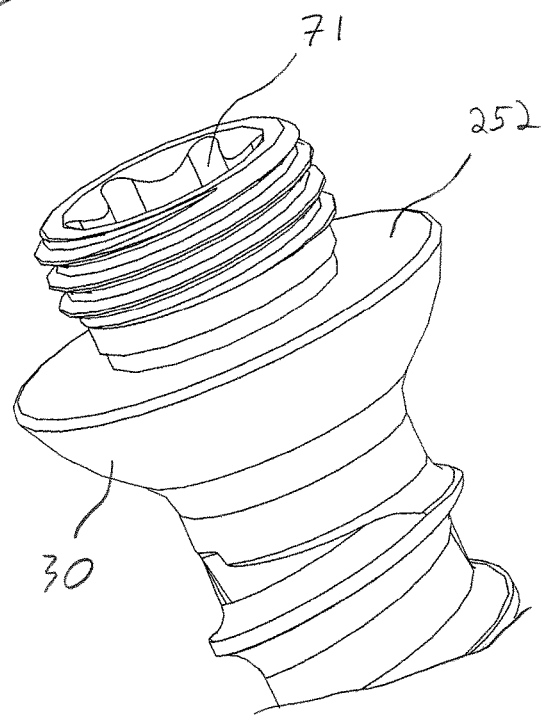
FIG. 19

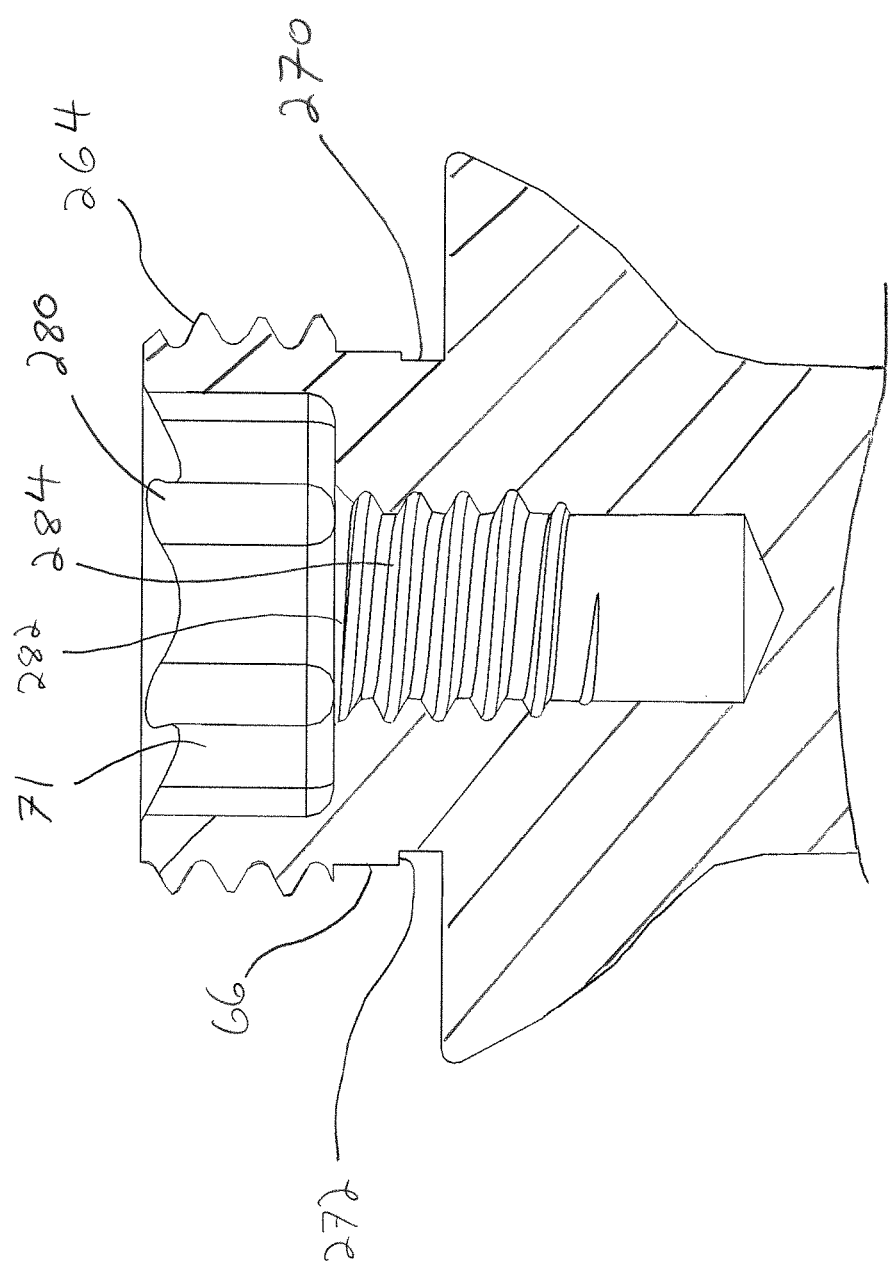

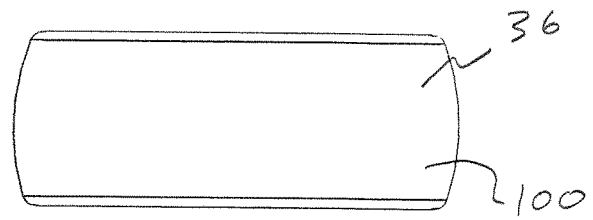
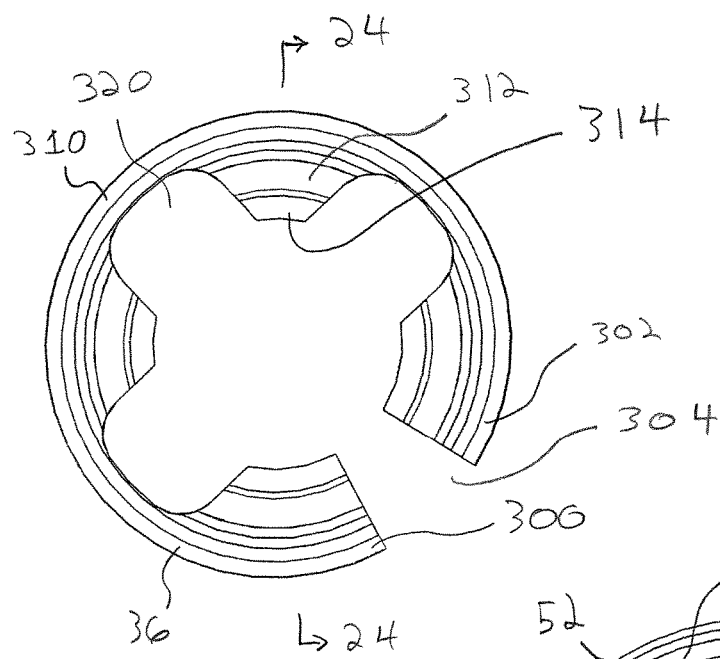
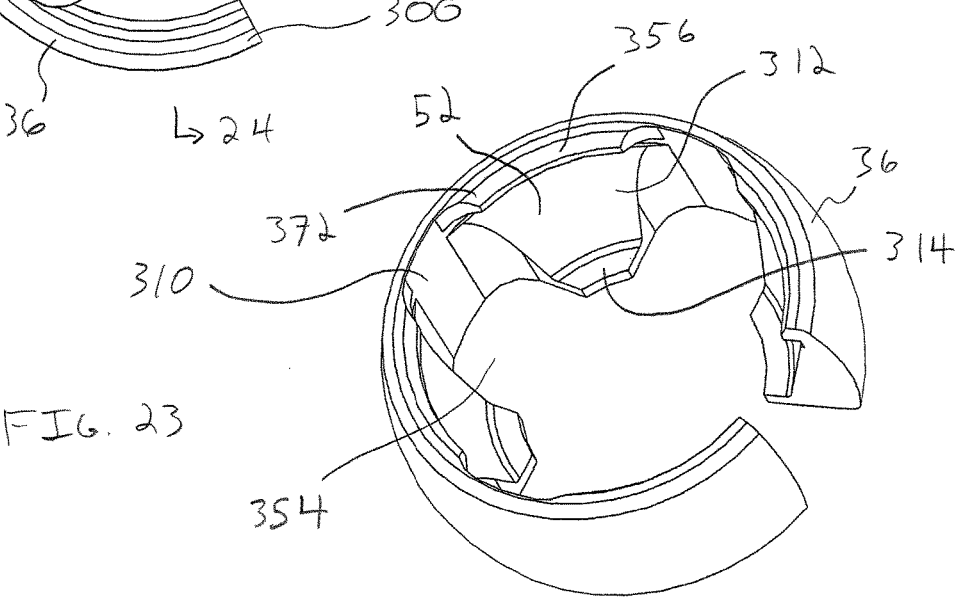

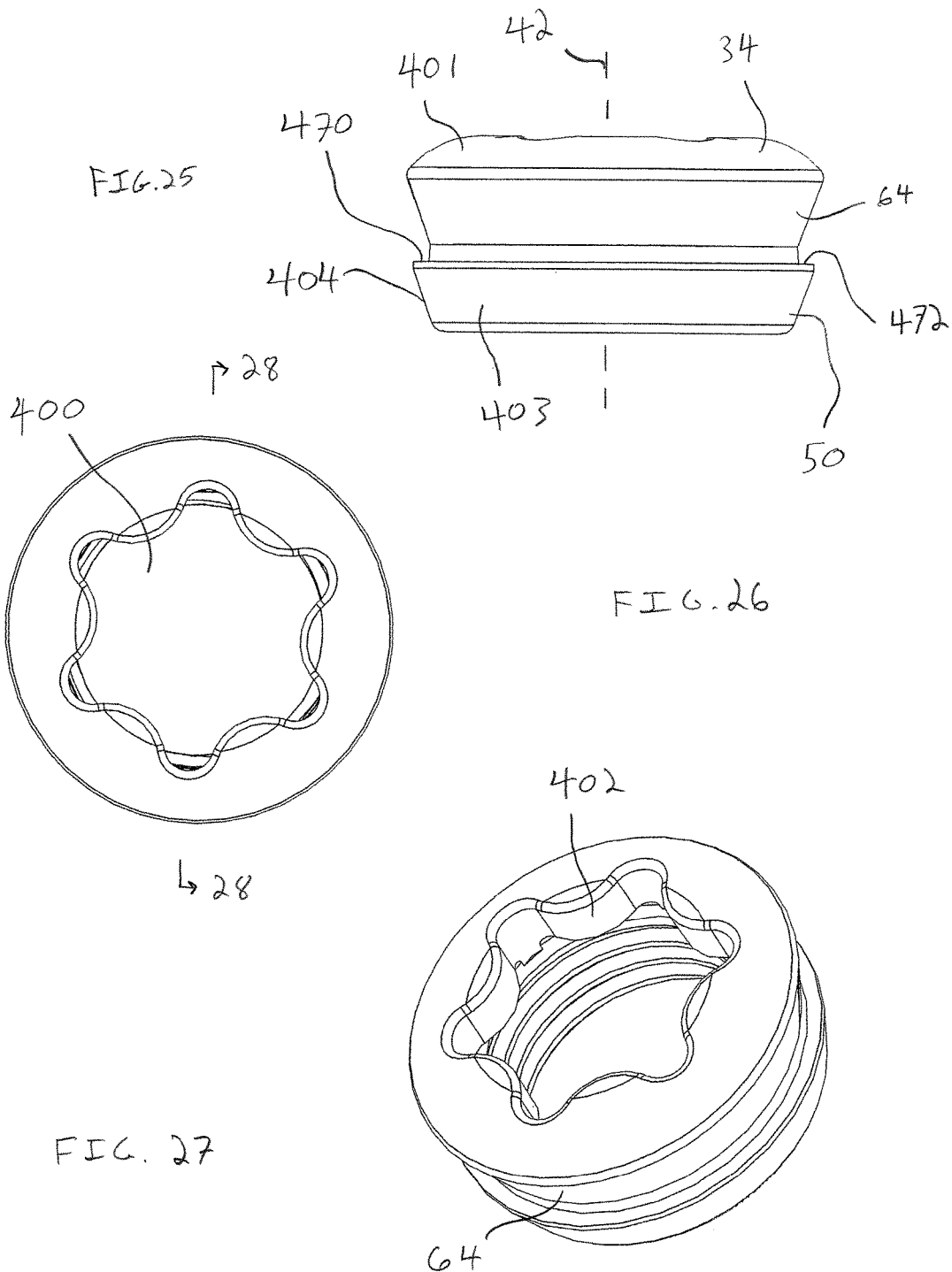

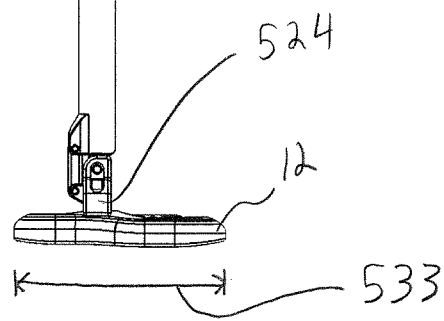
FIG. 32A

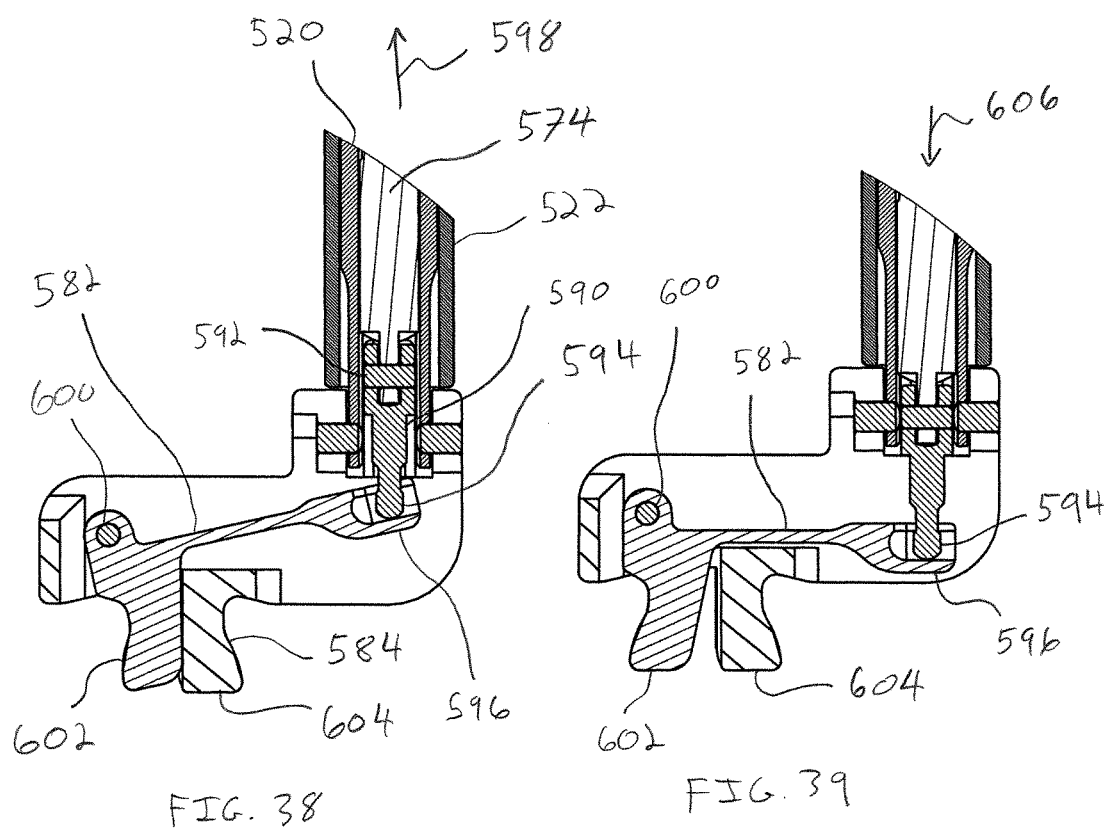

METHOD OF IMPLANTING A BONE PLATE

CROSS-REFERENCE TO RELATED APPLICATION

This application is a continuation of U.S. patent application Ser. No. 13/725,420, filed Dec. 21, 2012, which claims the benefit of U.S. Provisional Patent Application No. 61/580,055, filed Dec. 23, 2011, both of which are hereby incorporated by reference in their entireties.

FIELD OF THE INVENTION

The invention relates to bone plate systems and, more particularly, to bone plate systems for stabilizing one or more bones.

BACKGROUND OF THE INVENTION

There are presently many different types of bone plate systems for securing bones so that the secured bones may fuse or heal. As used herein, the term bone may refer to a bone, a bone fragment, or a portion of a bone. Bone plate systems often utilize a bone plate having throughbores and bone screw assemblies that are driven through the throughbores and into the underlying bone for securing the bone plate to one or more bones. In some applications, the bone screw assemblies include a bone screw that is driven into bone and a device associated with the bone screw for restricting back-out of the bone screw once the bone anchor assembly has been seated in the throughbore of the bone plate. The device may include a resilient head of the bone screw for being seated within one of the throughbores and a set screw that is threaded into the resilient head to expand the head against walls of the throughbore and restrict back-out of the bone screw. However, the resilient head is weaker than the remainder of the bone screw in order to permit expansion of the head as the set screw is threaded into the head. Further, the set screw is relatively small and may be difficult to thread into the bone screw head during surgery.

Another type of bone plate system utilizes bone screws having heads with resilient c-rings carried thereon and locking members disposed within the bone screws for restricting back-out of the bone screws from throughbores of the bone plate. Once the heads of the bone screws have been seated within the throughbores, the locking members are longitudinally shifted within the bone screw to radially expand the c-ring into engagement with walls of the throughbore. The c-ring has an outer annular portion for engaging the throughbore walls and inner, radially extending portions configured to contact the locking member and shift the outer annular portion radially outward with longitudinal shifting of the locking member. However, the radially extending portions are thin and may deflect when loads are applied to bone screw, such as post-operation movement of the patient. Deflection of the radially extending portions may, over time, reduce the strength of radially extending portions and the overall stability of the bone plate system.

In some instances, a predetermined amount of pivoting between a bone screw and a bone plate of a bone plate system is desired to accommodate settling of the bones. The pivoting is preferably controlled movement, rather than free movement between the bone screw and bone plate which may interfere with fusion of the bones. Although bone screws having c-ring back-out prevention devices may be used in these applications, the c-rings themselves have an outer surface for engaging the bone plate throughbore walls that is relatively thin compared to the bone screw head, e.g., less than a quarter of the height of the bone screw head. The short vertical extent of the c-ring outer surface along the throughbore wall limits the contact area and frictional engagement between the c-ring outer surface and the throughbore wall. This is undesirable in some instances because the limited frictional engagement provided by the c-ring limits the ability of the expanded c-ring to control pivoting of the bone screw relative to the bone plate.

Another shortcoming of prior bone plate systems is the ability to use a single bone plate system for a variety of patient anatomies. For example, to stabilize a pair of vertebrae, an intervertebral implant is inserted between the vertebrae and a bone plate system is connected to the vertebrae to secure the vertebrae and the intervertebral implant together. The intervertebral implant may be selected from a number of different shapes and sizes to conform to the patient's anatomy. Due to the possible variation in the intervertebral implant selected for a particular patient, the bone plate system subsequently used to secure the bones should accommodate the range of shapes and sizes of the intervertebral implant that may be used. One prior approach to providing such a bone plate system utilized a bone plate having elongated throughbores. The bone plate is first positioned on a pair of vertebrae stabilized by an intervertebral implant, and then bone screws are driven into the elongated throughbores at locations along the throughbores that permit the bone screws to engage the underlying vertebrae. Although the elongated throughbores provide flexibility in installation, the bone screws can slide along the elongated throughbore as the vertebrae settle. In some instances, this post-operative sliding of the bone screws is undesirable due to the corresponding changes in position of the vertebrae.

SUMMARY OF THE INVENTION

In accordance with one aspect of the invention, a bone anchor assembly is provided that can be driven into bone and securely fixed to a bone plate to secure the bone plate to the bone. The bone anchor assembly includes a bone anchor having a head, a resilient locking cap extending about a portion of the bone anchor head, and a cap drive member with a depending annular wall for fitting about the bone anchor head portion. The depending annular wall is disposed radially between the bone anchor head portion and the locking cap. The depending annular wall can thereby directly transfer loading between and bone anchor head portion and the locking cap with substantially no deflection or other flexing of the locking cap, which strengthens the connection between the bone anchor assembly and the bone plate.

To radially expand the locking cap, the cap drive member is shiftable axially along an outer periphery of the bone anchor portion. The cap drive member and the locking cap have engagement surfaces configured to engage and radially expand the locking cap as the cap drive member shifts axially from an unlocked to a locked configuration. The engagement surfaces of the cap drive member and locking cap are engaged about and radially adjacent to the bone anchor head portion. In one form, the bone anchor head has drive structure disposed radially inward from the bone anchor head portion, the drive structure being configured to receive a driving tool for driving the bone anchor into bone. Because the engagement surfaces of the cap drive member and the locking cap are engaged about the bone anchor head portion and radially outward from the drive structure, the drive structure of the bone screw is unobstructed by the engagement surfaces of the cap drive member and the locking cap which permits a wide variety of different types of drive structures to be used, such as Torx, hex, and Phillips-type, without being limited by the engagement surfaces of the cap drive member and the locking cap. Further, the bone anchor head is preferably rigid and positioning the engagement surfaces about and radially adjacent to the bone anchor head portion permits the cap drive member to expand the locking cap and secure the bone anchor assembly to a bone plate without the use of a weakened, resilient bone screw head as in some prior approaches.

A bone plate system is also provided that may be manipulated to adjust the location of a bone anchor within the bone plate system and allow the bone plate system to conform to the anatomy of a patient and the surgical procedure being performed. The bone plate system has a bone plate, a plurality of bone anchors for inserting into throughbores of the bone plate, and a resilient support member received in an elongated throughbore of the bone plate. One of the bone anchors has a head and an actuator device carried thereon, and the resilient support member has an opening sized to receive the bone anchor head and the actuator device. The bone plate and support member are configured to permit movement of the support member toward either end of the elongated throughbore before the bone anchor is driven into the support member opening, which permits the support member to be positioned at a desired location along the elongated throughbore. The location of the resilient support member along the throughbore is preferably chosen such that the support member opening is disposed adjacent an underlying bone to permit the bone anchor to be driven through the support member opening and into the bone. By allowing the resilient support member to be moved along the elongated throughbore to a desired location, the bone plate system can accommodate a wider range of possible installation configurations than if the all locations for bone anchors on the plate were static.

For example, if the bone plate system is being used to stabilize a pair of vertebrae on either side of an interverterbral implant, the resilient support member can be moved toward one end of the elongated throughbore if the interverterbral implant selected is relatively large, or toward the opposite end of the elongated throughbore if the interverterbral implant is relatively small, before driving the bone anchor into the opening of the support member. The resilient support member may also be moved along the elongated throughbore to permit placement of the associated bone anchor into a region of a bone that avoids previously implanted hardware in the bone. For example, if a pedicle screw is present in a vertebra, the bone plate may be placed against the vertebra and the resilient support member moved to a position along the throughbore that allows the associated bone anchor to be driven into the vertebral body away from the pedicle screw. This is particularly advantageous when the bone plate system is installed using a lateral approach because the bone anchor can be secured to the vertebral body without having to remove the pedicle screw, which may require a posterior incision and corresponding operation.

The bone plate system also permits the resilient support member and bone anchor received therein to be locked at a selected location along the elongated throughbore. More specifically, the actuator device of the bone anchor may be driven between unlocked and locked positions once the bone anchor head has been received within the support member opening. The resilient support member is expandable and is configured to expand with driving of the actuator device between the unlocked and locked positions. To lock the position of the support member along the elongated throughbore, the resilient support member and bone plate have interfering portions that are configured to be in a fixed or locked orientation relative to each other when the bone anchor actuator device has been driven to the locked position. This keeps the support member, and the bone anchor head received therein, at a selected position along the elongated throughbore against movement toward either end thereof. The bone anchor head may thereby be seated in the support member opening, the actuator device driven to the locked position, and the bone anchor and resilient support member locked at the selected axial position along the throughbore. Thus, the bone plate system provides significant installation flexibility without post-operative translation of the bone anchor along the elongated throughbore.

In another aspect, a method of securing a bone plate to a bone is provided that permits the bone plate to be adjusted to conform to the surgical site before installing the bone plate. The method includes moving a resilient support member disposed within an elongated throughbore of the bone plate along a longitudinal axis of the throughbore to a selected axial position along the throughbore. The axial position of the resilient support member is chosen to orient a through opening of the resilient support member adjacent a bone so that a shank of a bone anchor may be driven through the support member through opening and into the bone. The method further includes seating a head of the bone anchor and an actuator device carried thereon in the support member through opening, driving the actuator device from an unlocked to a locked position, and expanding the support member toward walls of the elongated throughbore as the actuator device is driven to the locked position. The support member and the bone anchor are thereby locked at the selected axial position along the throughbore to resist movement of the bone anchor along the elongated throughbore and the associated translational movement of the bone relative to the bone plate.

BRIEF DESCRIPTION OF THE DRAWINGS

FIG. 3 is an elevational view of one of the bone anchor assemblies of FIG. 1 showing the cap drive member of the bone anchor assembly in an unlocked position;

FIG. 4 is an elevational view similar to FIG. 3 showing the cap drive member shifted to a locked position which radially expands the resilient locking cap of the bone anchor assembly;

FIG. 17 is an elevational view of the bone screw of the bone anchor assembly of FIG. 16 showing the head of the bone screw having a rounded lower surface;

FIG. 18 is a top plan view of the bone screw of FIG. 17 showing a recess for receiving a driving tool;

FIG. 19 is a perspective view of the bone screw of FIG. 17 showing a radially extending bearing surface of the bone screw configured to support the resilient locking cap and a threaded wall upstanding from the bearing surface;

FIG. 20 is a cross-sectional view taken across line 20-20 in FIG. 18 showing a central axial bore for receiving a screw retention portion of the driving tool;

FIG. 21 is an elevational view of the resilient locking cap of the bone anchor assembly of FIG. 16 showing a rounded outer surface of the resilient locking cap;

FIG. 22 is a top plan view of the locking cap of FIG. 21 showing an outer annular wall and radially extending portions of the locking cap;

FIG. 23 is a perspective view of the locking cap of FIG. 1 showing a gap spacing between ends of the locking cap;

FIG. 25 is an elevational view of the cap drive member of the bone screw of FIG. 16 showing a radially outer, inclined surface of the cap drive member configured to engage the radially inner inclined surfaces of the locking cap;

FIG. 26 is a top plan view of the cap drive member of FIG. 17 showing a central opening of the cap drive member;

FIG. 27 is a perspective view of the cap drive member of FIG. 17 showing structures of the cap drive member disposed about the central opening configured to engage a locking tool;

FIG. 32A is a top plan view of the inserter tool of FIG. 32 showing the bone plate pivoted to a generally perpendicular orientation relative to the inserter tool shaft;

FIGS. 38 and 39 are enlarged cross-sectional views generally taken across line 35B-35B in FIG. 32A showing the gripping portion arms in the release and engagement configurations;

DETAILED DESCRIPTION OF THE PREFERRED EMBODIMENTS

Figure 1:
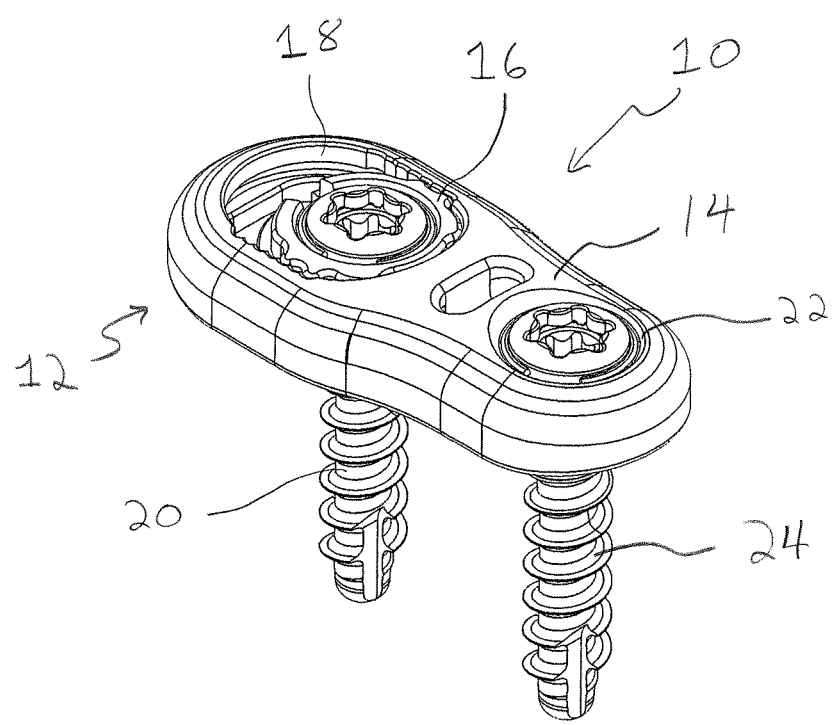
FIG. 1 is a perspective view of a bone plate system in accordance with the present invention showing a bone plate and a pair of bone anchor assemblies connected thereto.
Figure 11:
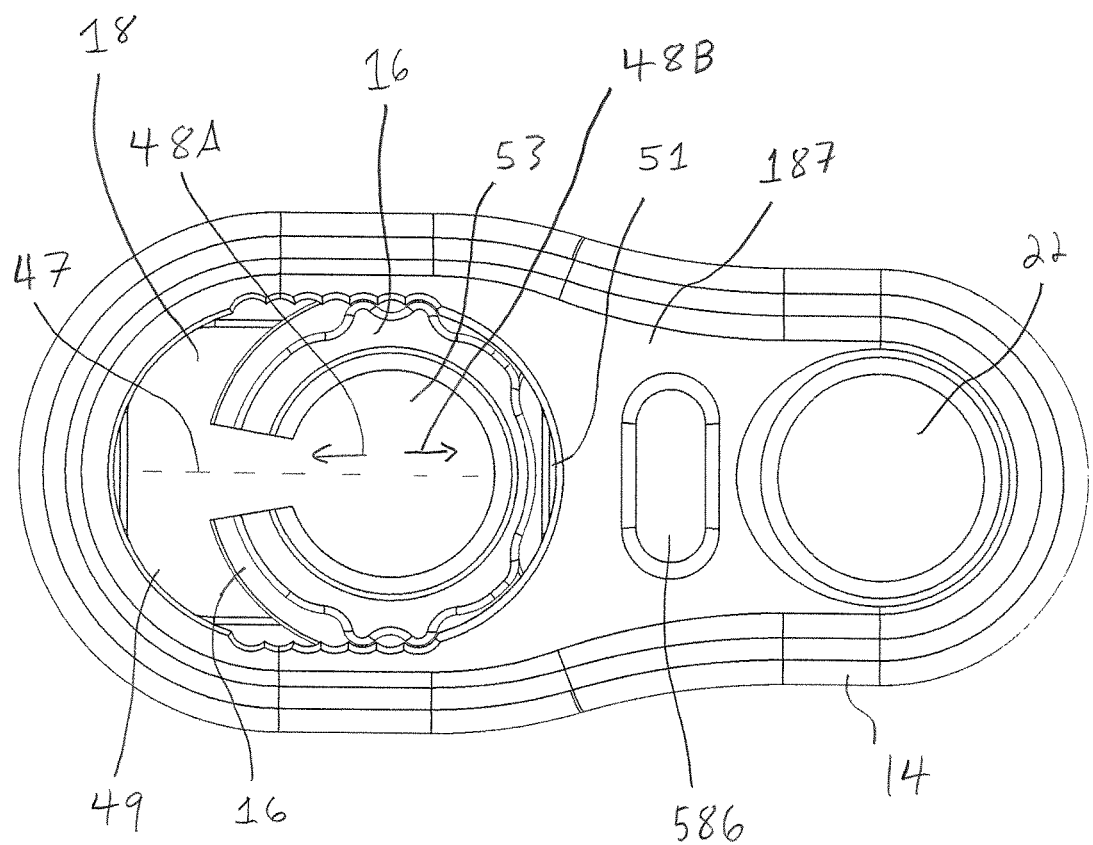
FIG. 11 is a top plan view of the bone plate system of FIG. 1 with the bone anchor assemblies removed to show an opening of the resilient support member in which one of the bone anchor assemblies is received.

With reference to FIGS. 1 and 11, a bone plate system 10 is provided having a bone plate 12 with a bone plate member 14 and a movable resilient support member 16. The support member 16 may be moved along an elongated throughbore 18 of the bone plate member 14 to provide flexibility during installation of the bone plate system 10. More specifically, the bone plate system 10 includes a pair of bone anchor assemblies 20, 24 for securing the bone plate 12 to a pair of bones, with the bone anchor assembly 20 being driven into an opening 53 of the support member 16 and a bone anchor assembly 24 being driven into a non-elongated throughbore 22 of the bone plate member 14 (see FIG. 11). The bone anchor assemblies 20, 24 are preferably preassembled for ease of handling during surgery and can be readily driven into the support member opening 53 and bone plate throughbore 22 to secure the bone plate 12 to bones. Before the bone anchor assembly 20 is driven into the support member opening 53, the resilient support member 16 may be moved within the elongated throughbore 18 to increase or decrease the distance between the support member opening 53 and the non-elongated throughbore 22, and the resulting positions of the bone anchor assemblies 20, 24, in order to permit the bone anchor assemblies 20, 24 to be driven into desired areas of the underlying bones. Once the bone anchor assembly 20 has been driven into the support member opening 53 and received therein, the support member 16 and the bone anchor assembly 20 may be secured at a desired location along the throughbore 18 to restrict translational movement of the bone anchor assemblies 20, 24 relative to each other, as discussed in greater detail below. Thus, the bone plate system 10 provides enhanced flexibility during installation by allowing the position of the support member 16 within the elongated throughbore 18 to be adjusted in situ to conform to the anatomy of the patient before securing the bone plate 12 to the bones using the bone anchor assemblies 20, 24.

Figure 2:
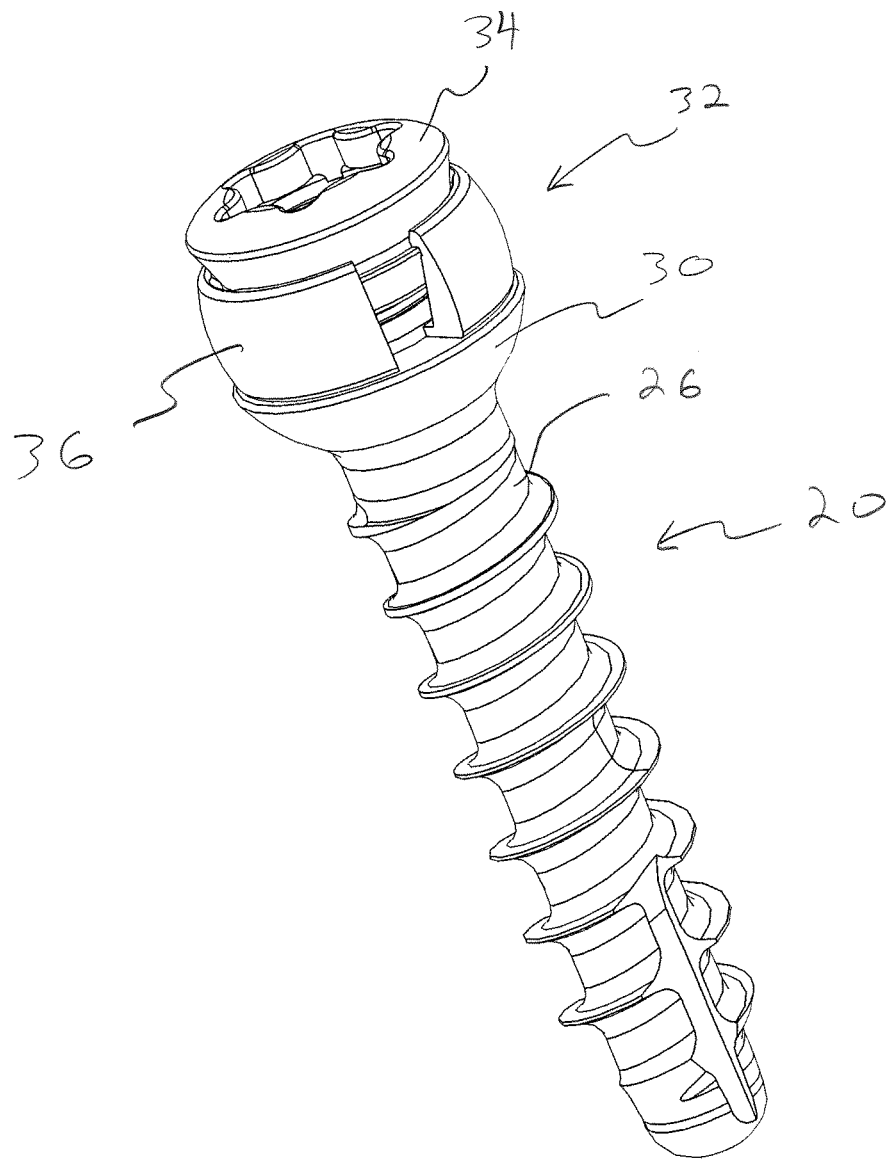
FIG. 2 is a perspective view of one of the bone anchor assemblies of FIG. 1 showing a bone screw, cap drive member, and a resilient locking cap of the bone anchor assembly.

With reference to FIG. 2, the bone anchor assemblies 20, 24 are similar and each have a bone anchor, such as a bone screw 26, for engaging a bone. The bone screw 26 has a bone screw head 30 and an actuator device 32 carried thereon, as shown in FIG. 2. The actuator device 32 is configured to be driven to a locked position after the bone screw 26 has been seated within the support member opening 53. Driving the actuator device 32 of the bone anchor assembly 20 to the locked position tightly engages the bone anchor assembly 20 with the support member 16. Driving the actuator device 32 of the bone anchor assembly 20 also locks the support member 16 to the bone plate member 14 at a selected position along the elongated throughbore 18, as discussed in greater detail below. Similarly, driving the actuator device 32 of the bone anchor assembly 24 to its locked position tightly engages the bone anchor assembly 24 to the plate member 14 within the non-elongated throughbore 22.

In one form, the actuator device 32 includes a cap drive member 34 connected to the bone screw head 30 and a resilient locking cap 36 disposed on the bone screw head 30, as shown in FIG. 2. The connection between the cap drive member 34 and the bone screw head 30 may be a threaded engagement so that clockwise rotation of the cap drive member 34 in direction 40 about a longitudinal axis 42 of the bone anchor assembly 20 advances the cap drive member 34 in direction 46 toward the bone screw head 30, as shown in FIGS. 3 and 4. Movement of the cap drive member 34 in direction 46 toward the bone screw head 30 causes outward expansion of the locking cap 36 in directions 60, 62, which expands the support member 16 and secures the support member 16 and bone anchor assembly 20 at a desired position along the elongated throughbore 18.

Figure 6:
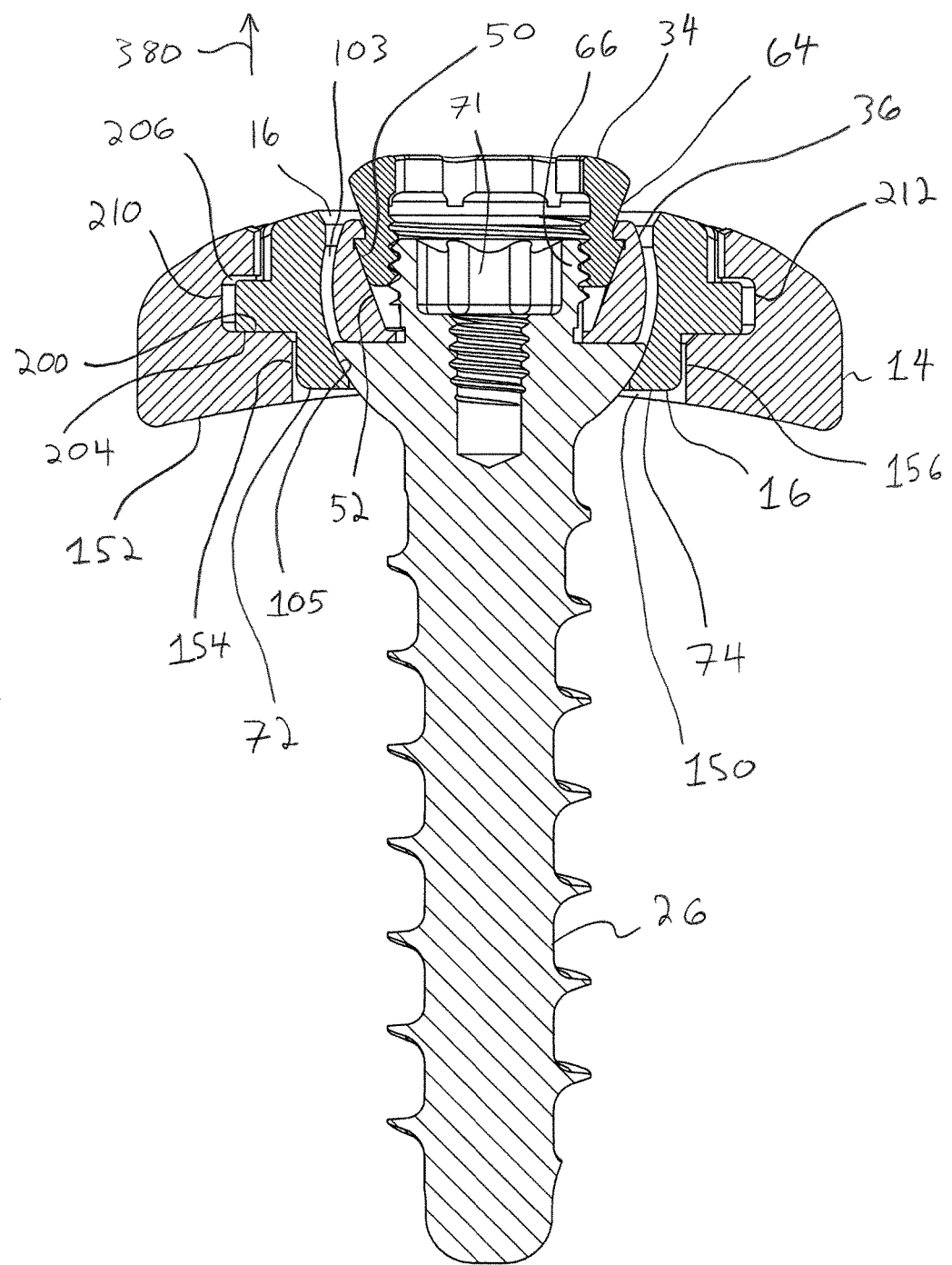
FIG. 6 is a cross-sectional view taken across line 6-6 in FIG. 5 showing a head portion of the bone anchor assembly received in the resilient support member with the cap drive member of the bone anchor assembly in the unlocked position.
Figure 7:
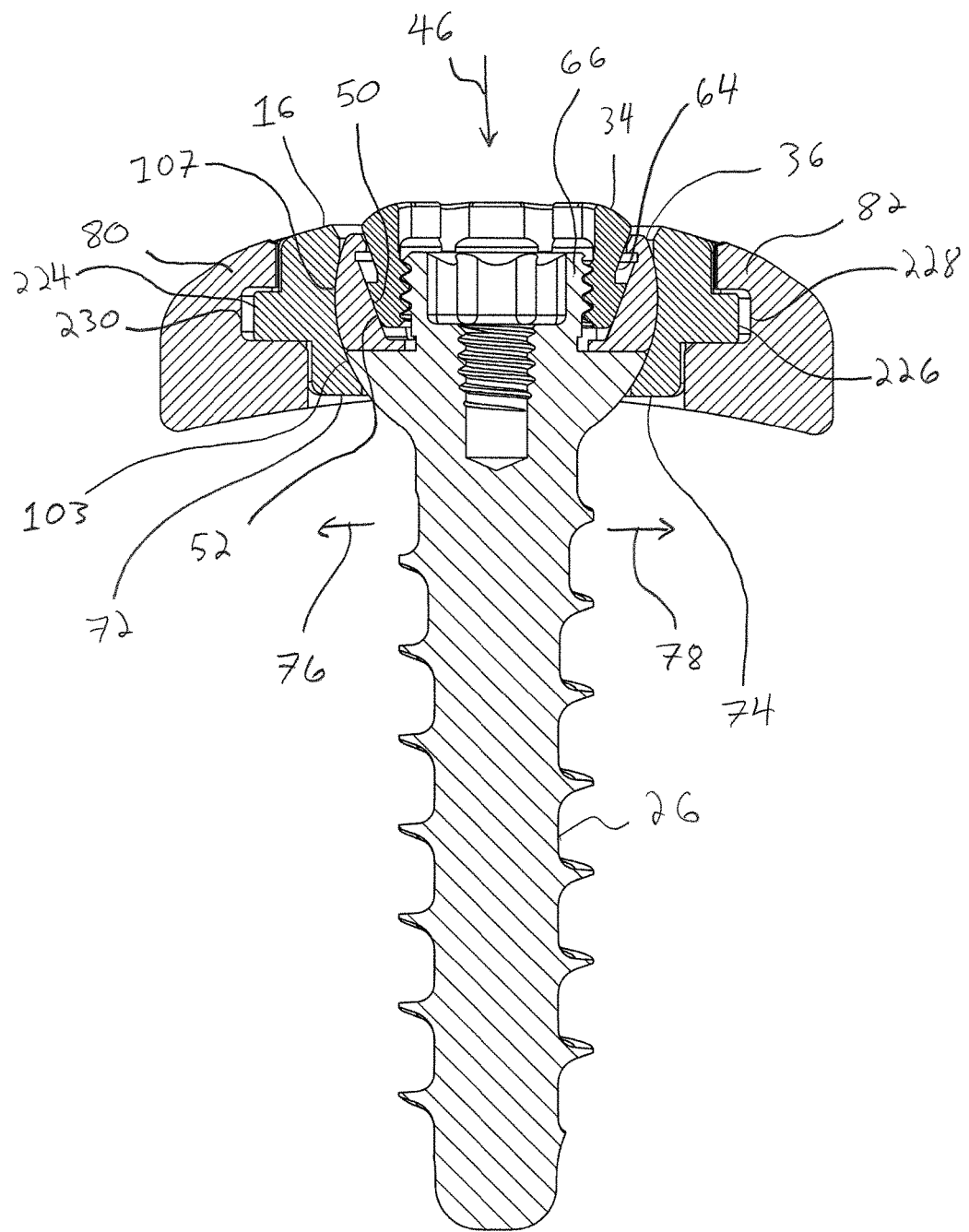
FIG. 7 is a cross-sectional view similar to FIG. 6 showing the cap drive member shifted to the locked position which expands the locking cap and the resilient support member of the bone plate.
Figure 16:
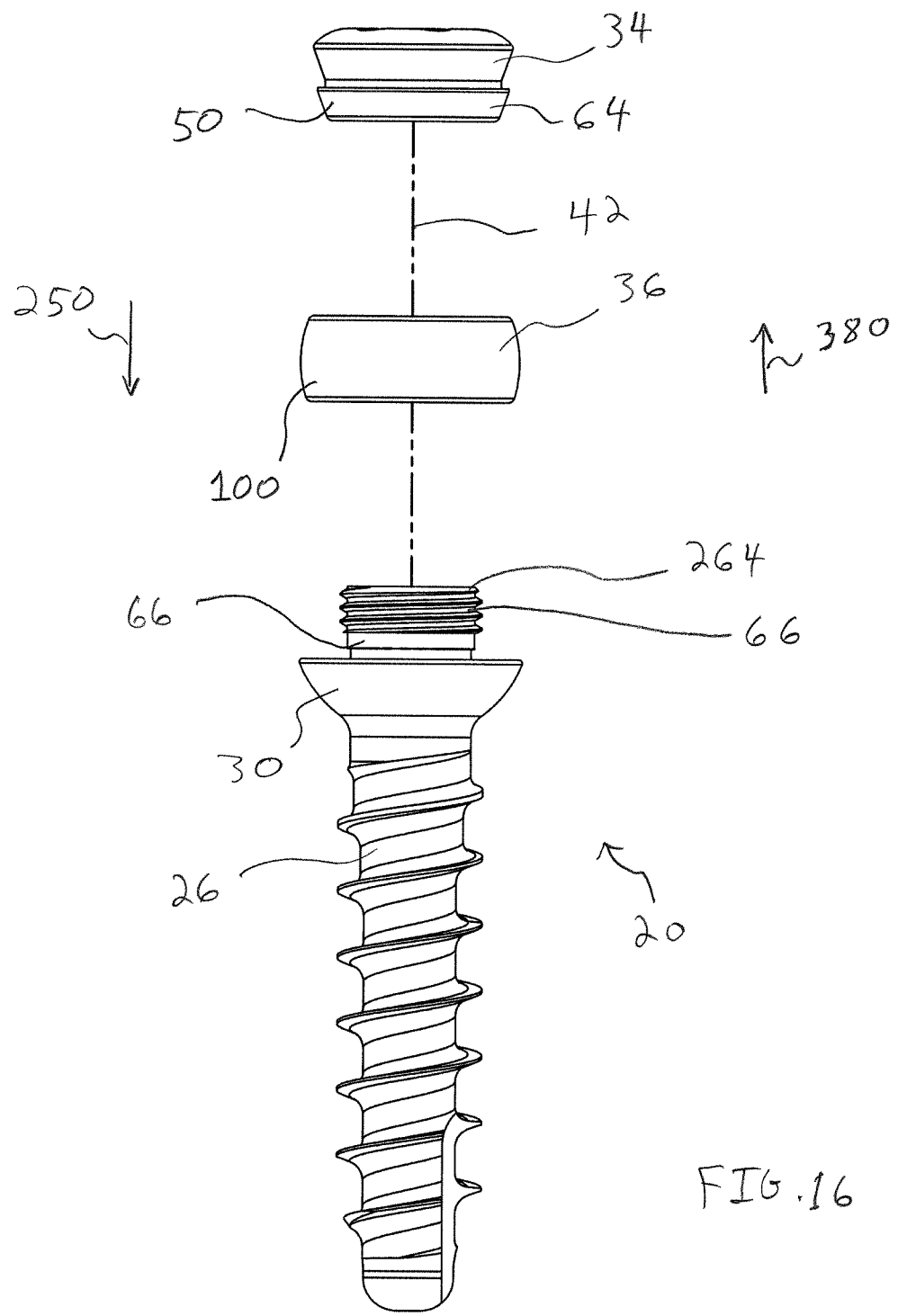
FIG. 16 is an exploded elevational view of one of the bone anchor assemblies of FIG. 1.

With reference to FIGS. 6, 7, and 16, the cap drive member 34 has a depending wall 64 extending about a portion of the bone screw head 30, such as screw head upstanding wall 66. The depending wall 64 of the cap drive member 34 is disposed radially between the bone screw wall 66 and the locking cap 36. The depending wall 64 and the bone screw wall 66 each have a generally tubular shape and are concentrically aligned when the cap drive member 34 is connected to the bone anchor head 30. Further, the locking cap 36 has a generally annular shape extending around the cap drive member 34 when the cap drive member 34 and the locking cap 36 are connected to the bone screw head 30. The concentric engagement of the bone screw wall 66, cap drive member depending wall 64, and locking cap 36 allows the cap drive member depending wall 64 to directly transfer loading exerted on the locking cap 36, such as loads from post-operative shifting of the vertebra, against the bone screw wall 66 without the use of thin, radially extending members as in some prior bone anchor assemblies. Further, the cap drive member depending wall 64 can directly transfer loading from the locking cap 36 to the bone screw wall 66 with substantially no deflection or other flexing of the cap drive member depending wall 64, which increases the strength of the engagement between the bone anchor assemblies 20, 24 and the bone plate 14.

The cap drive member 34 and locking cap 36 have engagement surfaces, such as cam surfaces 50, 52, configured to engage and expand the locking cap 36 with movement of the cap drive member 34 from an unlocked to a locked position, as shown in FIGS. 6 and 7. The cam surface 50 is disposed on a radially outer portion 55 (see FIG. 28) of the cap drive member depending wall 64 and the cam surface 52 is disposed on a radially inner portion 57 (see FIG. 24) of the locking cap 36 so that the cam surfaces 50, 52 engage about and radially outward from the bone screw wall 66. The bone screw head 30 may be substantially rigid, and positioning the cam surfaces 50, 52 about and radially outward from the bone screw head portion 66 permits the cap drive member 34 to expand the locking cap 36 without utilizing a weakened screw head as in some prior approaches.

Another advantage of the cam surfaces 50, 52 of the cap drive member 34 and locking cap 36 being disposed about and radially outward from the bone screw wall 66 is that the cam surfaces 50, 52 are positioned outside of a drive recess 71 of the bone screw head 30, as shown in FIGS. 6 and 7. The drive recess 71 is generally unobstructed by the cap drive member 34 and locking cap 36 so that the size of the drive recess 71 can be relatively large without reducing the strength of the cap drive member depending wall 64. Similarly, the bone screw upstanding wall 66 extending about the drive recess 71 can be relatively thick to further enhance the strength of the bone screw head 30 without compromising the strength of the locking cap depending wall 64. This approach stands in contrast to some prior bone screw assemblies, which utilize a c-ring having radially extending portions configured to contact a locking member. In these prior screw assemblies, increasing the size of a drive recess of the bone screw assembly required that the radially extending portions be lengthened or that the portions of the bone screw head surrounding the drive recesses be thinned, both of which reduce the strength of those prior bone screw assemblies.

With reference to FIG. 11, the resilient support member 16 may be moved in directions 48A, 48B along an axis 47 of the elongated throughbore 18 before the bone anchor assembly 20 is driven into the opening 53 and the cap drive member 34 shifted to the locked position. This adjustability allows a surgeon to position the support member 16 so that the opening 53 is adjacent a desired portion of an underlying bone. For example, the bone plate system 10 may be used to stabilize a pair of vertebrae 720, 722 with an implant 724 having a width 804 (see FIG. 46). If the implant width 804 is relatively large, the support member 16 may be moved in direction 48A in order to increase the distance between the support member opening 53 and non-elongated throughbore 22 and the resulting positioning of the bone anchors 20, 24. The support member 16 can be moved in direction 48A until the support member opening 53 is located adjacent the vertebra 722, for example, so that the bone anchor assembly 20 may be driven through the opening 53 and into an end plate of the vertebra. Conversely, if the implant 724 has a smaller width 804, the support member 16 may be moved in direction 48B to decrease the distance between the support member opening 53 and the non-elongated throughbore 22 and the resulting distance between the bone anchor assemblies 20, 24.

Figure 5:
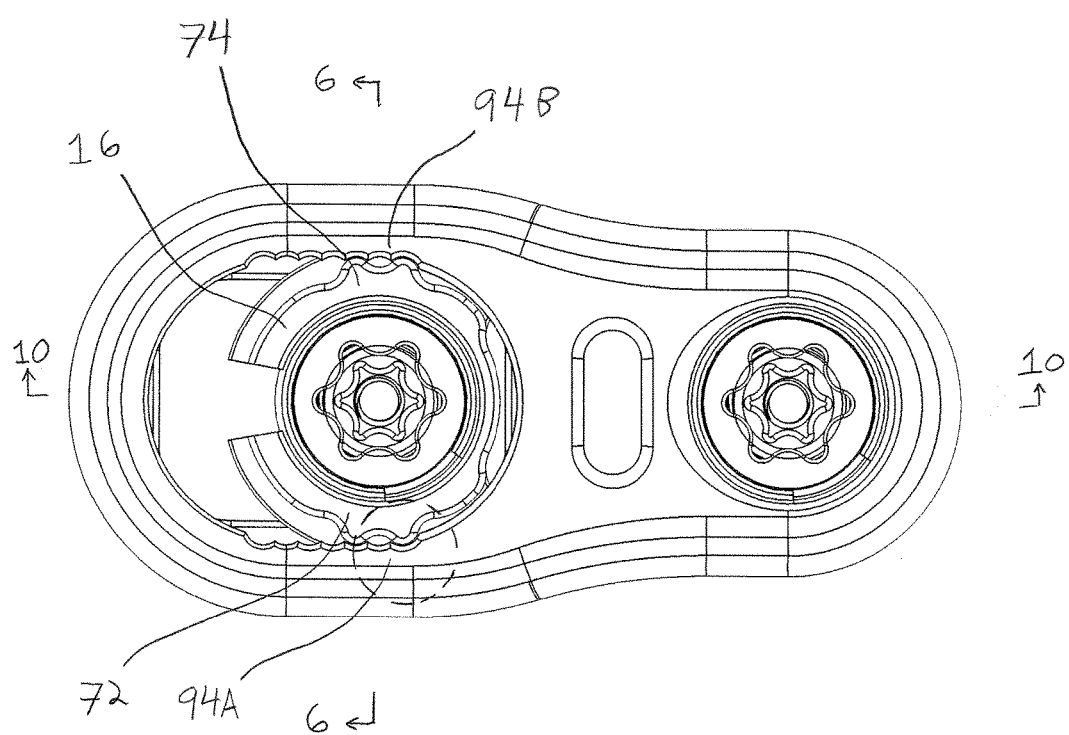
FIG. 5 is a top plan view of the bone plate system of FIG. 1 showing one of the bone anchor assemblies received in a resilient support member in an elongated throughbore of the bone plate and the other bone anchor assembly received in a non-elongated throughbore of the bone plate.
Figure 8:
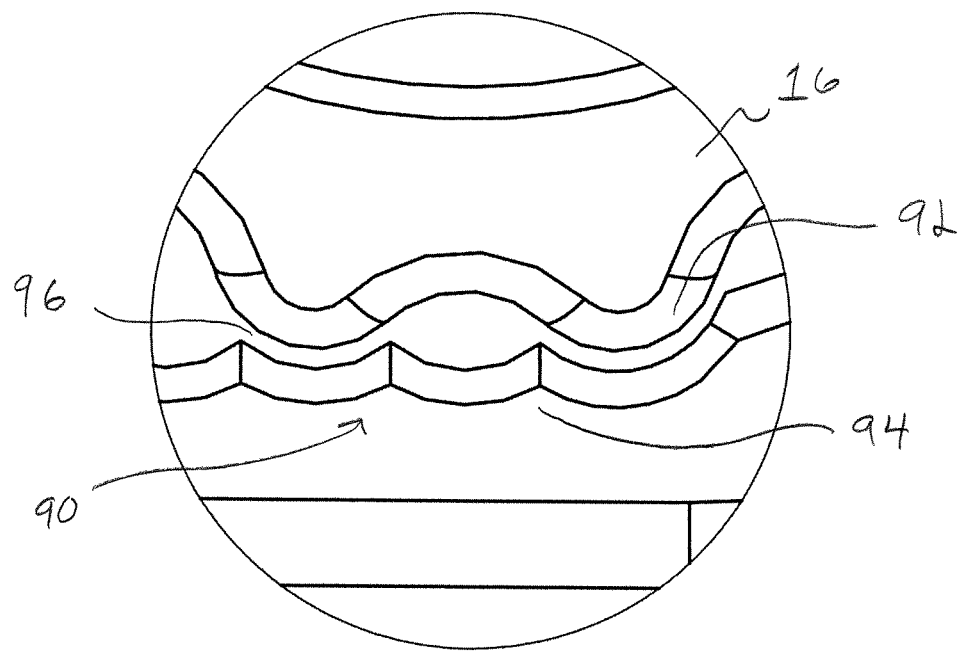
FIG. 8 is a partial, enlarged view of the area shown in the dashed circle of FIG. 5 showing projections of the resilient support member spaced from teeth of the bone plate before the cap drive member has been driven to the locked position.
Figure 9:
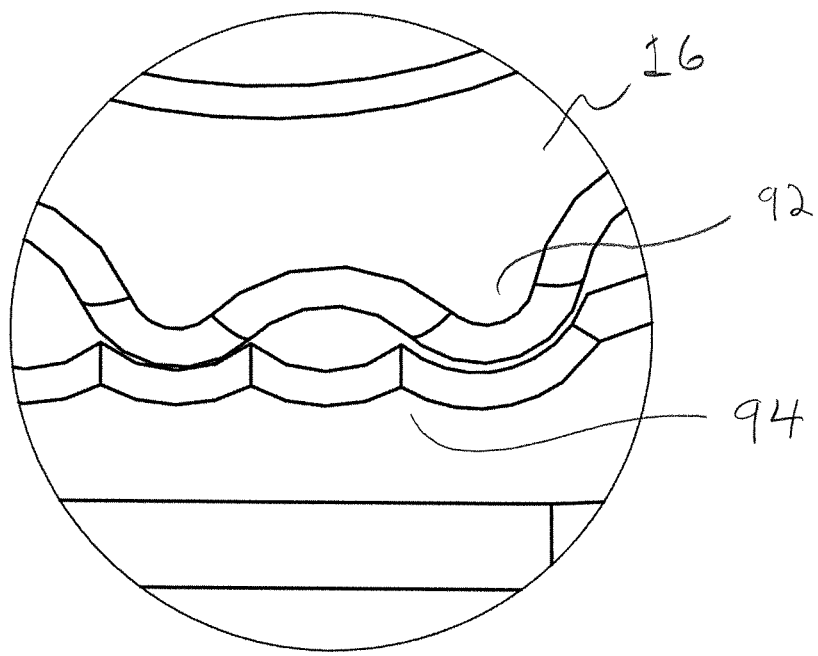
FIG. 9 is a partial, enlarged view similar to FIG. 8 showing the projections of the support member engaged with the teeth of the bone plate after the cap drive member of the bone anchor assembly has been driven to the locked position.

With the support member 16 in the desired location along the elongated throughbore 18, the bone anchor assembly 20 may be driven into the support member opening 53 and the position of the support member 16 and bone anchor assembly 20 may then be locked along the throughbore 18, as shown in FIGS. 5-7. More specifically, the resilient support member 16 has a pair of side portions 72, 74 on opposite sides of the opening 53 configured to be engaged by the resilient locking cap 36. The plate member 14 and support member 16 also have interfering portions 90, such as support member projections 92 and plate member teeth 94, configured to engage and limit movement of the support member 16 relative to the bone plate member 14, as shown in FIGS. 8 and 9. Shifting the cap drive member 34 of the bone anchor assembly 20 in direction 46 (see FIGS. 3 and 4) to the locked position expands the locking cap 36, presses a partially spherical outer surface 100 of the locking cap 36 against a pocket surface 103 of the support member 16, and shifts support member portions 72, 74 apart in directions 76, 78 toward throughbore walls 80, 82, as shown in FIGS. 6 and 7.

Expansion of the resilient support member 16 shifts the support member projections 92 and plate member teeth 94 from an adjustment orientation, where there is a gap spacing 96 between the projections 92 and teeth 94, into a locked orientation where the projections 92 and teeth 94 are engaged, as shown in FIGS. 8 and 9. The engaged projections 92 and teeth 94 restrict translational movement of the support member 16 and bone anchor assembly 20 received therein along the elongated throughbore 18. Thus, the support member projections 92 and bone plate teeth 94 can be quickly shifted from the adjustment orientation to the locked orientation to lock the position of the support member 16 and bone anchor assembly 20 simply by shifting the cap drive member 34 to the locked position after the bone screw head 30 has been seated in the opening 53. This easy-to-use location locking mechanism advantageously provides the bone anchor stability of a bone plate having static bone anchor locations as well as the installation flexibility of a bone plate having elongated throughbores. Further, the engaged projections 92 and teeth 94 may also restrict rotation of the support member 16 about the bone anchor longitudinal axis 46 within the throughbore 18 to increase the stability of the bone anchor 20 within the elongated throughbore 18.

In one form, the tolerances between the support member projections 92 and bone plate teeth 94 produce a slight ratcheting action when the projections 92 and teeth 94 are in the adjustment orientation and the support member 16 is moved along the elongated throughbore 18. The slight ratcheting action may be desirable in some applications to restrict the support member 16 from moving out of a desired position along the throughbore 18 before the bone anchor assembly 20 is driven into the support member opening 53 (see FIG. 48). In another form, the support member projections 92 and the bone plate teeth 94 may be in clearance with one another when they are in the adjustment orientation. The interfering portions of the support member 16 and the bone plate member 14 may have a variety of possible configurations. For example, the interfering portions may include one or more pins located on the support member 16 and one or more corresponding recesses on the bone plate member 14. In another approach, the interfering portions may include one or more tabs of the support member 16 and one or more corresponding slots on the bone plate member 14.

Figure 10:
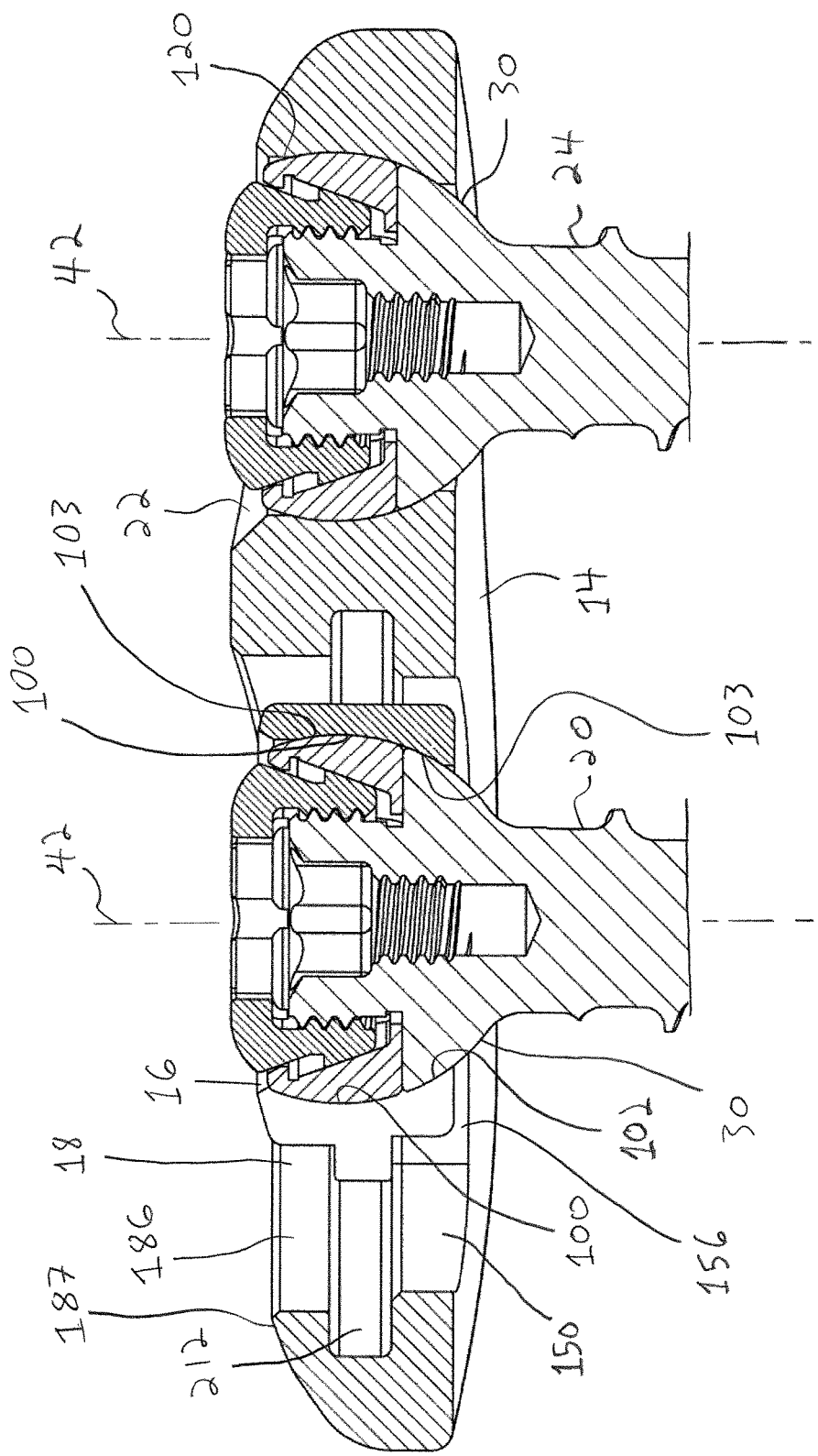
FIG. 10 is a cross-sectional view taken across line 10-10 in FIG. 5 showing generally spherical head portions of the bone anchor assemblies received in partially spherical pockets of the resilient support member and the non-elongated throughbore.

With reference to FIGS. 3 and 4, shifting the cap drive member 34 to the locked position shifts the partially spherical outer surface 100 of the locking cap 36 radially outward until the outer surface 100 is generally flush with a partially spherical lower surface 102 of the screw head 30. With the locking cap 36 in its expanded configuration, the surfaces 100, 102 form a larger, partially spherical outer surface 95 of a head portion of the bone anchor assembly 20. Further, the support member 16 has the partially spherical pocket surface 103 and the non-elongated throughbore 22 has a partially spherical pocket surface 120 each with a respective radius of curvature that is complimentary to the curvatures of the outer surfaces 100, 102 with the locking caps 36 in their expanded configurations, as shown in FIG. 10. The head portions 97 of the bone anchor assemblies 20, 24 thereby form a ball-and-socket connection between the bone anchor assemblies 20, 24 and the bone plate 12. The ball-and-socket connections permit a controlled pivoting of the bone anchor assemblies 20, 24 to accommodate post-operative movement of the bones.

With reference to FIGS. 6 and 7, driving the bone anchor 26 into the support member opening 53 also seats the screw head lower surface 102 against a seating portion 105 of the pocket surface 103 which can be used to lag the bone plate member 14 against a bone. Further, the engagement between the bone screw head lower surface 102 and the seating portion 105 of the pocket surface 103 provides a direction connection between the bone screw 26 and the bone plate 12. This direct connection increases the strength of the engagement between the bone screw 26 and the bone plate 12 and permits the bone screw 26 to directly transfer loading to the bone plate 12.

The cap drive member 34 is then shifted to the locked position which expands the locking cap 36 and brings the cap outer surface 100 into engagement with an engagement portion 107 of the pocket surface 103. Driving the cap drive member 34 into the locked position firmly engages the partially spherical outer surface 100 of the locking cap 36 with the engagement portion 107 of the pocket surface 103. Thus, with the screw head 30 seated in the support member opening 53 and the cap drive member 34 shifted to the locked position, both the cap outer surface 100 and the head lower surface 102 are frictionally engaged with the support member seating surface 103. This frictional engagement provides controlled resistance to pivoting movement of the bone anchor assembly 20 relative to the support member 16.

With reference to FIGS. 3 and 4, the bone anchor assembly head portion 97 has a height 99 along the bone anchor assembly longitudinal axis 42 and the locking cap partially spherical outer surface 100 has a height 101 that is approximately half the height 99 of the bone anchor assembly head portion 97. In some forms, the height 101 could be approximately a quarter of the height 99, approximately three-quarters of the height 99, or another proportion although the locking cap height 101 is preferably greater than a quarter of the head portion height 99 in order to preserve a sufficiently large partially spherical lower surface 102 of the bone screw head 30. The relatively large axial extent or height 101 of the locking cap outer surface 100 provides a large amount of surface area of the locking cap outer surface 100 which can engage the support member pocket surface 103. This increases the frictional engagement of the locking cap 36 with the support member 16 and limits pivoting of the bone anchor assembly 20 once the cap drive member 34 has been shifted to the locked position.

With reference to FIG. 10, the partially spherical seating surfaces 103 extends along the locking cap outer surfaces 100 substantially the entire length of the outer surface 100 along the longitudinal axis 42 of the bone anchor assembly 20. By extending substantially the entire axial extent of the locking cap outer surface 100, the frictional engagement between the locking cap outer surface 100 and the support member seating surface 103 can be maximized. For example, when the bone screw 20 undergoes pivoting (such as due to post-operative movement of bones) or when the bone anchor assembly 20 is driven obliquely into the opening 53 of the support member 16, there is still a majority of the locking cap outer surface 100 engaged with the support member pocket surface 103 despite the transverse orientation of the locking cap 36 relative to the support member 16. The partially spherical seating surface 120 of the non-elongated throughbore 22 is similar to the support member seating surface 103 and provides similar advantages in terms of engagement and controlled pivoting between the bone anchor assembly 24 and the plate member 14.

The materials of the bone screw 26, locking cap 36, and bone plate member 14 may be selected, in part, to provide a desired amount of frictional engagement between the bone anchor assembly 20 and the support member 16 which controls pivoting of the bone anchor 20. The surface texture of the surfaces 100, 102, 103, and 120 may also be configured to provide a desired amount of frictional engagement therebetween and resulting resistance to pivoting of the bone anchor assemblies 20, 24 relative to the bone plate 12. For example, the roughness of one or more of the surfaces 100, 102, 103, and 120 can be increased, such as by blasting, in order to increase the frictional engagement between the support member 16 and the bone anchor assembly 20 and increase resistance to pivoting of the bone anchor assembly 20.

Figure 12:
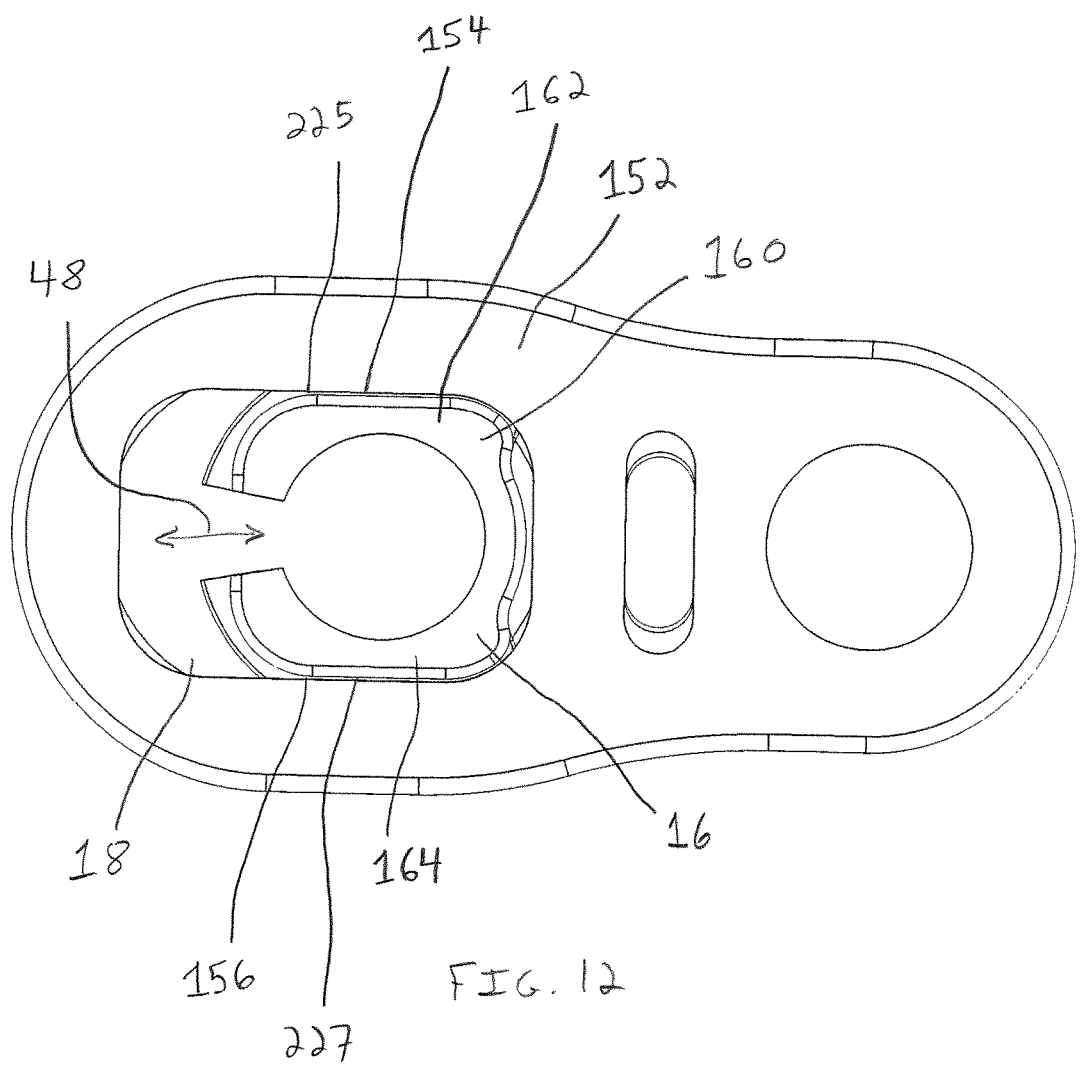
FIG. 12 is a bottom plan view of the bone plate of FIG. 1 showing a generally rectangular lower opening of the elongated throughbore and a generally rectangular lower portion of the support member fit within the lower opening of the elongated throughbore.
Figure 15:
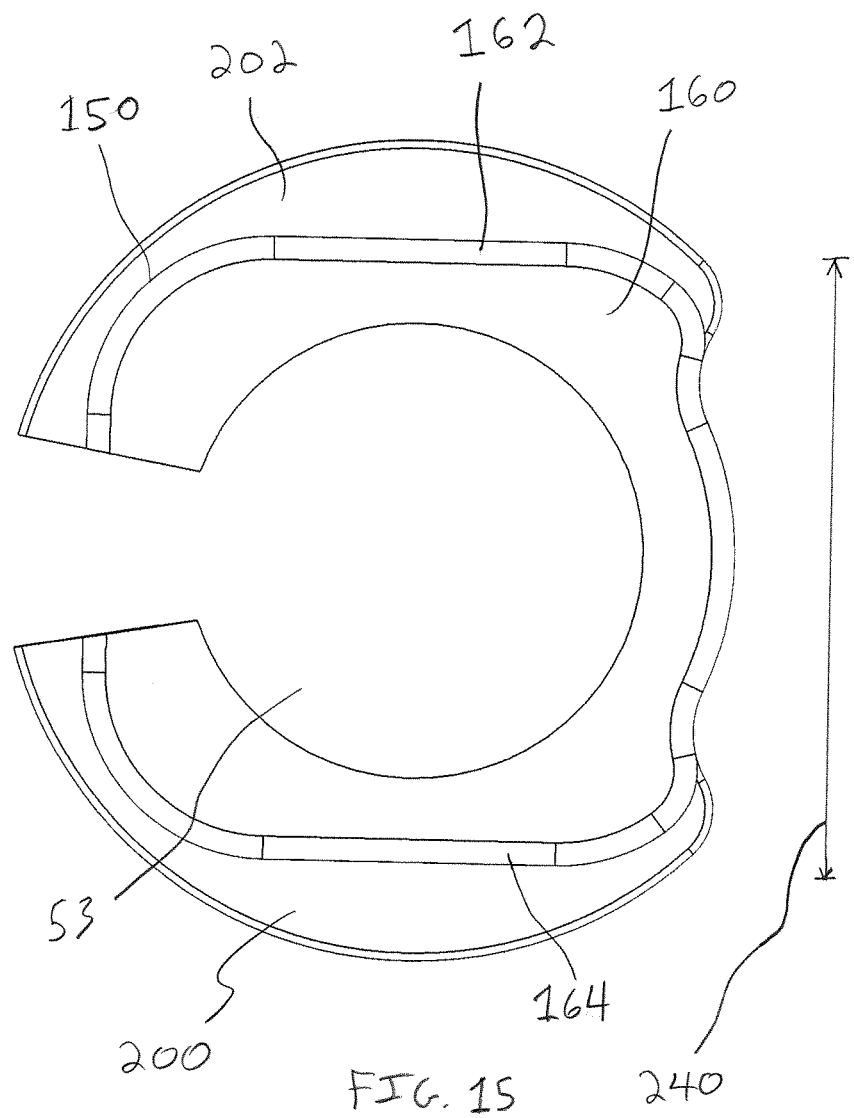
FIG. 15 is a bottom plan view of the support member of FIG. 13 showing the flange of the support member extending radially beyond the generally rectangular lower portion of the support member.

With reference to FIGS. 6, 12, and 15, the support member 16 and throughbore 18 have cooperating features configured to limit rotation of the support member 16 and generally restrict the support member 16 to movement along the axis 47 of the elongated throughbore 18. In one form, the throughbore 18 has a narrow section 150 near a bottom surface 152 of the bone plate member 14. The narrow section 150 includes flat guide surfaces 154, 156 on opposite sides have the throughbore 18 extending along the axis 46 of the throughbore 18. The support member 16 has a narrow lower portion 160 configured to fit within the throughbore narrow section 150 between the guide surfaces 154, 156. The support member lower portion 160 has a pair of lower walls 162, 164 configured to abut the guide surfaces 154, 156, as shown in FIGS. 12 and 15. The plate member lower walls 162, 164 engage the support member guide surfaces 154, 156 and resist rotary movement of the support member 16 within the throughbore 18. This further increases the stability of the construct of the bone plate member 14, support member 16, and bone anchor assembly 20.

Figure 13:
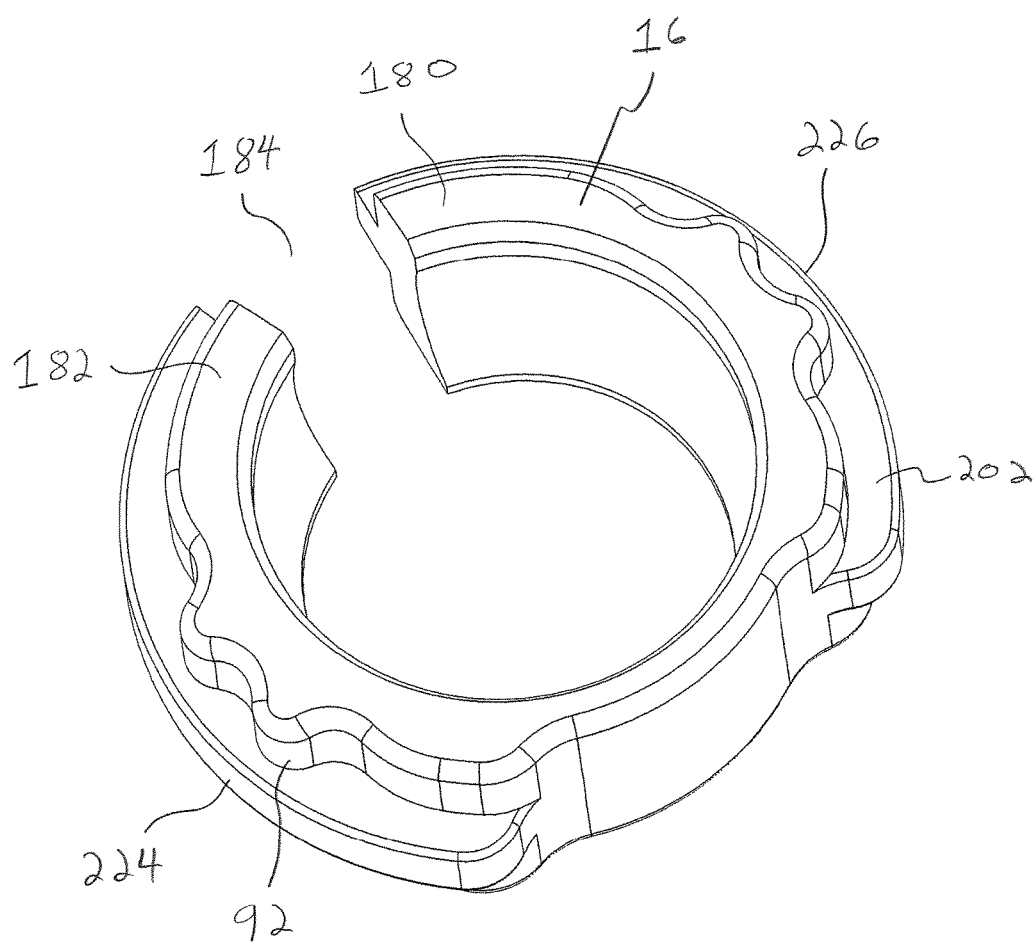
FIG. 13 is a perspective view of the resilient support member of the bone plate system of FIG. 1 showing a split-ring configuration of the support member.
Figure 14:
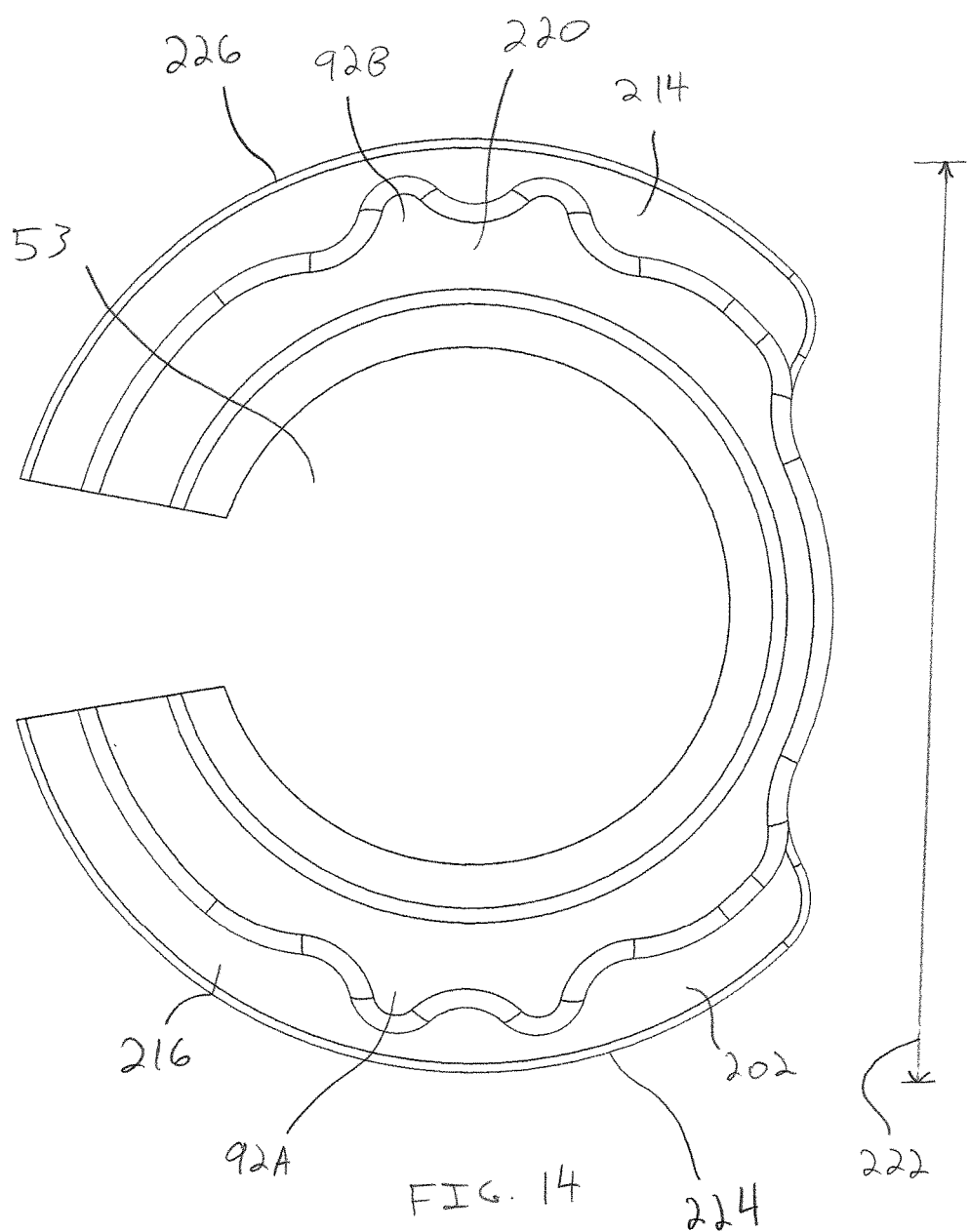
FIG. 14 is a top plan view of the support member of FIG. 13 showing the projections of the support member extending radially outward for engaging the teeth of the bone plate.

With reference to FIGS. 13-15, the support member 16 has a c-ring shape including a pair of opposed ends 180, 182 separated by a gap 184. The gap 184 permits the ends 180, 182 to move apart with radial expansion of the locking cap 36 due to shifting of the cap drive member 34 to the locked position (see FIGS. 6 and 7). The gap 184 also permits the support member 16 to be compressed, with ends 180, 182 shifting toward each other, during insertion of the support member 16 through an enlarged upper section 186 of the throughbore 18 adjacent an upper surface 187 of the plate member 14 (see FIGS. 10 and 11). The compressed support member 16 may be advanced into the throughbore 18 until a lower surface 200 of a flange 202 of the support member 16 contacts a lower support surface 204 of a channel 206 of the plate member 14, as shown in FIG. 6. The compressed support member 16 may then be released to permit the ends 180, 182 to expand apart and the flange 202 to shift outward into the channel 206. At this point, the resilient support member 16 is retained in the elongated throughbore 18 and may be shifted therealong as discussed above. The engagement between the support member flange 202 and the plate member channel 206 permits the bone anchor 20 to lag the bone plate 12 against a bone by seating the bone anchor 30 within the support member opening 53. Further, the engagement between the support member flange 202 and the plate member channel 206 transfers axial loading between the bone anchor 20 and bone plate 12 and restricts pull-through of the bone anchor assembly 20 out of the elongated throughbore 18.

The channel 206 includes sections 210, 212 on opposite sides of the throughbore 18 (see FIGS. 6 and 7) sized to receive corresponding portions 214, 216 of the support member flange 202 (see FIG. 14). The support member flange 202 has outer surfaces 224, 226 and the channel sections 210, 212 have guide surfaces 228, 230 which guide the support member 16 along the throughbore 18, as shown in FIG. 6. With reference to FIG. 14, the support member 16 has a body 220 with a width of 222 selected to permit the projections 92a, 92b to be in the adjustment orientation relative to the bone plate teeth 94a, 94b when the support member 16 is in the unexpanded configuration. The width 222 also provides a small amount of clearance between the flange outer surfaces 224, 226 and the channel guide surfaces 228, 230 which permits the support member 16 to be moved longitudinally within the elongated throughbore 18. With reference to FIGS. 12 and 15, the narrow section 150 of the support member 16 may have a width 240 between the support member lower walls 162, 164 which provides slight gaps 225, 227 between the walls 162, 164 and the plate member guide surfaces 154, 156. These gaps limit interference between the walls 162, 164 when the support member 16 is in the unexpanded and expanded configurations, although the gaps 162, 164 are smaller when the support member has been expanded. Limiting interference between the support member lower walls 162, 164 and the plate member guide surfaces 154, 156 may be desirable to ensure that the support member projections 92A, 92B fully engage the plate member teeth 94A, 94B despite variation in tolerances of the plate member 14, support member 16, and bone anchor assembly 20 during manufacturing.

Figure 48:
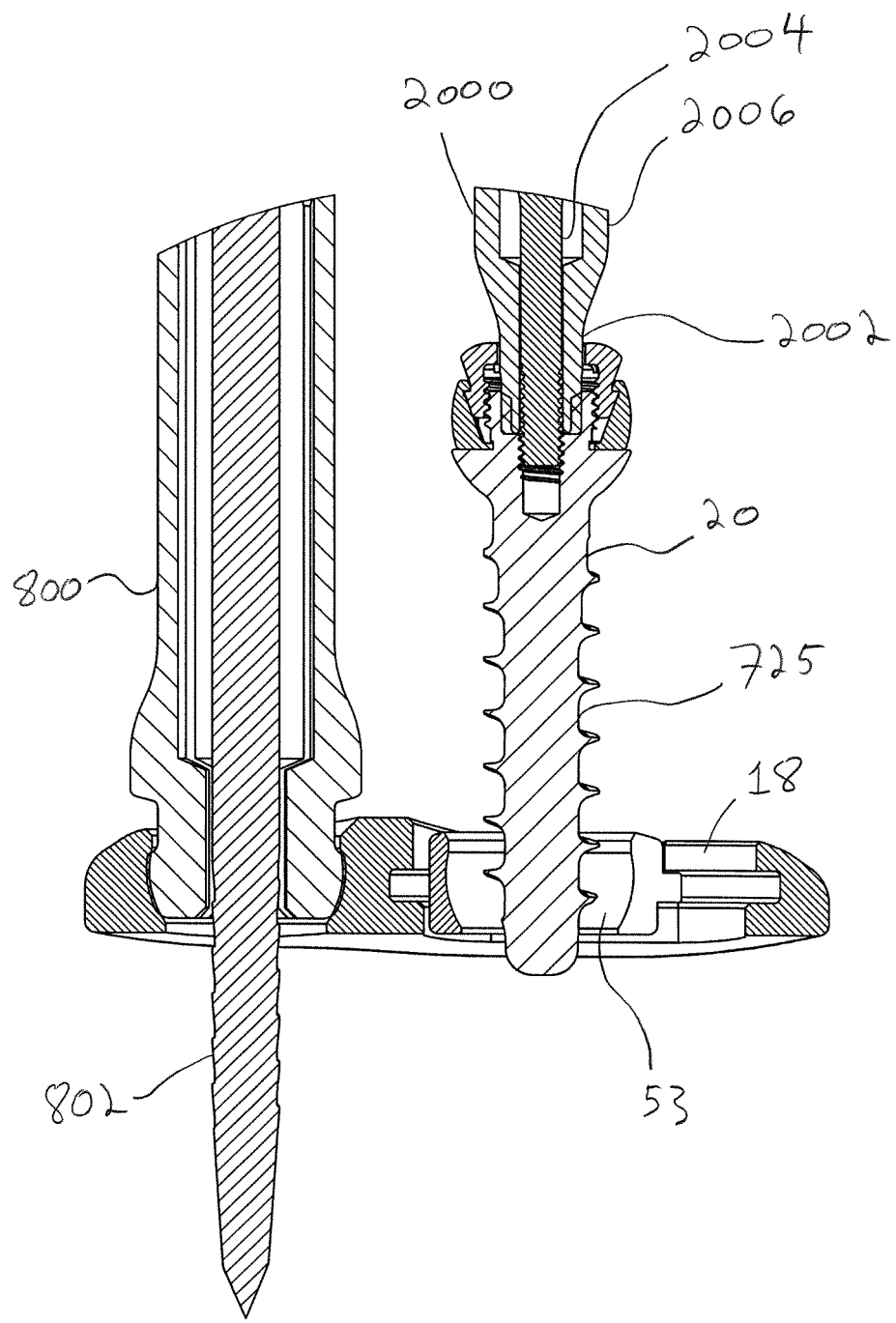

With reference to FIGS. 16-28, the bone anchor assembly 20 is described in greater detail. The bone screw head 30 has a partially spherical lower surface 102, a shoulder bearing surface 252 extending inward from the lower surface 102, and the wall 66 upstanding from the shoulder bearing surface 252. The upstanding wall 66 has a connection structure, such as threads 264, for connecting to the cap drive member 34. The upstanding wall 66 also includes the drive structure 71 for receiving a driving tool 2000, as shown in FIG. 48. In one form, the drive structure 71 includes a drive recess 280 for receiving a distal end of the driving tool, such as a socket, a hex socket, or a Phillips recess. For example, the drive recess 280 may be a T20 Torx drive to provide a firm engagement between the driving tool 2000 and the bone screw 26 during insertion and driving of the bone anchor assemblies 20, 24. The bone screw head 30 may also have a retention structure 282 configured to engage a retention portion of the driver tool 2000 and maintain the bone anchor assembly 20 on the driving tool 2000 until the bone anchor assembly 20 has been driven into bone. In one form, the retention structure 282 has threads 284 configured to engage threads of an internal retention shaft 2004 (see FIG. 48) of the driving tool 2000.

With reference to FIGS. 21-24, the locking cap 36 has an outer wall 310 with a split-ring configuration and engagement members 312 extending inwardly from the outer wall 310. The engagement members 312 have retention tips 314 sized to fit within a groove 270 extending around a base of the annular wall 66 (see FIGS. 17 and 20). The retention tips 314 have upper stop surfaces 316 that are positioned below a stop surface 272 of the bone screw groove 270 when the locking cap 36 has been assembled onto the screw head 30. The surfaces 272, 316 are in axial overlapping relation such that the surfaces 272, 316 contact and restrict removal of the locking cap 36 in direction 380 (see FIG. 16) once the locking cap 36 has been assembled onto the bone screw head 30.

Figure 24:
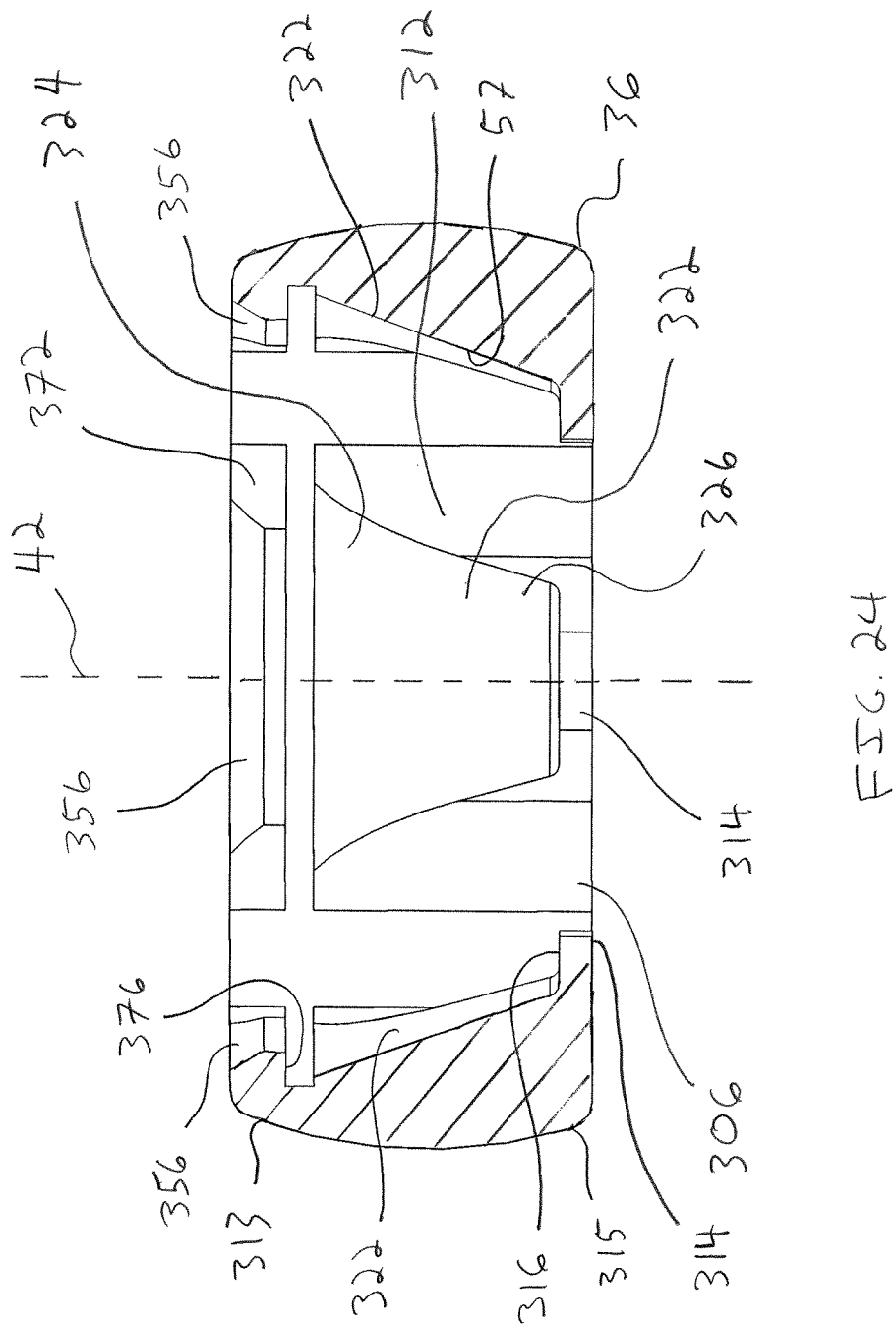
FIG. 24 is a cross-sectional view taken across line 24-24 in FIG. 22 showing radially inner inclined surfaces against which the cap drive member cams.

The locking cap engagement members 312 are generally wedge shaped and taper radially inward from an upper portion 313 adjacent the cap drive member 34 toward a lower portion 315 adjacent the shoulder bearing surface 252 of the bone screw head 30, as shown in FIG. 24. The locking cap 36 has cutouts 320 between each of the cam members 312 that define the general wedge shape of each engagement member 312 and increase the flexibility of the locking cap 36, as shown in FIG. 22.

With reference to FIGS. 23 and 24, the locking cap engagement surface 52 includes a cam surface 322 on each of the engagement members 312 that extends obliquely relative to the bone anchor longitudinal axis 46. The cam surface 322 may extend a majority of the height of the locking cap 36 along the anchor axis 46 and taper from a wider upper portion 324 to a narrow lower portion 326 to produce a relatively large amount of area for the cam surface 322 of each engagement member 312. This increases the overall cam surface area of the locking cap 36 and improves the ease with which the locking cap 32 may expand the locking cap 36. Further, the tapered shape of the cam surface 322 provides a surface for contacting the cap drive member engagement surface 50 while preserving the general wedge-shape of the engagement members 312 which improves the flexibility of the locking cap 36. The cam surface 322 also extends radially inward toward the bone screw upstanding wall 66 which permits the cap drive member engagement surface 50 to engage the cam surfaces 322 even as the locking cap 36 expands away from the upstanding wall 66 as the cap drive member 34 reaches its locked position.

Figure 51:
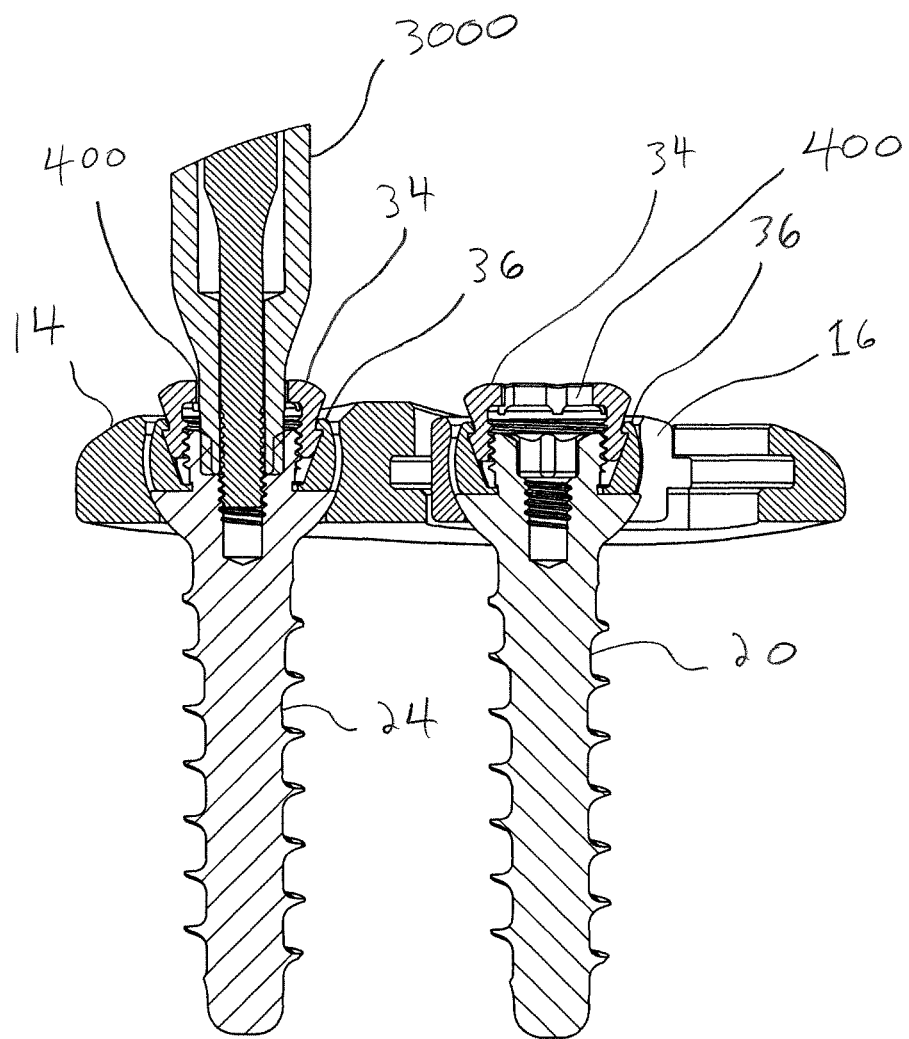
Figure 52:
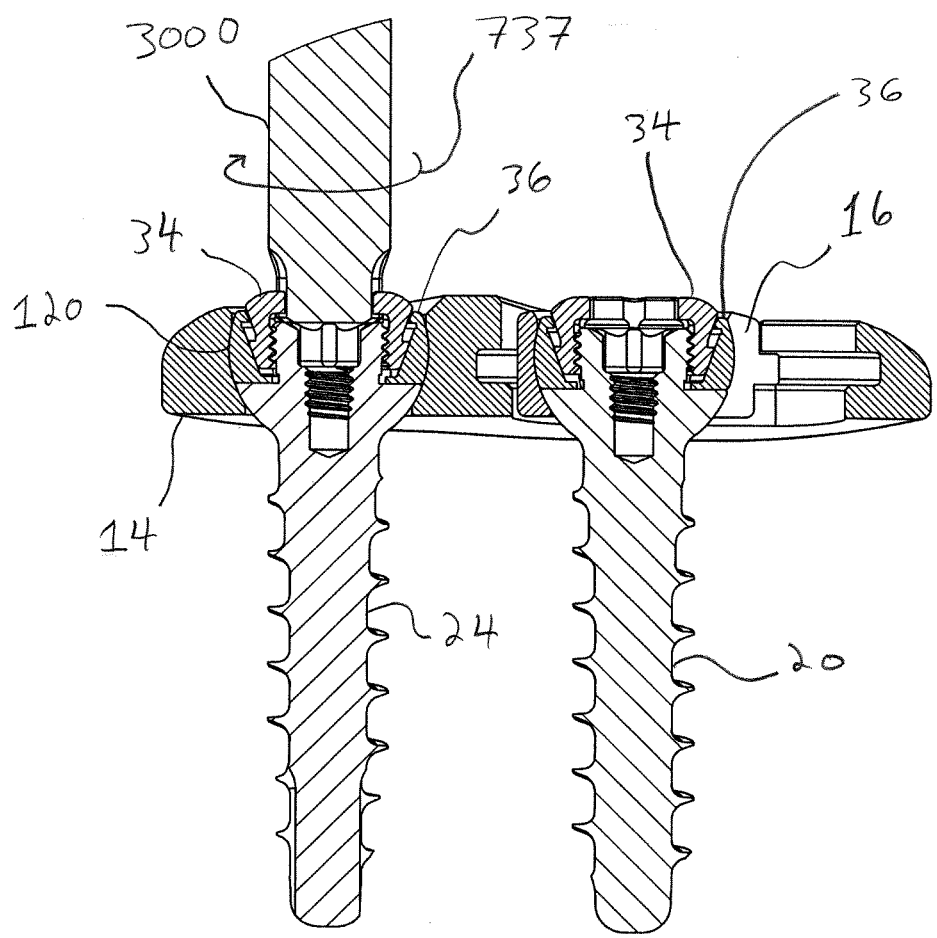
Figure 53:
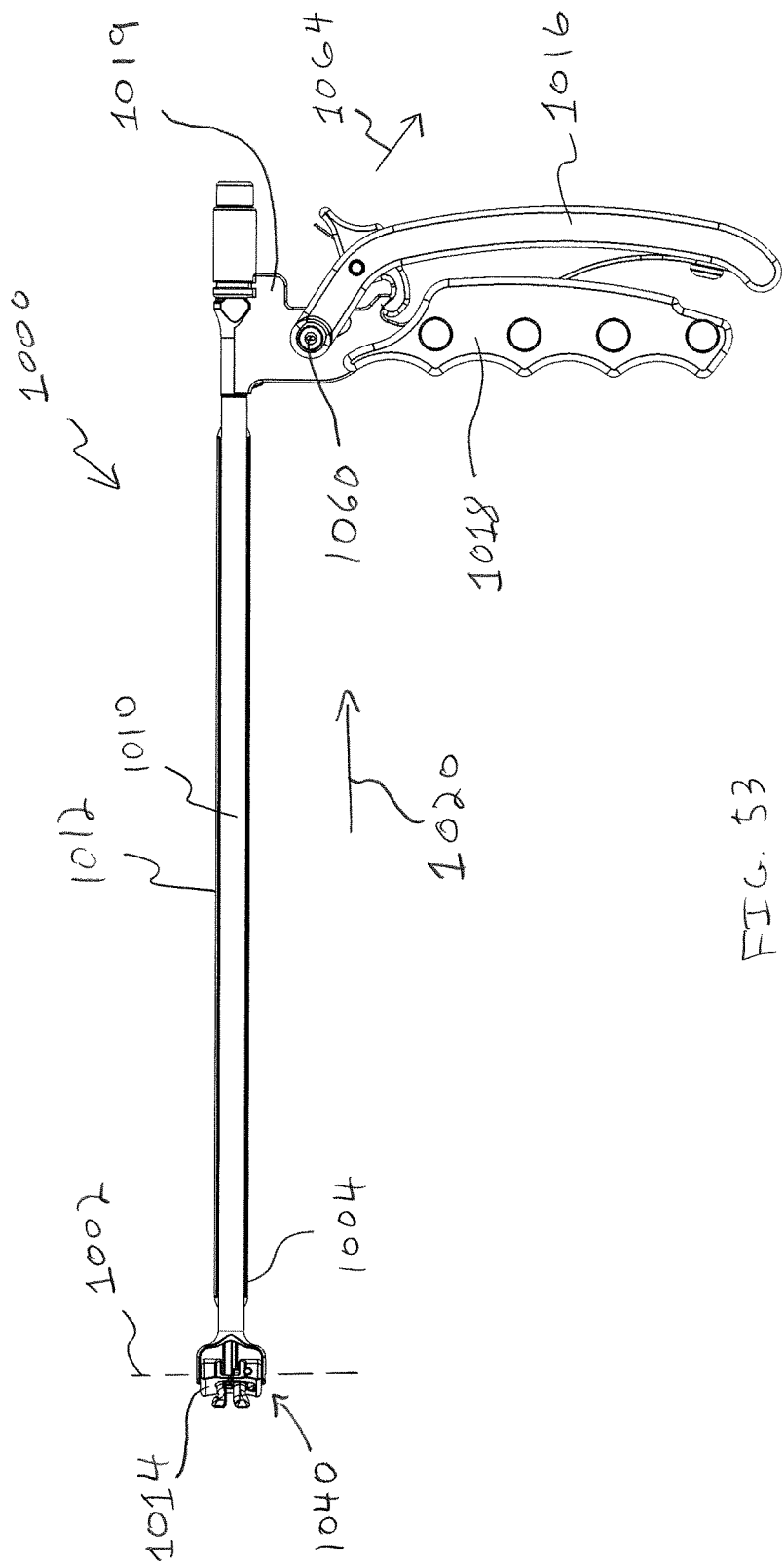
FIG. 53 is a left side elevational view of another inserter tool configured to be used to insert the bone plate of FIG. 1 during surgery.

With reference to FIGS. 25-28, the cap drive member 34 has an upper drive portion 401 with a through opening, such as an upper locking recess 400, sized to receive both the driving tool 2000 (see FIG. 49) and a distal end 3000 of a final tightener 3002 (see FIG. 51). However, the cap drive member 34 has a locking structure 402 configured to engage the final tightener 3002. In one form, the locking structure 402 is a T30 Torx socket, which is larger than a T20 Torx socket of the bone screw drive structure 71. The cap drive member 34 thereby permits a first tool to be used to drive the bone anchor assemblies 20, 24 into bones, and a different, second tool to be used to perform final locking of the bone anchor assemblies 20, 24 to the bone plate 12.

In one form, the cap drive member 34 has a lower end portion 403 and the engagement surface 50 includes a cam surface 404 that extends about the lower end portion 403 inwardly and obliquely relative to the bone anchor longitudinal axis 46. The lower end portion 403 of the cap drive member 34 thereby acts as a wedge to expand the locking cap 36 as the cap drive member 34 is driven to the locked position. The cam surface 404 is disposed radially outward on the cap drive member 34 and has a large surface area due to the diameter of the cap drive member 34. The large surface areas of the cap drive member cam surface 404 and locking cap cam surfaces 322 improve force transfer between the cap drive member 34 and the locking cap 36. Further, the large surface areas of the cap drive member cam surface 404 and locking cap cam surfaces 322 increase the frictional engagement between the cap drive member 34 and locking cap 36 which restricts movement of the cap drive member 34 away from the locked position.

In one form, the cam surface 404 is annular and continuous about the cap drive member 34 which permits the cam surface 404 to remain engaged with the cam surfaces 322 of the locking cap 36 as the drive member 34 is rotatably driven to the locked position.

The cap drive member 34 and locking cap 36 are generally assembled in a direction 250 onto the screw head 30 along the longitudinal axis 42 of the bone anchor assembly 20, as shown in FIG. 16. The locking cap 36 is positioned on the shoulder bearing surface 252 (see FIG. 19) of the screw head 30. Positioning the locking cap 36 onto the bearing surface 252 of the bone screw head 30 may include expanding the locking cap 36 by moving ends 300, 302 thereof apart to enlarge a gap spacing 304 therebetween (see FIG. 22). The locking cap 36 may then be moved axially downwardly onto the bone screw head 30 with the upstanding wall 66 passing into a lower opening 306 of the locking cap 36 (see FIG. 24).

Next, the lower end portion 403 of the cap drive member 34 is advanced into a central opening 354 (see FIG. 23) of the locking cap 36. The locking cap 36 has retention ribs 372 disposed above the engagement members 312 with guide surfaces 356 thereon. Advancing the cap drive member lower portion 403 into the locking cap central opening 354 brings the cap drive member cam surface 404 into contact with tapered guide surfaces 356 of the locking cap retention ribs 372. Continued axial movement of the cap drive member 34 toward the bone screw head 30 causes the cap drive member cam surface 404 to bear against the locking cap guide surfaces 356. This partially expands the locking cap 36 and permits a shoulder 470 of the cap drive member 34 (see FIG. 28) to travel axially beyond the retention ribs 372 of the locking cap 36.

Figure 28:
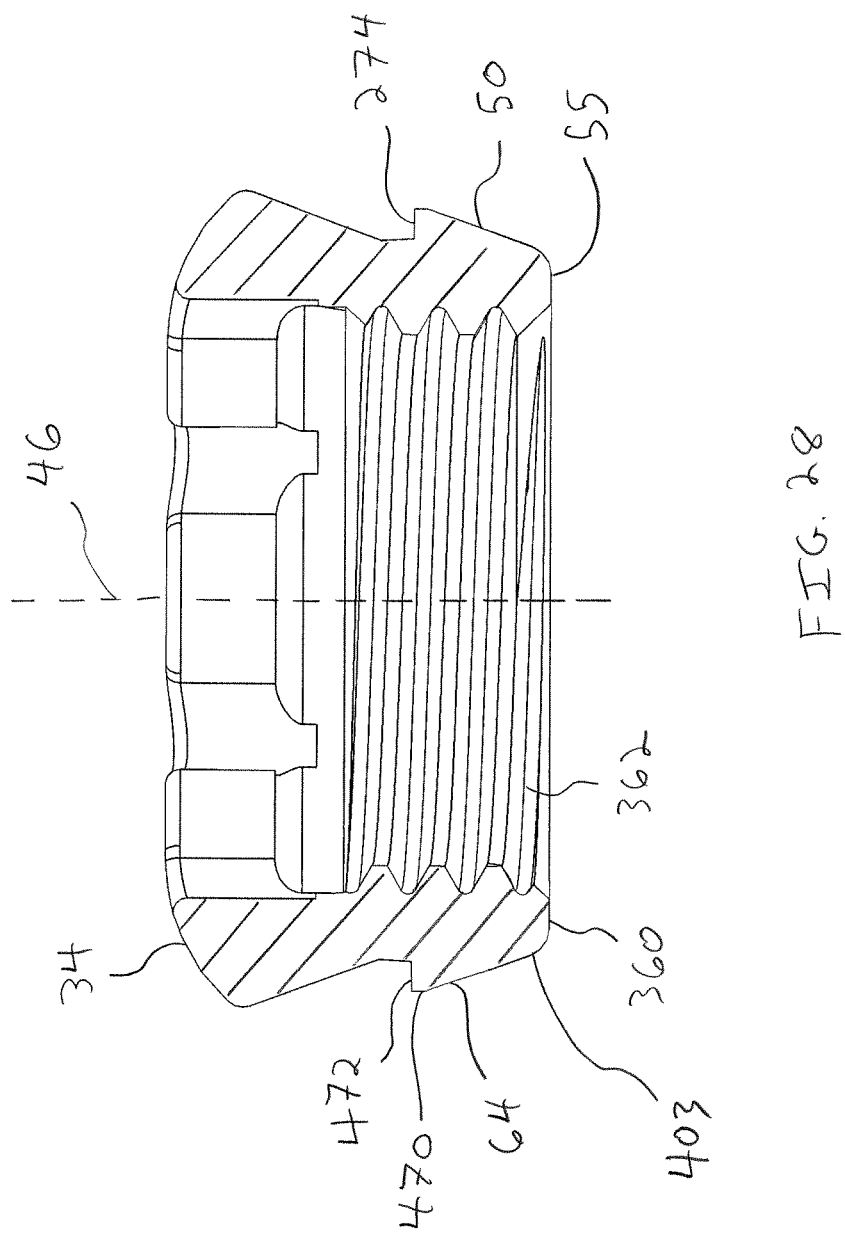
FIG. 28 is a cross-sectional view taken along line 28-28 in FIG. 26 showing an outer profile of the cap drive member.

Once the cap drive member shoulder 470 has passed beyond the locking cap retention ribs 372, the shoulder 470 has a flat annular stop surface 472 that is positioned below stop surfaces 376 on the undersides of the retention ribs 372 of the locking cap 36, as shown in FIGS. 24 and 28. At this point, the stop surfaces 376, 472 are in an axially overlapping and confronting orientation which restricts removal of the cap drive member 34 from within the locking cap 36 in direction 380 (see FIG. 6). Thus, the stop surfaces 272, 316 and 376, 472 of the bone anchor 26, cap drive member 34, and locking cap 36 maintain the cap drive member 34 and locking cap 36 on the bone screw head 30 and keep the bone anchors 20, 24 in the preassembled configuration.

The components of the bone plate system 10 may be made of biocompatible materials, such as stainless steels, titanium or titanium alloys, or other metals or alloys. The components of the bone plate 10 may also be made of one or more polymers, such as polyether ether ketone (PEEK).

With reference to FIGS. 29-43, an inserter tool 500 is provided for inserting the bone plate 12 into a confined surgical environment and positioning the bone plate 12 near one or more bones. The inserter tool 500 has a distal end portion 502 configured to releaseably connect to the bone plate 12 and a proximal end portion 504 with a gripable handle 506. The inserter tool 500 has a pivot mechanism 507 configured to selectively pivot the bone plate 12, the pivot mechanism 507 having an insertion configuration where a longitudinal axis 530 the bone plate 12 is oriented generally parallel to a longitudinal axis 532 of a shaft 509 of the inserter tool 500 (see FIGS. 29 and 29A) and a positioning configuration where the axis 530 of the bone plate 12 is generally perpendicular to the shaft axis 532 (see FIGS. 32 and 32A). With the pivot mechanism 507 in the insertion configuration, the inserter tool distal end portion 502 and the plate member 12 connected thereto are relatively compact, particularly in a lateral direction transverse to the shaft axis 532, and can be advanced through a surgical channel having a smaller cross-section than if the bone plate 12 was extending perpendicular to the shaft axis 532. The relatively compact configuration of the tool distal end portion 502 and plate member 12 can be seen, for example, by comparing a leading end width 531 of the distal end portion 502 and plate member 12 when the pivot mechanism 507 is in the insertion configuration (see FIG. 29A) to a leading end width 533 when the pivot mechanism 507 is in the positioning configuration (see FIG. 32A). Because the leading end width 531 is smaller than the width 533, the inserter tool distal end portion 502 and plate member 12 may be advanced through a smaller working channel when the pivot mechanism 507 is in the insertion configuration than if the pivot mechanism 507 were in the placement configuration. Thus, the pivot mechanism 507 enables the inserter tool 500 to be used in more tightly confined environments and provides a significant improvement over inserter tools that can grasp an implant in only a perpendicular orientation.

Figure 32:
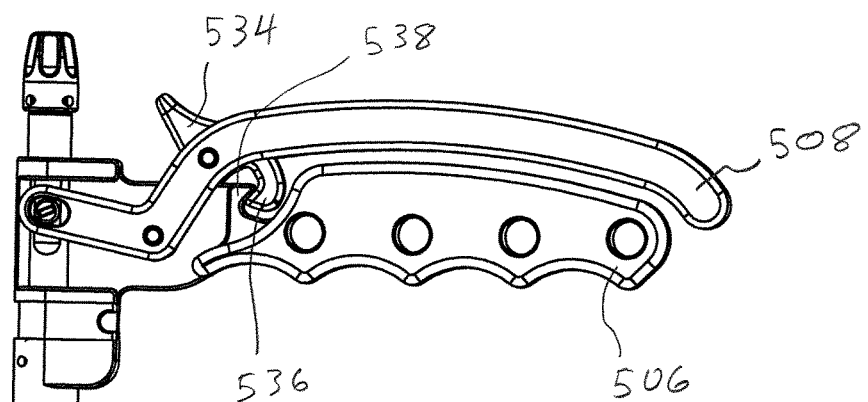
FIG. 32 is an elevational view similar to FIG. 29 showing a lever of the tool moved toward a handle of the tool which causes the inserter tool to pivot the bone plate.
Figure 33:
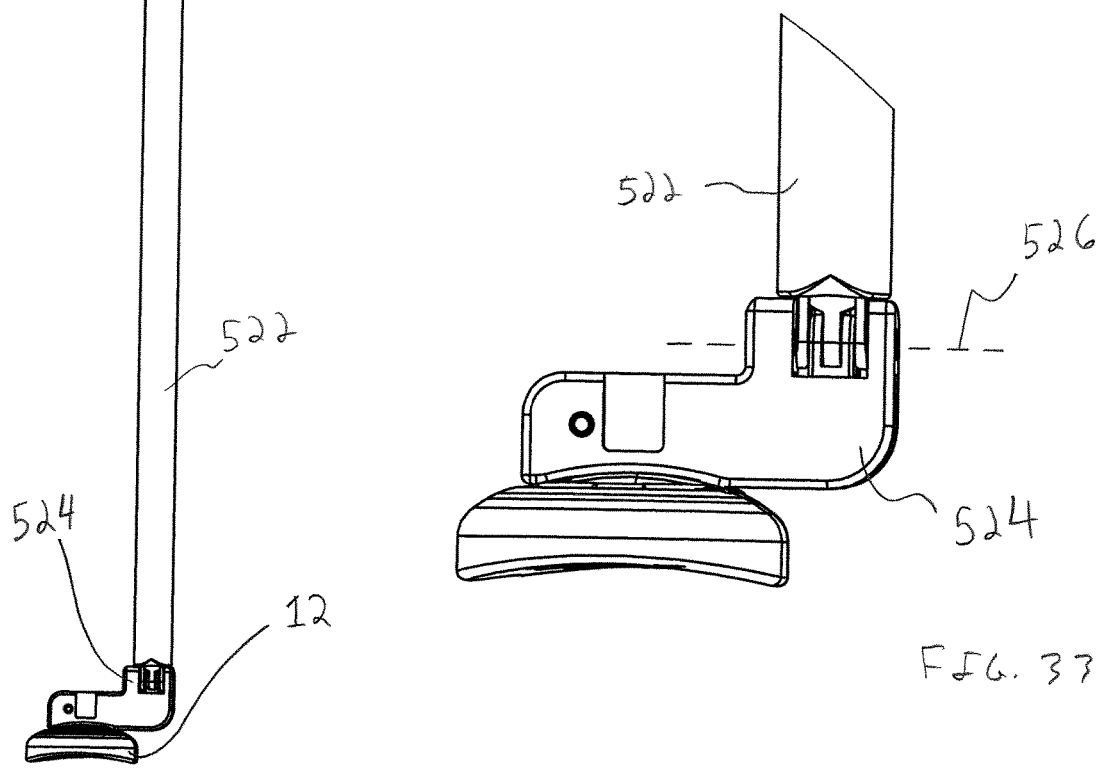
FIG. 33 is an enlarged partial view of the distal end of the inserter tool of FIG. 32 showing the distal end connected to the bone plate.

Once the inserter tool distal end portion 502 and bone plate 12 reach the surgical site, the pivot mechanism 507 can be shifted and reconfigured to the positioning configuration where the bone plate 12 is generally perpendicular to the shaft 509, as shown in FIGS. 32 and 32A. With the bone plate 12 generally perpendicular to the shaft 509, the handle 506 can be manipulated to move the bone plate 12 within the surgical site and position the bone plate 12 at a desired location on one or more bones (see FIGS. 45 and 46). In this manner, the inserter tool 500 provides improved ability to advance elongate implants, such as the bone plate 12, through a small working channel and then pivot the implant relative to the inserter tool 500 and permit placement of the implant on one or more bones.

Figure 29:
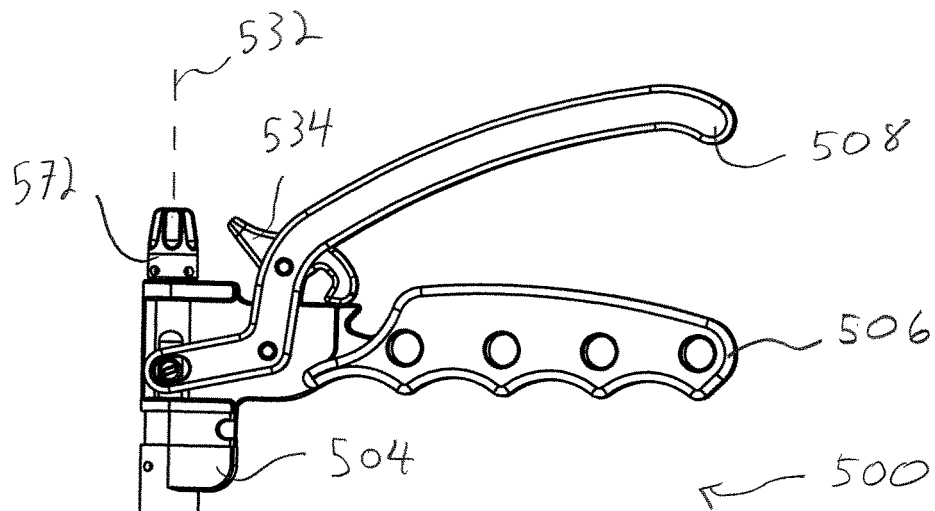
FIG. 29 is an elevational view of an inserter tool configured to be used to insert the bone plate of FIG. 1 during surgery.
Figure 30:
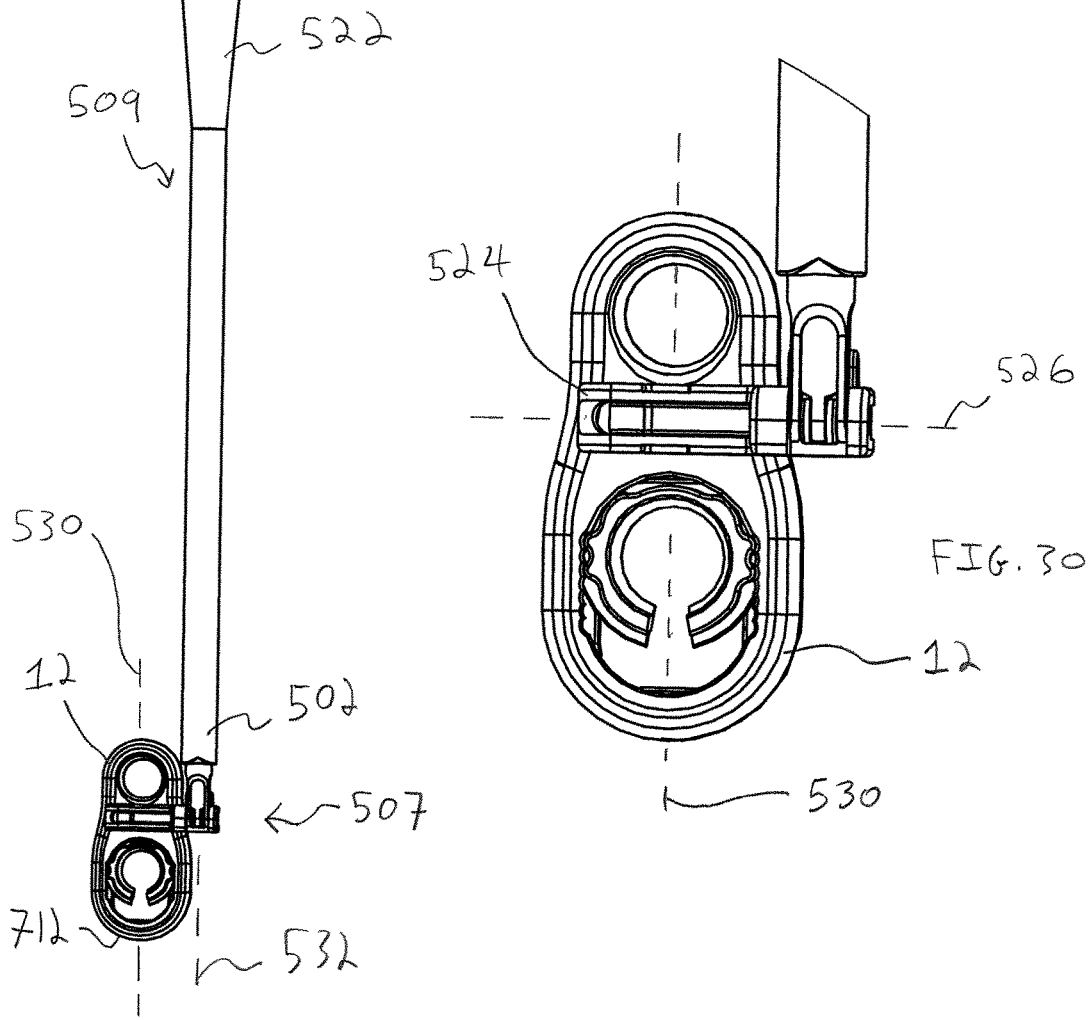
FIG. 30 is an enlarged partial view of a distal end of the inserter tool of FIG. 29 showing the distal end connected to the bone plate.
Figure 29A:
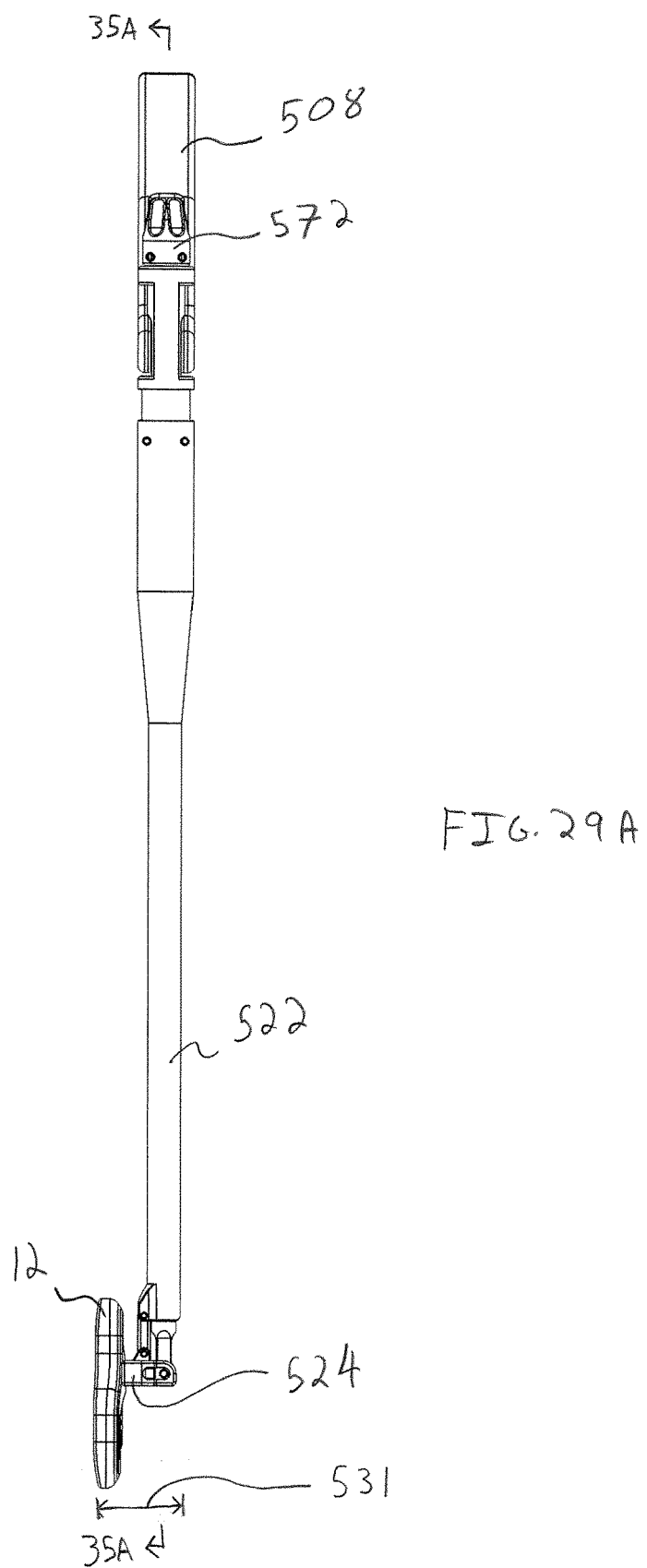
FIG. 29A is a top plan view of the inserter tool of FIG. 29 showing the bone plate in a generally parallel orientation relative to a shaft of the inserter tool.
Figure 31:
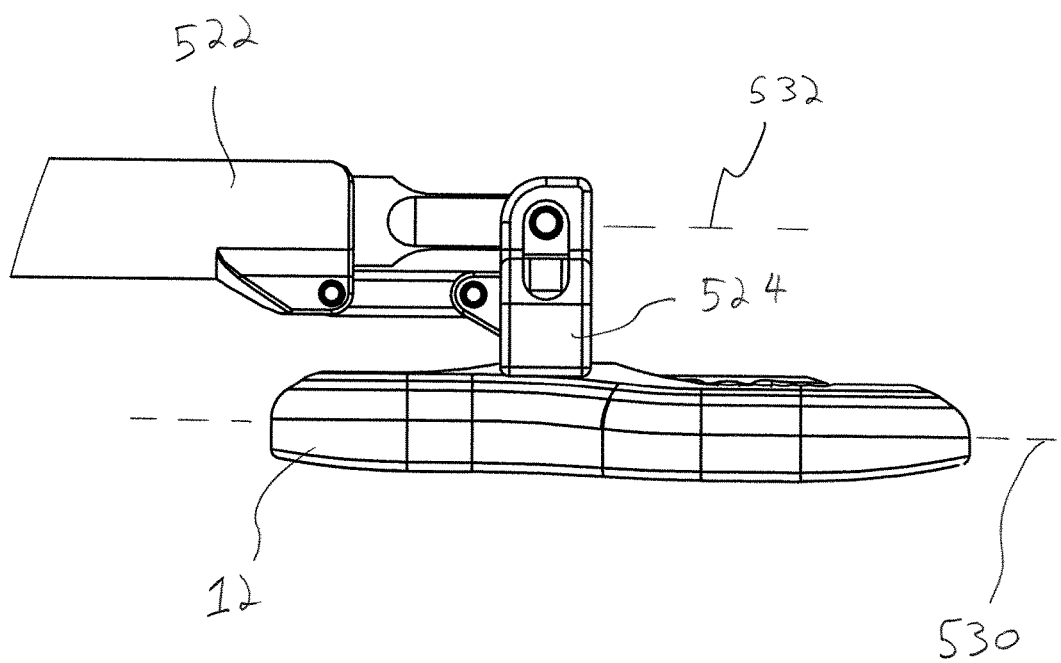
FIG. 31 is an enlarged elevational view of the distal end of the inserter tool of FIG. 29 showing a linkage between the shaft and a pivot body of the inserter tool which is connected to the bone plate.
Figure 34:
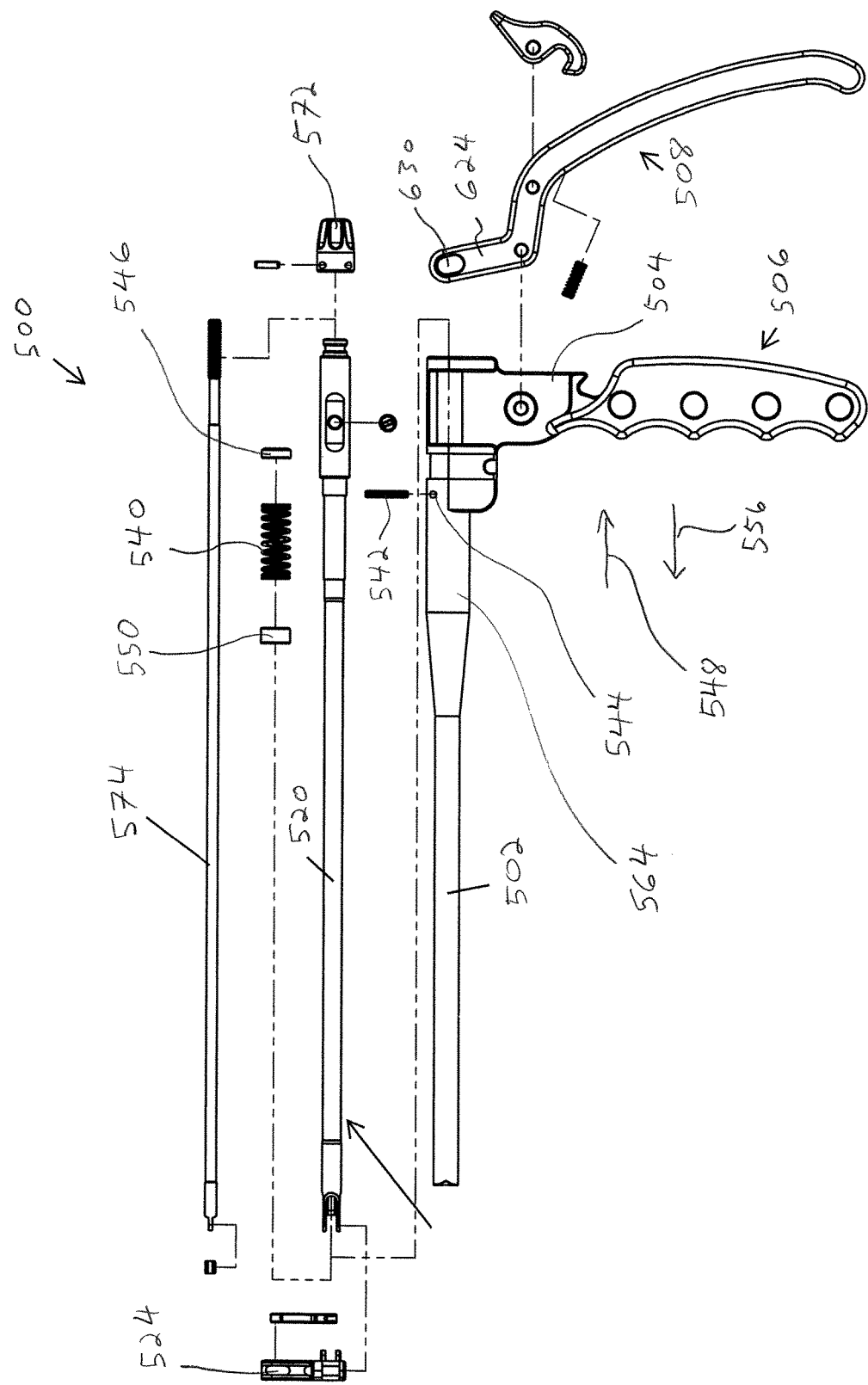
FIG. 34 is an exploded schematic view of the inserter tool of FIG. 29 showing a body shaft, a pivot shaft, and a grip control shaft of the inserter tool.

With reference to FIGS. 29 and 34, the inserter tool shaft 509 includes an outer body shaft 522, an intermediate pivot sleeve 520, and an inner grip control shaft 574. The pivot mechanism 507 includes the handle 508, the pivot sleeve 520, and a pivot body 524 connected to a distal end of the body shaft 522. Moving or compressing the lever 508 toward the handle to a closed position causes the pivot sleeve 520 to slide proximally within the body shaft 522 and pivot the pivot body 524 approximately 90 degrees about a pivot axis 526, as shown in FIGS. 29, 32, 35A, and 35B. The bone plate 12 is connected to the pivot body 524, such that pivoting of the pivot body 524 due to compressing the lever 508 causes the bone plate 12 to pivot relative to the inserter tool shaft 509. More specifically, compressing the lever 508 causes the bone plate 12 to move from an insertion orientation where a longitudinal axis 530 of the bone plate 12 is generally parallel with a longitudinal axis 532 of the shaft 509 to a positioning orientation where the bone plate longitudinal axis 530 is generally perpendicular to the shaft axis 532. The inserter tool 500 has a latch 534 with a hook 536 which may be pivoted to an engaged position where the hook 536 engages a tooth 538 of the handle 506. This allows the surgeon to easily maintain the bone plate 12 in the positioning orientation while performing other steps of the surgery, as will be discussed in greater detail below. Further, the latch 534 may be biased to the engagement position by a spring to restrict the latch 534 from being inadvertently disengaged.

Figure 35A:
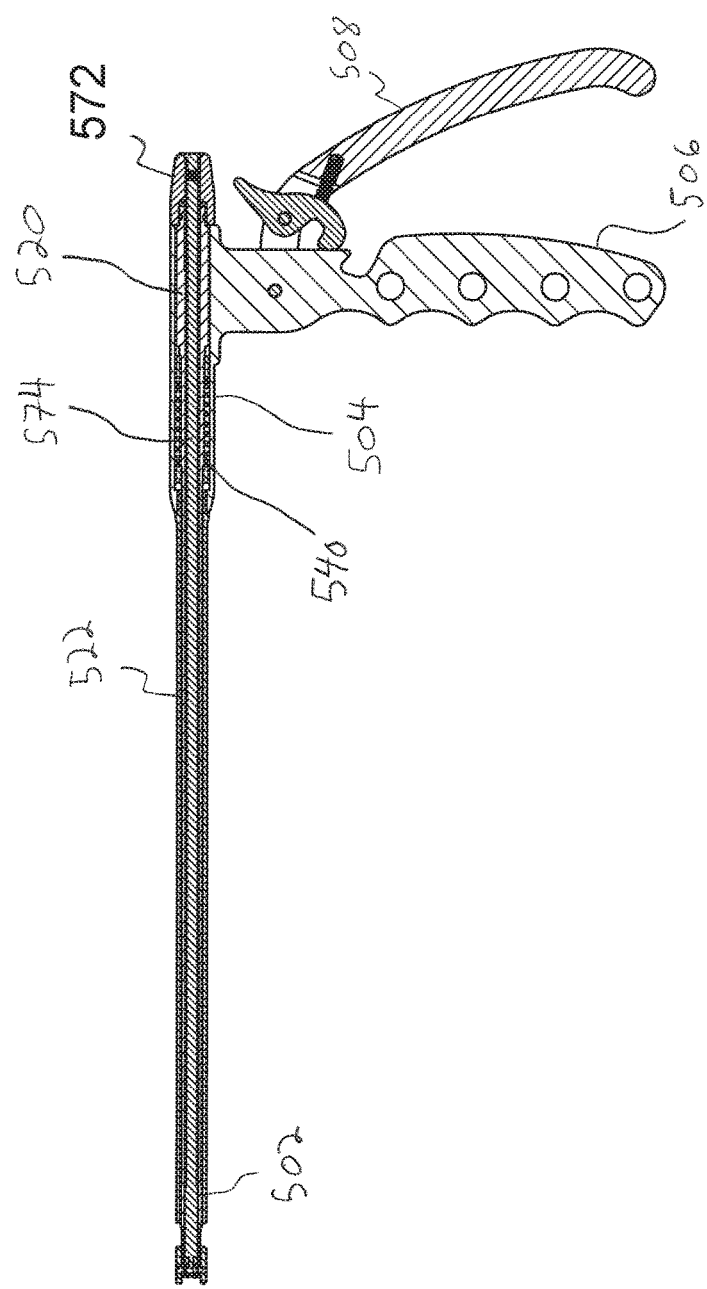
FIG. 35A is a cross-sectional view of the inserter tool taken across line 35A-35A in FIG. 29A showing the lever in the open position and a pivot shaft of the inverter tool shifted distally.
Figure 35B:
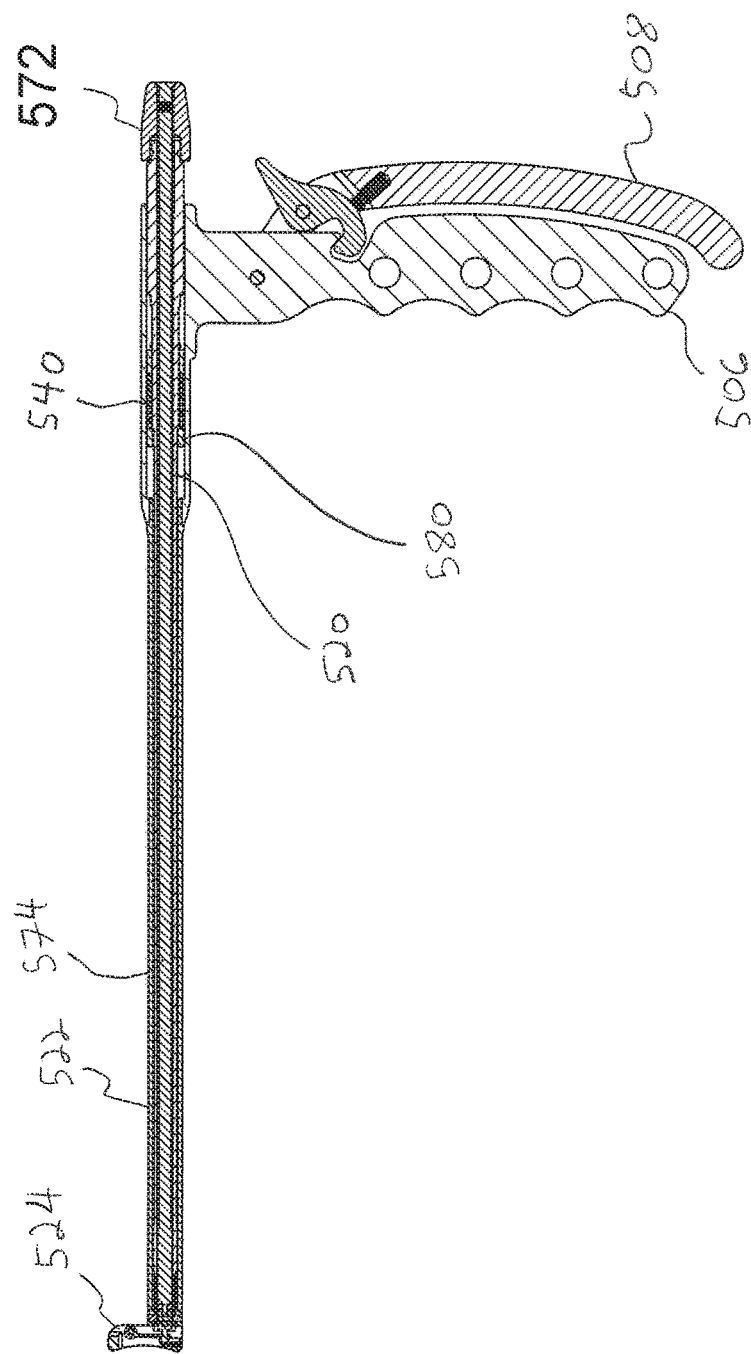
FIG. 35B is a cross-sectional view of the inserter tool taken across line 35B-35B in FIG. 32B showing the lever in the closed position and the pivot shaft shifted proximally with the bone plate removed for clarity.

With reference to FIGS. 34, 35A, and 35B, the inserter tool 500 includes a spring 540 arranged to bias the pivot sleeve 520 toward the distal end portion 502 of the inserter tool 500. Moving the lever 508 toward the handle 506 overcomes the bias force from the spring 540 and shifts the sleeve 520 back toward the proximal end portion 504. The outer body 522 includes a pair of pins 542 inserted in holes 544 of the body 522 (see FIG. 34) to support a spring support 546 within the body 522 and prevent the support 544 from traveling in direction 548. Opposite the spring support 546, there is a second spring support 550 fixed to the pivot sleeve 520 and housed within the body shaft 522 when the inserter tool 500 is assembled. Compressing the handle 508 causes the pivot sleeve 520 to move in direction 548 toward the proximal end portion 504, which moves the spring support 550 mounted on the pivot sleeve 520 in direction 548 and compresses the spring 540 between the supports 546, 550.

Releasing the handle 508 permits the spring 540 to expand and shift the pivot sleeve 520 in direction 556 back toward the distal end portion 502.

Figures 36, 37:
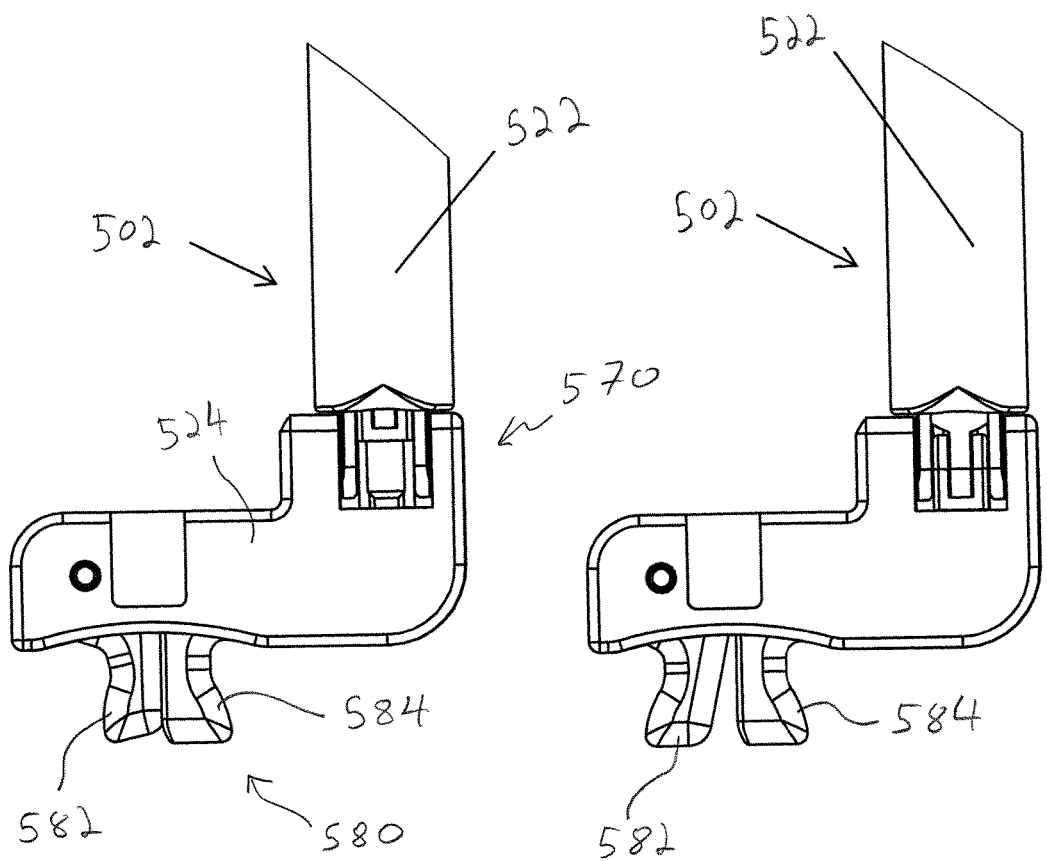
FIG. 36 is an elevational view of the distal end of the inserter tool of FIG. 29 with the bone plate removed therefrom showing a gripping portion of the inserter tool and arms of the gripping portion in a release configuration.
FIG. 37 is an elevational view similar to FIG. 36 showing the gripping portion arms in an engagement configuration.

With reference to FIGS. 35A, 36, and 37, The inserter tool 500 has a gripping device 570 that allows the inserter tool 500 to releasingly engage the bone plate 12. The gripping device 570 includes a grip control member, such as knob 572, and a gripping portion 580 that is configured to engage the bone plate 12. In one form, the gripping device 570 includes the grip control shaft 574 disposed within the pivot sleeve 520 and the knob 572 is threadingly engaged with the grip control shaft 574. Rotation of the knob 572 produces longitudinal movement of the grip control shaft 574 within the pivot shaft 520 and manipulates the configuration of the gripping portion 580.

Figure 40:
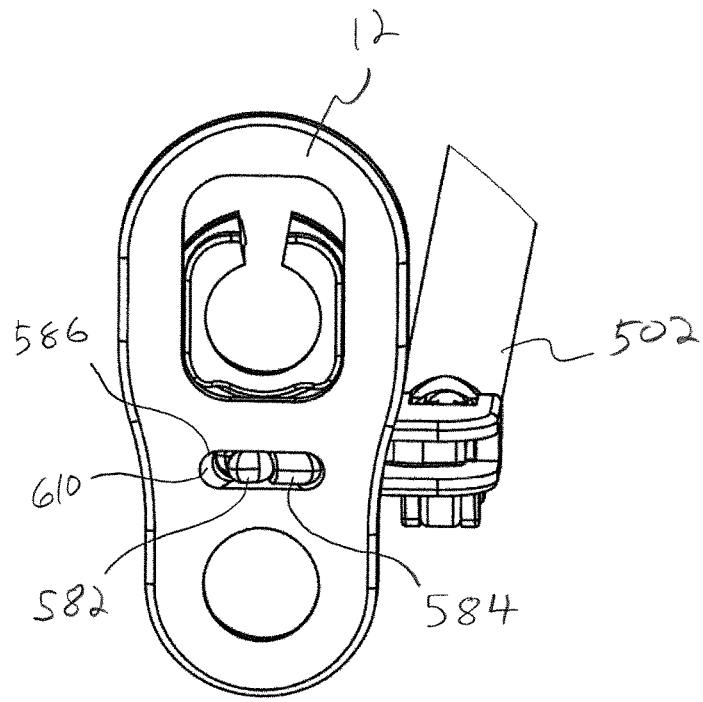
FIGS. 40 and 41 are bottom plan views of the bone plate connected to the distal end of the inserter tool showing the gripping portion arms in the release and engagement configurations.
Figure 41:
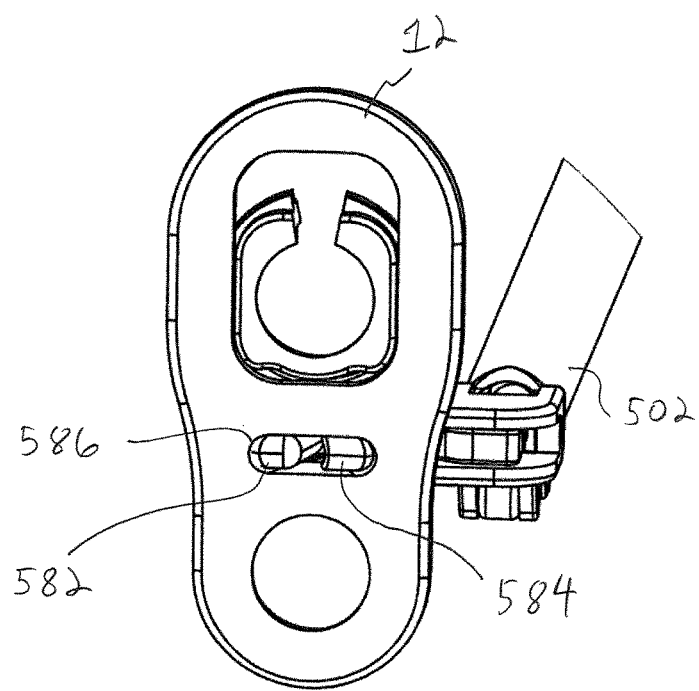

For example, the gripping portion 580 may have a plate engagement arm 582 and a fixed arm 584 sized to fit into a slot 586 of the plate member 14 (see FIGS. 11, 40, and 41). The arm 582 is operably coupled to the grip control shaft 574 by an arm linkage 590. The arm linkage 590 has one end connected to the grip control shaft 574 by a pin 592 and an opposite end connected to the arm 582 by a ball 594 and socket 596 connection, as shown in FIGS. 38 and 39.

With references to FIGS. 38 and 39, shifting the grip control shaft 574 in direction 598 toward the inserter tool proximal end portion 504 pivots the plate engagement arm 582 about a pin 600 of the pivot body 524 and brings a tip 602 of the plate engagement arm 582 toward a tip 604 of the fixed arm 584. Due to the threaded engagement between the knob 572 and the grip control shaft 574, turning the knob 572 in a clockwise direction (as viewed from behind the tool 500) would produce the movement of the grip control shaft 574 in direction 598. Conversely, turning the knob 572 counterclockwise and moving the grip control shaft 574 in direction 606 toward the inserter tool distal end portion 502 pivots the plate engagement arm 582 in an opposite direction about the pin 600 and moves the tip 602 of the plate engagement arm 582 away from the tip 604 of the plate engagement arm 584. By moving the tip 602 of the plate engagement arm 582 away from the tip 604, the arms 582, 584 can exert a compressive force against a wall 610 of the bone plate slot 586 and engage the inserter tool distal end portion 502 to the bone plate 12, shown in FIGS. 40 and 41.

Figures 42, 43:
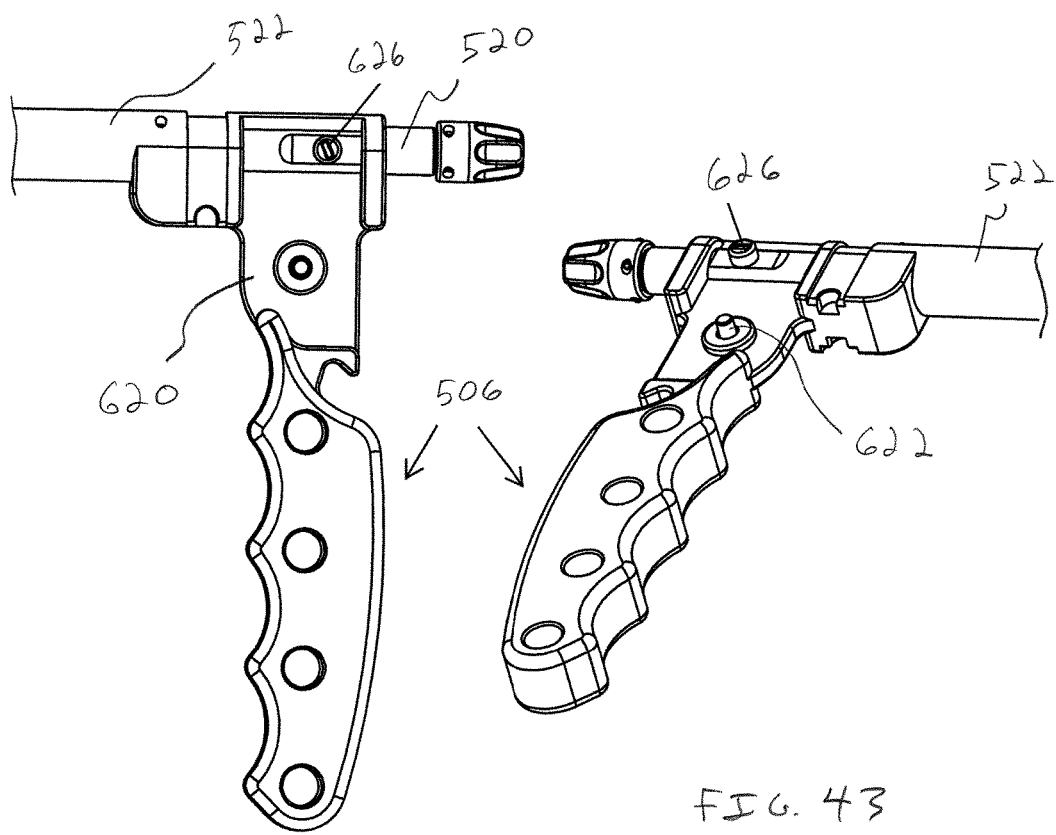
FIGS. 42 and 43 are views of the handle of the inserter tool showing an outer profile of the handle.

With reference to FIGS. 42 and 43, the handle 506 may have a recessed area 620 sized to provide clearance for the lever 508 and a lever pivot pin 622 for connecting the lever 508 to the handle 506. With the lever 508 connected to the lever pivot pin 622, a transmission end 624 of the lever 508 may be connected to a lever bolt 626 mounted on the intermediate pivot shaft 620, as shown in FIGS. 29 and 34. The transmission end 624 of the lever 508 has a slightly elongated opening 630 that is sized to permit the lever bolt 626 to travel along the opening 630. The slight elongation of the opening 630 may be desirable to accommodate the linear movement of the lever bolt 626 and the rotational, pivoting movement of the transmission end 624 of the lever 508.

The components of the inserter tool 500 may be made of various materials that preferably can be sterilized to permit cleaning of the inserter tool 500. In one form, the components are made of various metals and alloys, such as stainless steel.

Figure 44:
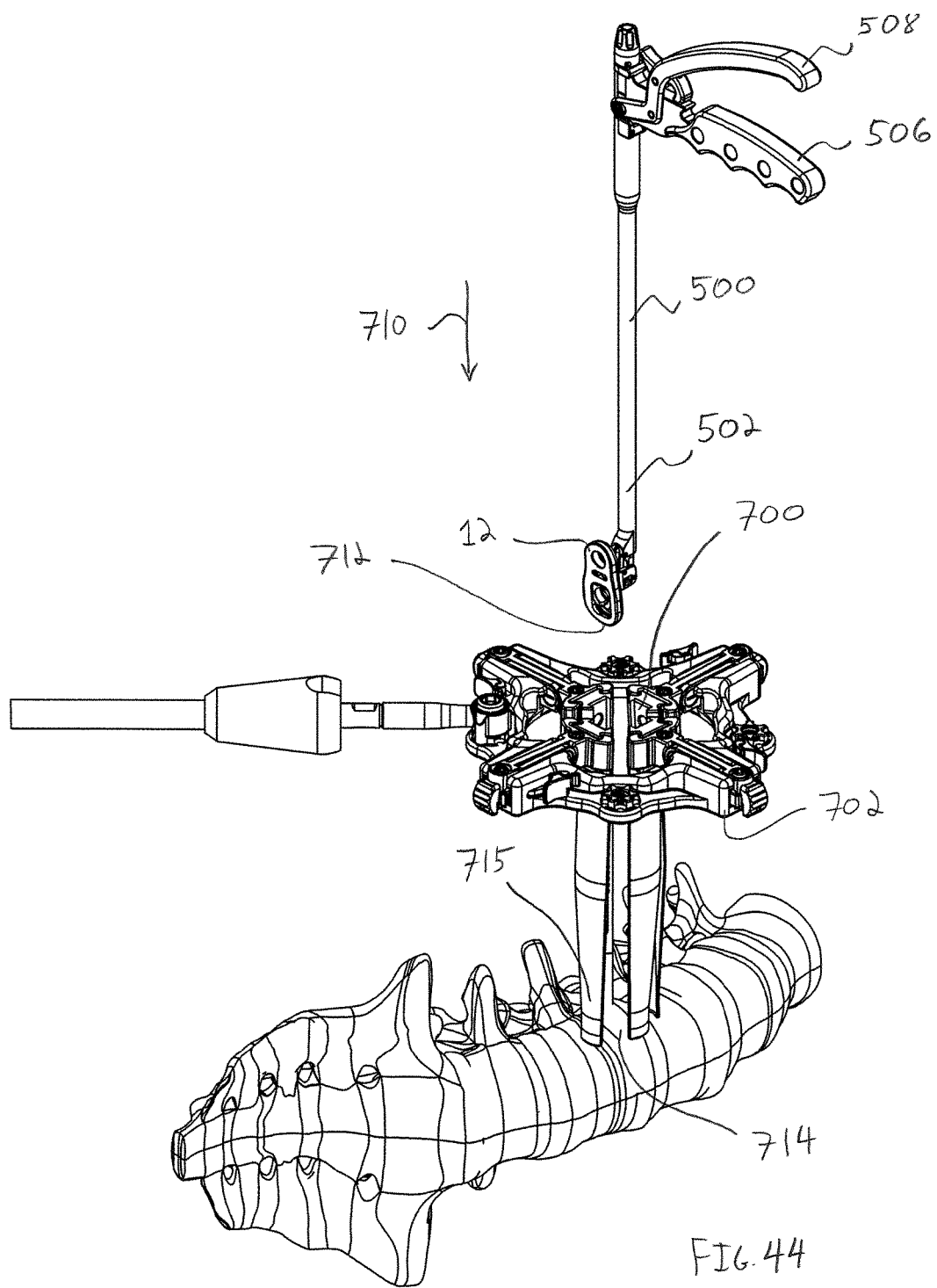
FIGS. 44-52 illustrate a method of implanting the bone plate system of FIG. 1.

With reference to FIGS. 44-52, a method of installing the bone plate system 12 including using the inserter tool 500 is shown. Initially, the distal end portion 502 of the inserter tool 500 is connected to the bone plate 12 and the implant pivot lever 508 of the inserter tool 500 is moved to the open position away from the handle 506 to orient the bone plate 12 in the insertion orientation, as shown in FIG. 44. The inserter tool 500 and connected bone plate 12 are positioned in a generally vertical orientation above a working channel 700 formed by a retractor 702. The inserter tool 500 is then moved downward in direction 710 to advance the distal end portion 502 and the bone plate 12 connected thereto into the working channel 700 until an end 712 of the bone plate 12 is adjacent a surgical site 714. In the illustrated approach, the surgical site 714 is adjacent a pair of vertebrae 720, 722 and an implant 724 therebetween (see FIG. 46).

Figure 45:
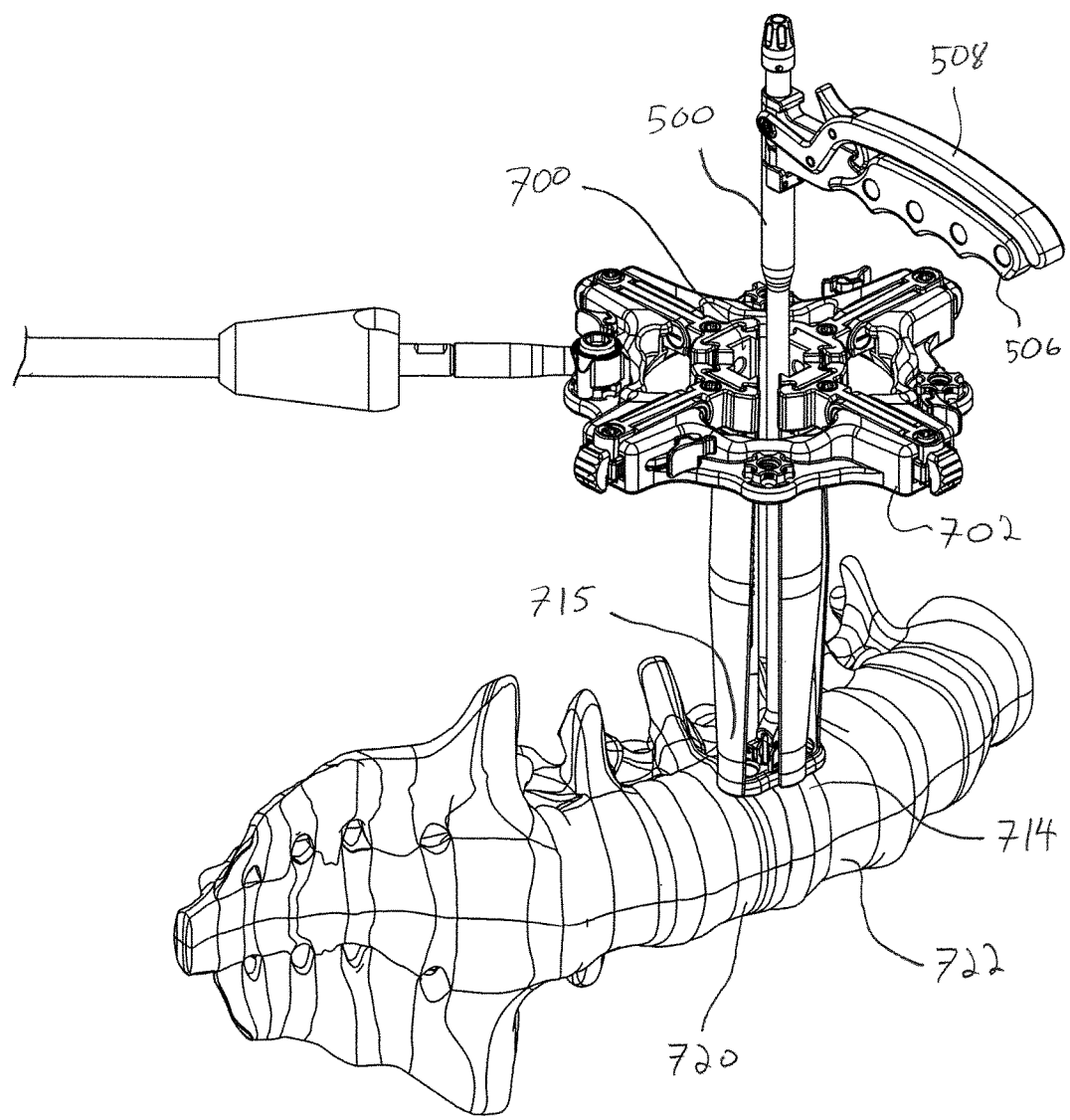
Figure 46:
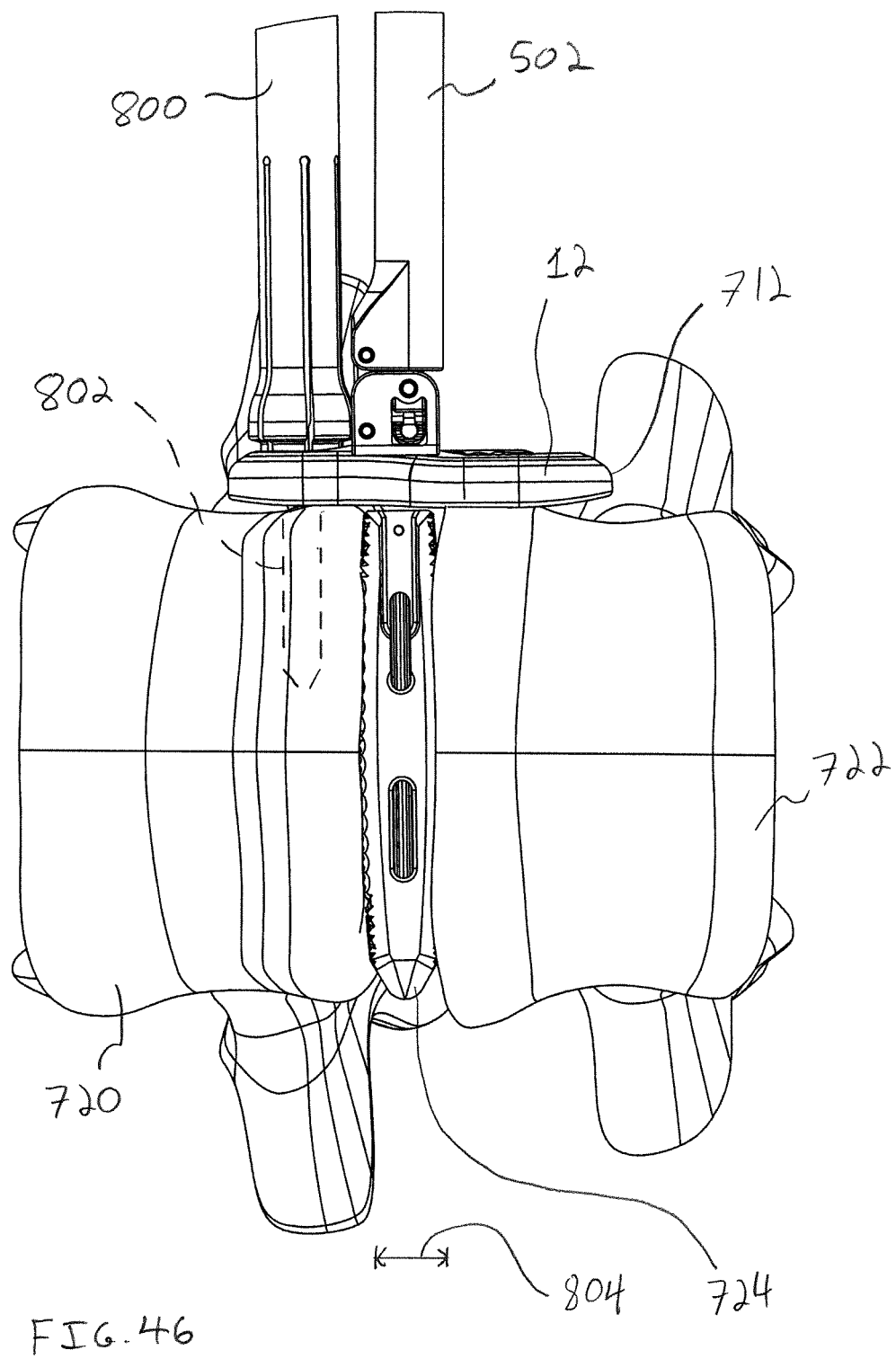

Once the end 712 of the bone plate 12 has reached the surgical site 714, the implant lever 508 is moved toward the handle 506 to pivot the bone plate 12 and move the bone plate 12 from a generally parallel orientation relative to the vertebrae 720, 722 into a generally perpendicular orientation, as shown in FIGS. 45 and 46. Further, the retractor 702 has blades with distal ends 715 that can be angled to extend generally obliquely relative to the working channel 700. This retracts the tissues adjacent the surgical site and provides room for pivoting of the bone plate 12 while maintaining a generally narrow working channel 700.

Figure 47:
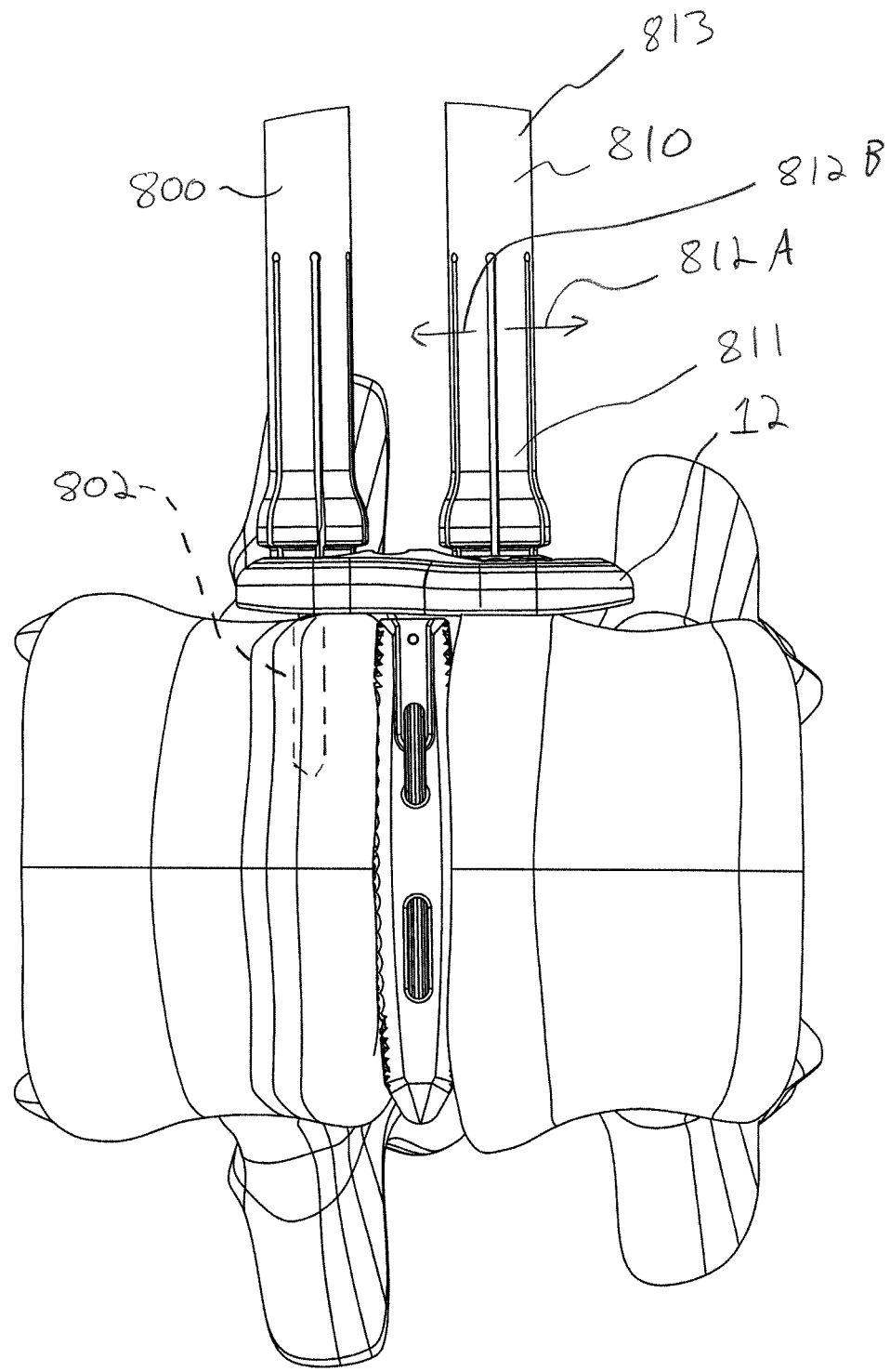

A centering sleeve 800 is then advanced through the working channel 700 and connected to the static throughbore 22 before a temporary fixation pin 802 is advanced down a cannula of the centering sleeve 800 and used to temporarily fix the bone plate 12 to the vertebrae 720. The inserter tool 500 may then be disconnected from the bone plate 12 and removed from the working channel 700. A second centering sleeve 810 is subsequently advanced through the working channel 700 to connect a distal end portion 811 of the centering sleeve 810 to the support member 16, as shown in FIG. 47. The centering sleeve 810 has a proximal portion 813 that may be manipulated by the surgeon to cause movement of the distal end portion 811 and support member 16 connected thereto. More specifically, the distal end portion 811 of the second centering sleeve 810 may be moved in direction 812A or 812B to move the support member 16 in direction 48A or 48B along axis 47 of the elongate throughbore 18 (see FIG. 11). The centering sleeve 810 preferably has a length that positions the proximal end portion 813 outside of the working channel 700 while the distal end portion 811 is connected to the support member 16 to improve the ease of manipulation of the position of the support member 16. Thus, the second centering sleeve 810 may be used to adjust the position of the support member 16 along the elongated throughbore 18 from outside of the working channel 700 and adapt the bone plate 12 to the anatomy of the patient.

For example, if the implant 724 has a relatively large thickness 804, the opening 53 of the support member 16 may not be aligned with of the vertebrae 722 when the bone plate 12 is initially pivoted to the positioning orientation shown in FIG. 46. The centering sleeve 810 can then be moved in direction 812A to move the support member 16 in direction 48A and position the support member opening 53 above the vertebrae 722.

Once the support member 16 is positioned at a desired location along the elongated throughbore 18, the second centering sleeve 810 may be removed from the working channel 700 and the drive tool 2000 connected to the bone anchor assembly 20. Connecting the driving tool 2000 to the bone anchor assembly 20 includes advancing a drive tip 2002 of the driving tool 2000 through the opening 400 of the cap drive member 34 and into engagement with the drive recess 280 (see FIGS. 18 and 26). Connecting the driving tool 2000 to the bone anchor assembly 20 may also include connecting the retention shaft 2004 of the tool 2000 with retention threads 284 of the bone screw 46, as shown in FIG. 48. The driving tool 2000, with the bone anchor assembly 20 connected thereto, can then be advanced through the working channel 700 and to advance a shank 725 of the bone screw 26 into the support member opening 53. (It is noted that vertebrae 720, 722 and implant 724 are removed from FIGS. 48-52 for clarity purposes.) The driving tool 2000 is then used to drive the bone anchor 26 into the underlying vertebrae 722, as shown in FIG. 49.

Figure 49:
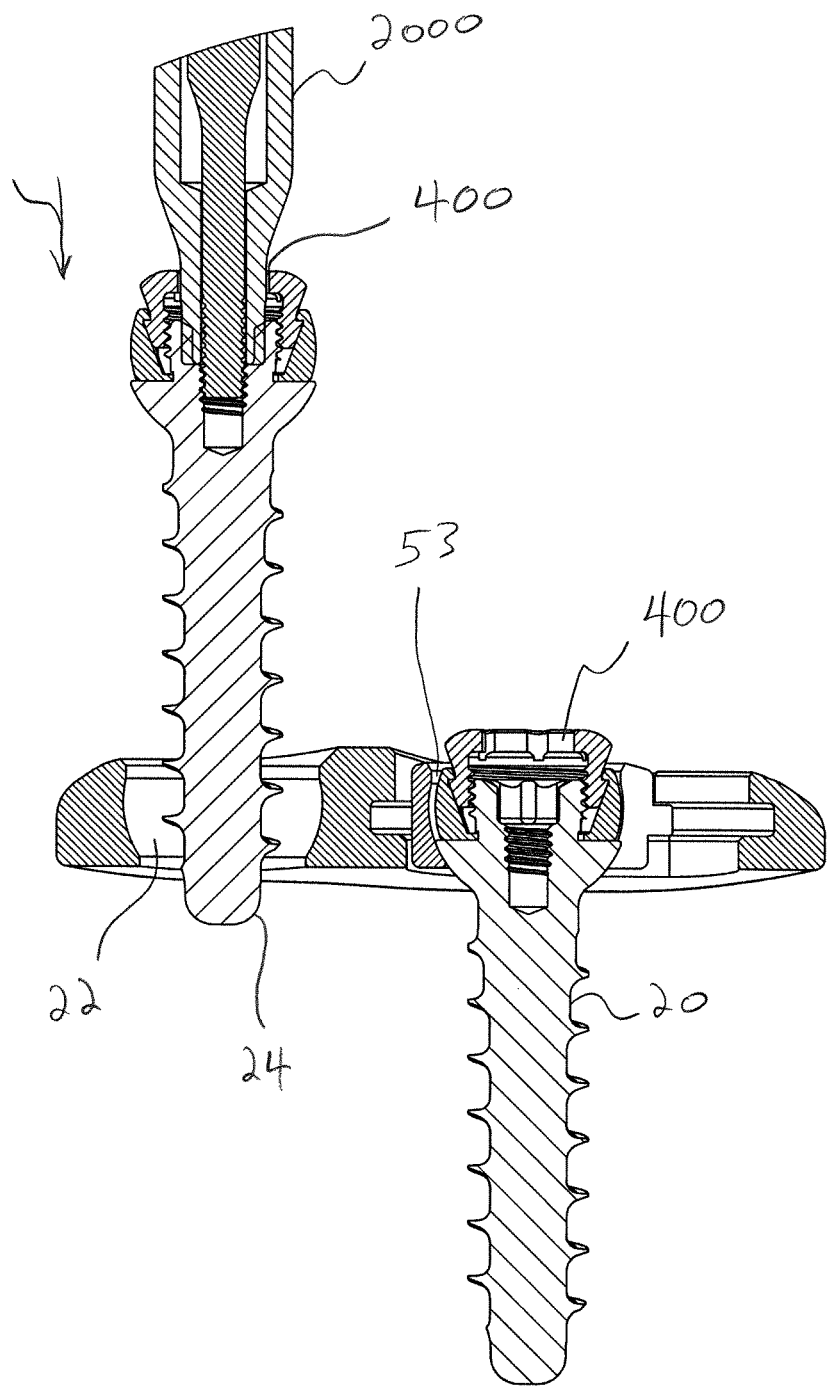
Figure 50:
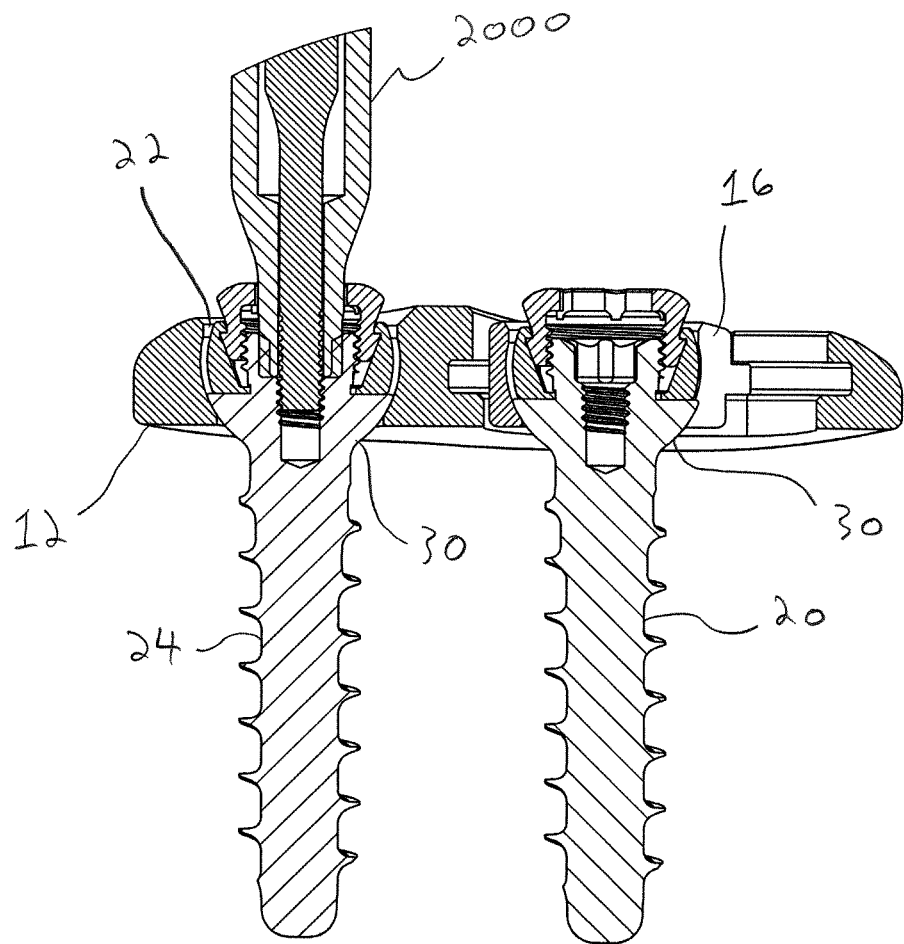

Next, the drive tool 2000 is used to drive the bone anchor assembly 24 into the fixed throughbore 22 using a similar approach taken with respect to bone anchor 20, as shown in FIGS. 49 and 50. With the bone screws 26 of the bone anchor assemblies 20, 24 holding the bone plate 12 against the vertebrae 720, 722, a final tightener 3002 is advanced into the opening 400 of the cap drive member 34 of the bone anchor assembly 24 (see FIG. 26) and turned in direction 737 to shift the cap drive member 34 to the locked position. Turning of the final tightener 3002 and the resulting movement of the cap drive member 34 toward its locked position causes the cap drive member 34 to expand the locking cap 36. This tightly engages the locking cap 36 with the seating surface 120 of the throughbore 22.

The locking tool 3000 is then advanced into the opening 400 of the cap drive member 34 of the bone anchor assembly 20 and turned to move the cap drive member 34 toward the locked position. This expands the locking cap 36 of the bone anchor assembly 20 and tightly engages the locking cap 36 with the seating surface 103 of the support member 16. This shifts the portions 70, 72 of the support member 16 apart in directions 76, 78 against the throughbore walls 80, 82 (see FIG. 7) and thereby fixes the position of the support member 16 along the elongated throughbore 18. Further, because the cap drive member 34 is threadingly engaged with the bone screw head 30, shifting the cap drive member 34 to the locked position tightly engages the cap drive member 34 to the head 30 as well as the locking cap 36 therebetween. In this manner, the bone anchor assembly 20 is firmly engaged with the support member 16 which is in turn firmly engaged to the plate member 14 at the desired location along the throughbore 18.

Figure 54:
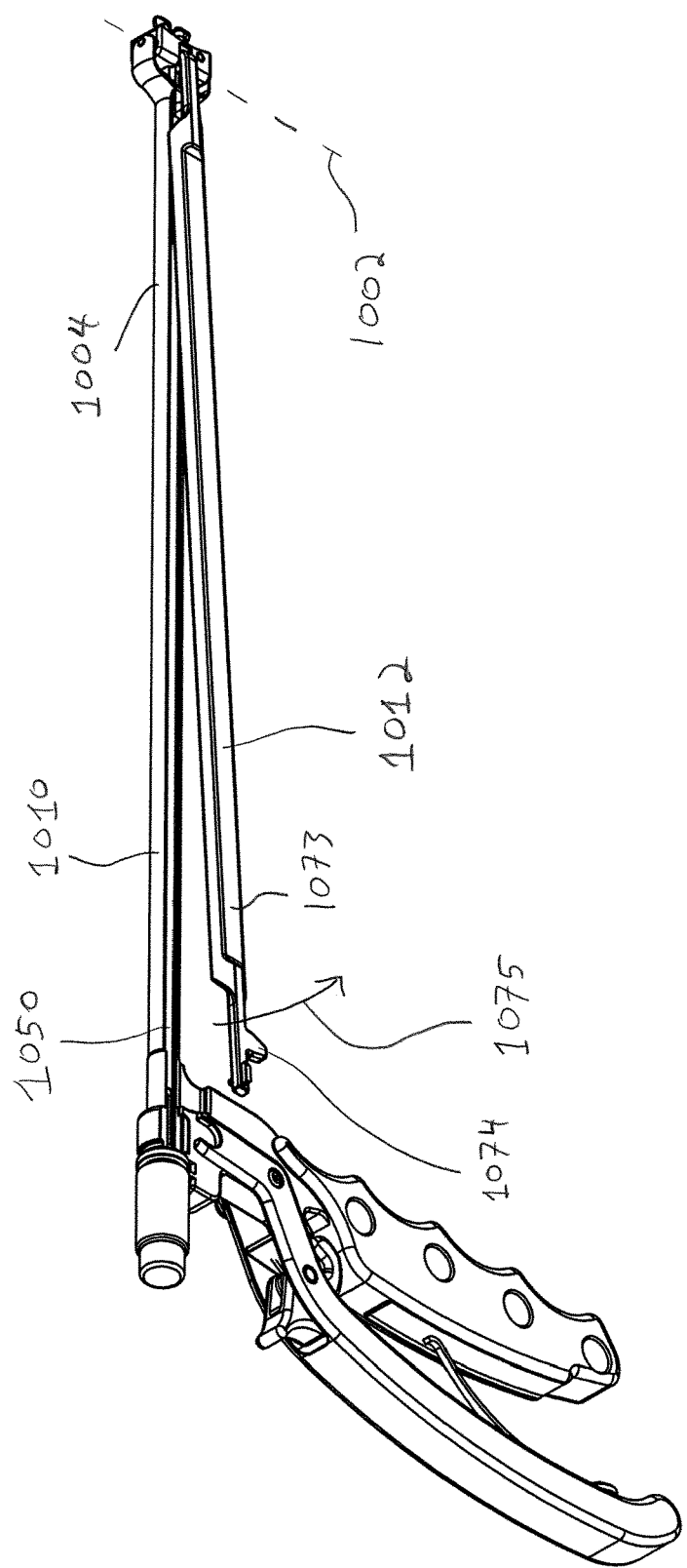
FIG. 54 is right side perspective view of the inserter tool of FIG. 53 showing the inserter tool partially disassembled including a pivot sleeve of the inserter tool disconnected from a lever of the tool and pivoted away from a shaft of the inserter tool.

With respect to FIGS. 53-61, an inserter tool 1000 is provided for positioning the bone plate 12 near one or more bones. The inserter tool 1000 is substantially similar to the inserter tool 500 described above such that the differences between the inserter tools 500, 1000 will be highlighted. One difference between the inserter tools 500, 1000 is that the inserter tool 1000 has components that can be partially disassembled and pivoted generally about an axis 1002 at a distal end 1004 of the inserter tool 1000, as shown in FIG. 54. The ability to partially disassemble and pivot the components of the inserter tool 1000 allows the inserter tool 1000 to be cleaned without complete disassembly of the tool 1000.

More specifically, the inserter tool 1000 has an outer body shaft 1010 and a partial pivot sleeve 1012 for controlling pivoting of a pivot body 1014. The distal end of the pivot sleeve 1012 is connected to the pivot body 1014 at a pin 1030 so that translational movement of the pivot sleeve 1012 produces pivoting of the pivot body 1014. The inserter tool 1000 has a lever 1016 connected to the pivot sleeve 1012 for controlling pivoting of a pivot body 1014 at the distal end 1004 of the inserter tool 1000. Moving the pivot lever 1016 toward a handle 1018 of the inserter tool 1000 shifts the pivot sleeve 1012 in direction 1020 toward a proximal end 1019 of the inserter tool 1000 and pivots the pivot body 1014 about a pin 1022. A spring 1019 may bias the handle 1018 toward an open position to limit unintentional pivoting of the pivot body 1014 and bone plate 12 connected thereto.

Figure 55:
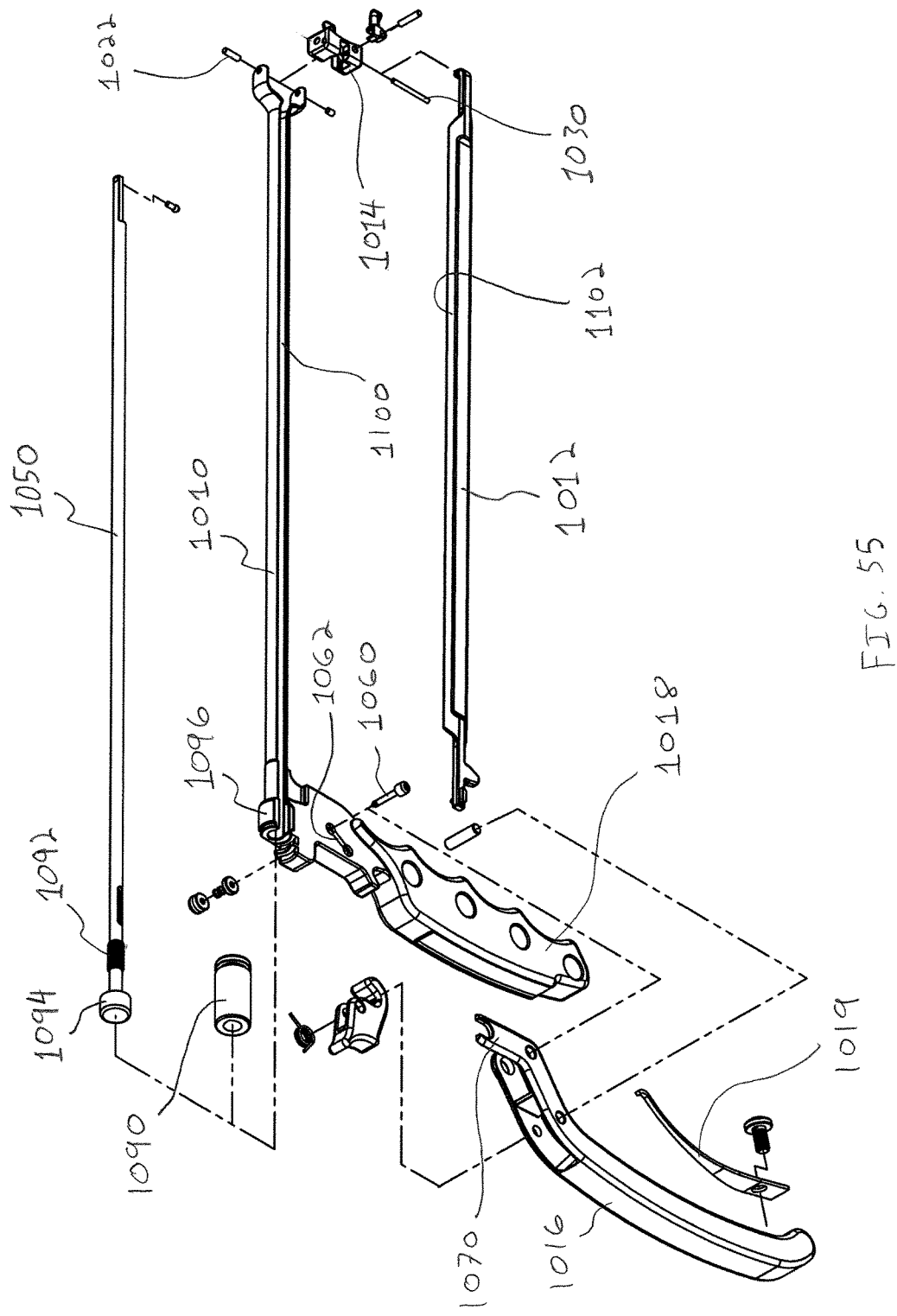
FIG. 55 is an exploded schematic view of the inserter tool of FIG. 53 showing a body shaft, the pivot sleeve, and a pivot control shaft of the inserter tool.
Figure 56:
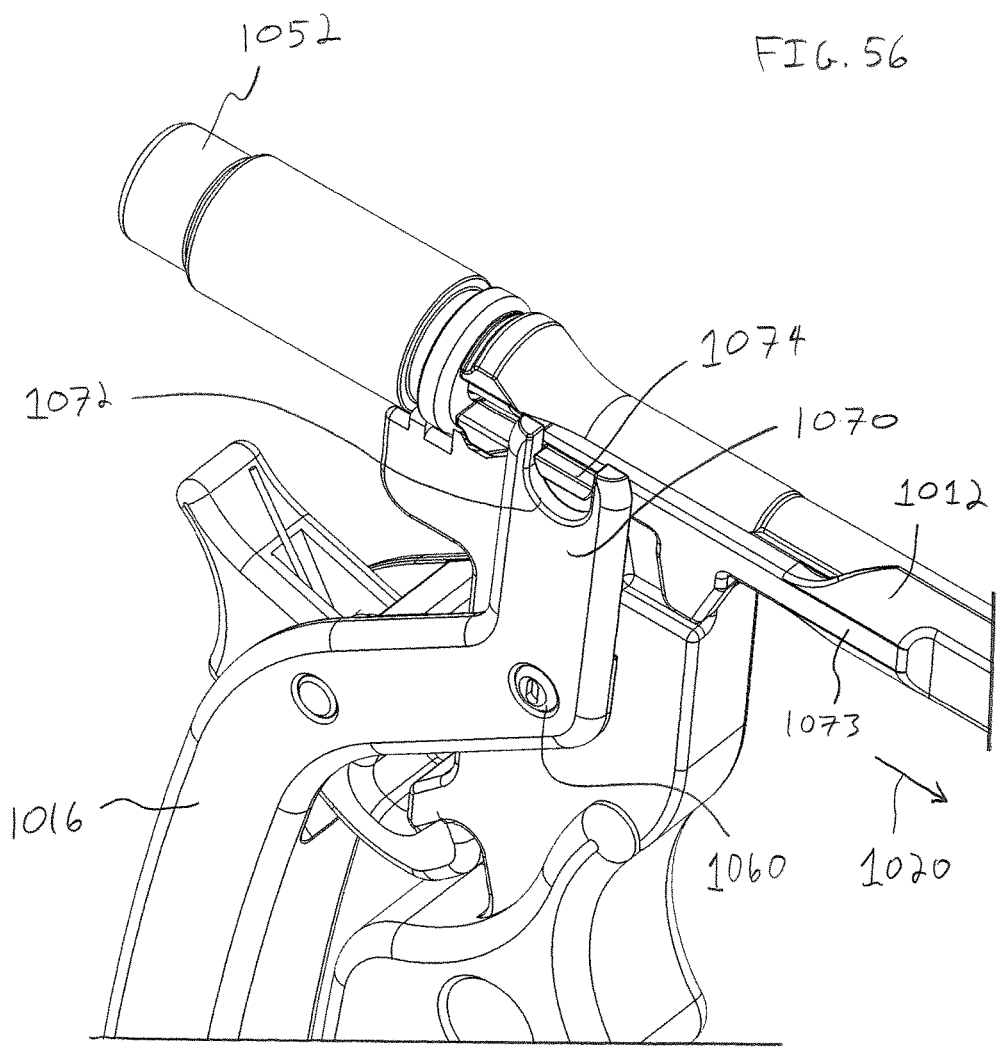
FIG. 56 is an enlarged right side perspective view of the inserter tool of FIG. 53 showing the pivot sleeve connected to the lever.
Figure 57:
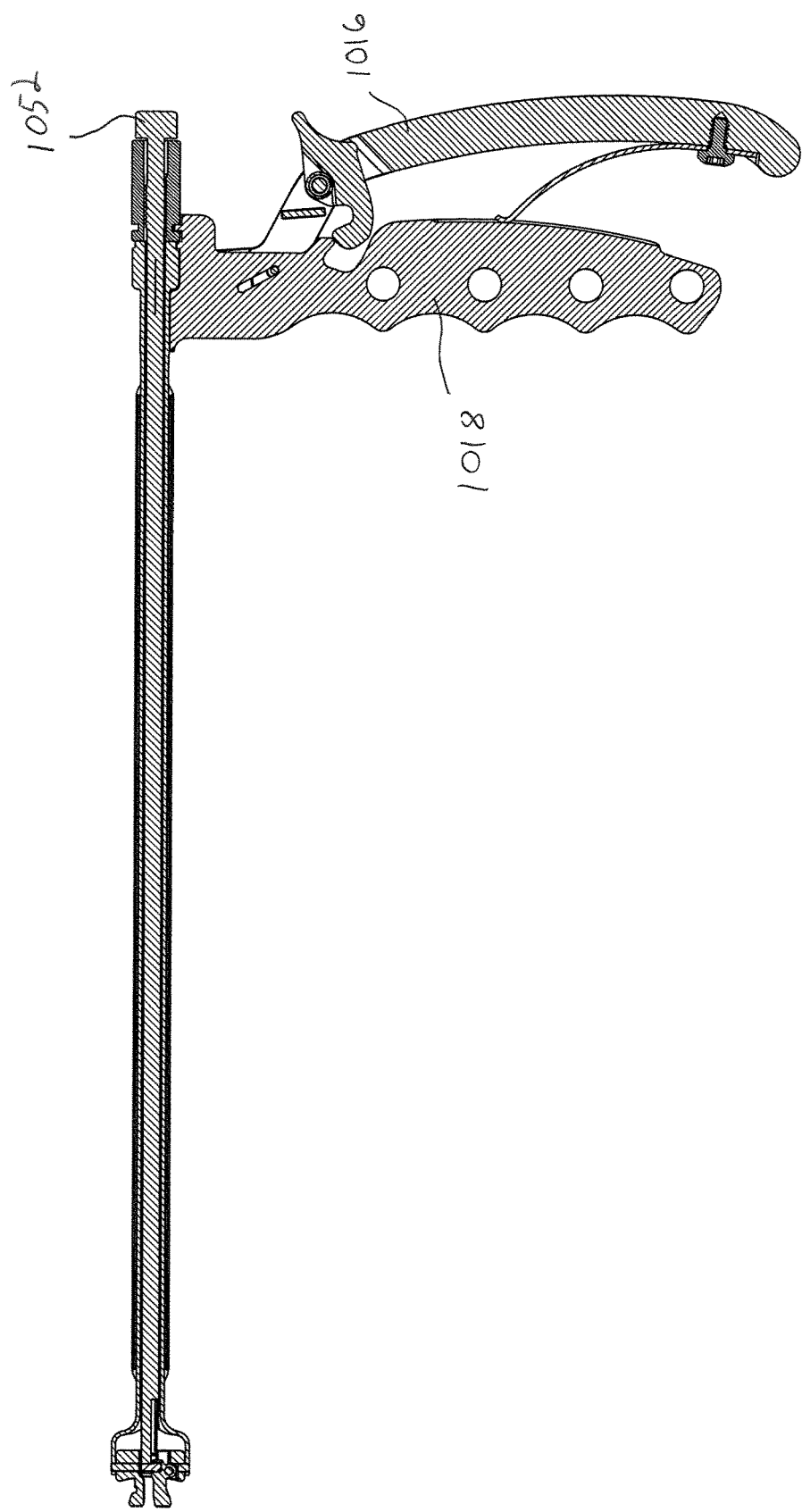
FIG. 57 is a cross-sectional view of the inserter tool of FIG. 53 showing a lever of the inserter tool in an open position.
Figure 58:
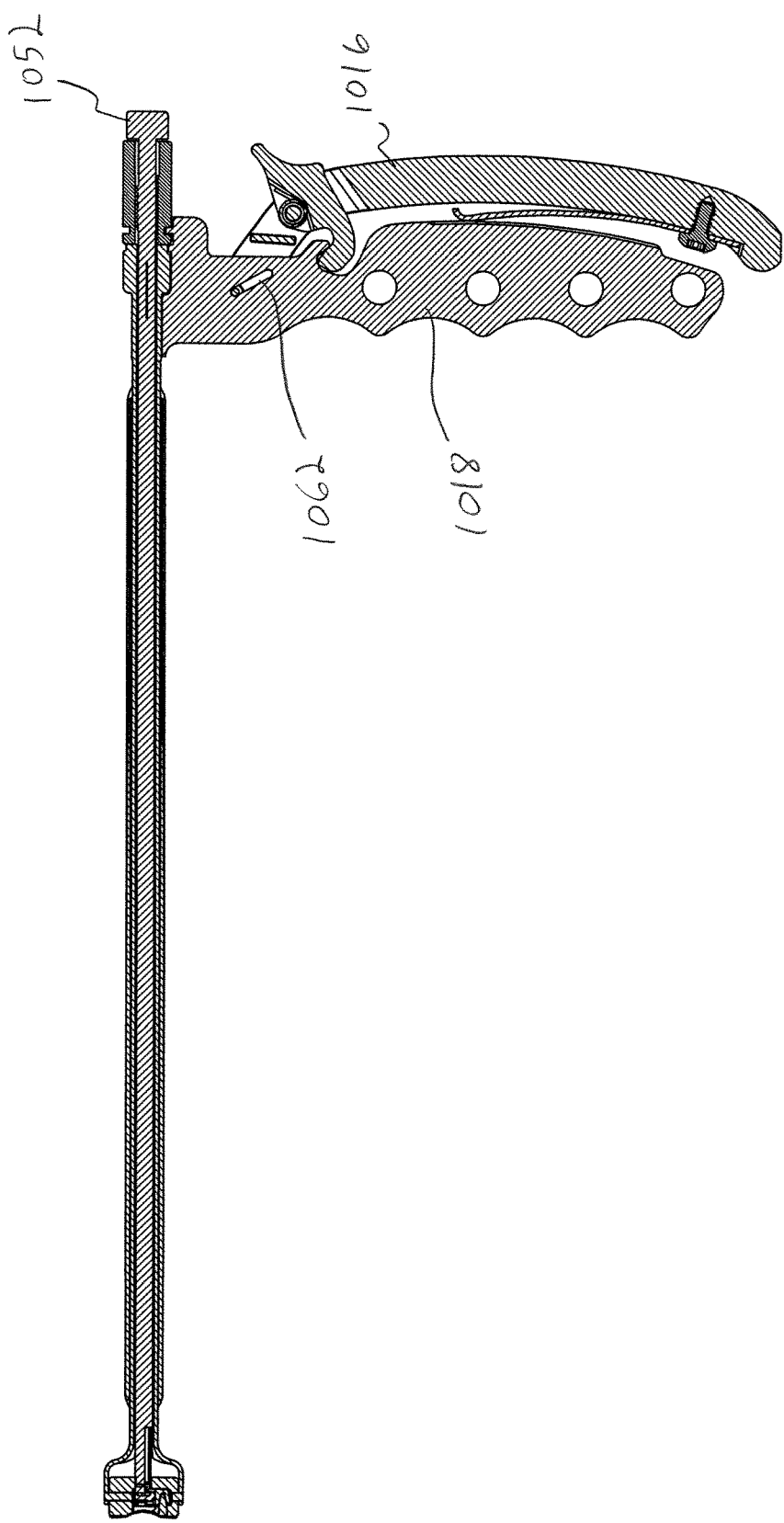
FIG. 58 is a cross-sectional view similar to FIG. 57 showing the lever in a closed position.
Figure 59:
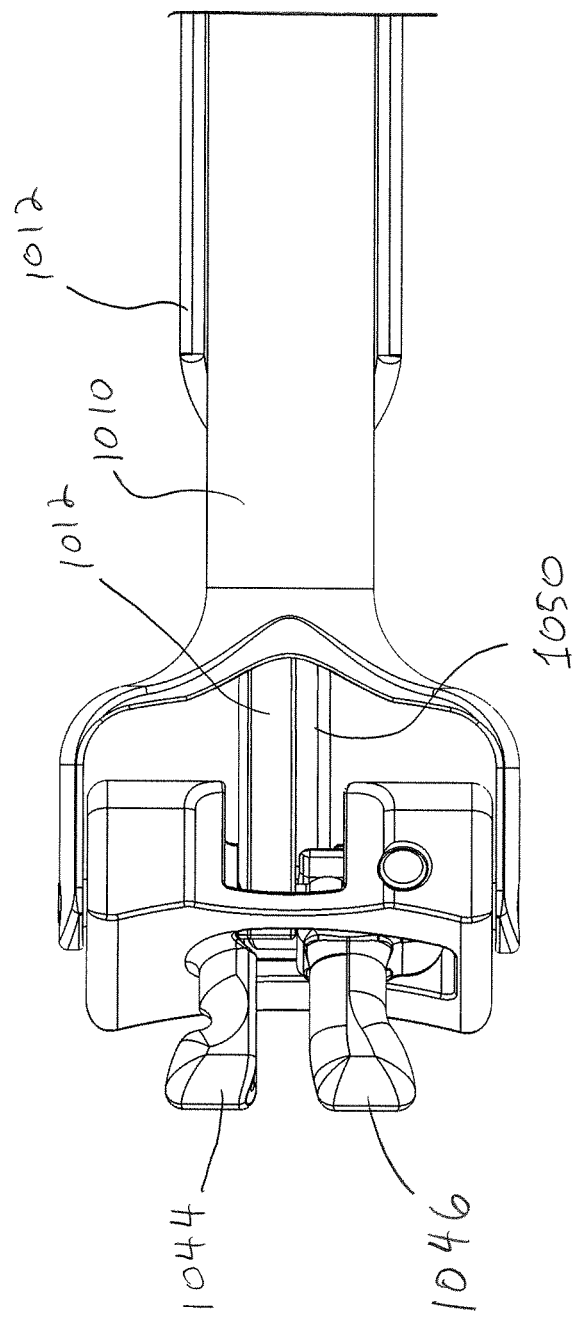
FIGS. 59 and 60 are enlarged, elevational views of different sides of the inserter tool of FIG. 53 showing arms of the body shaft which support a pivot body of the distal end of the inserter tool.
Figure 60:
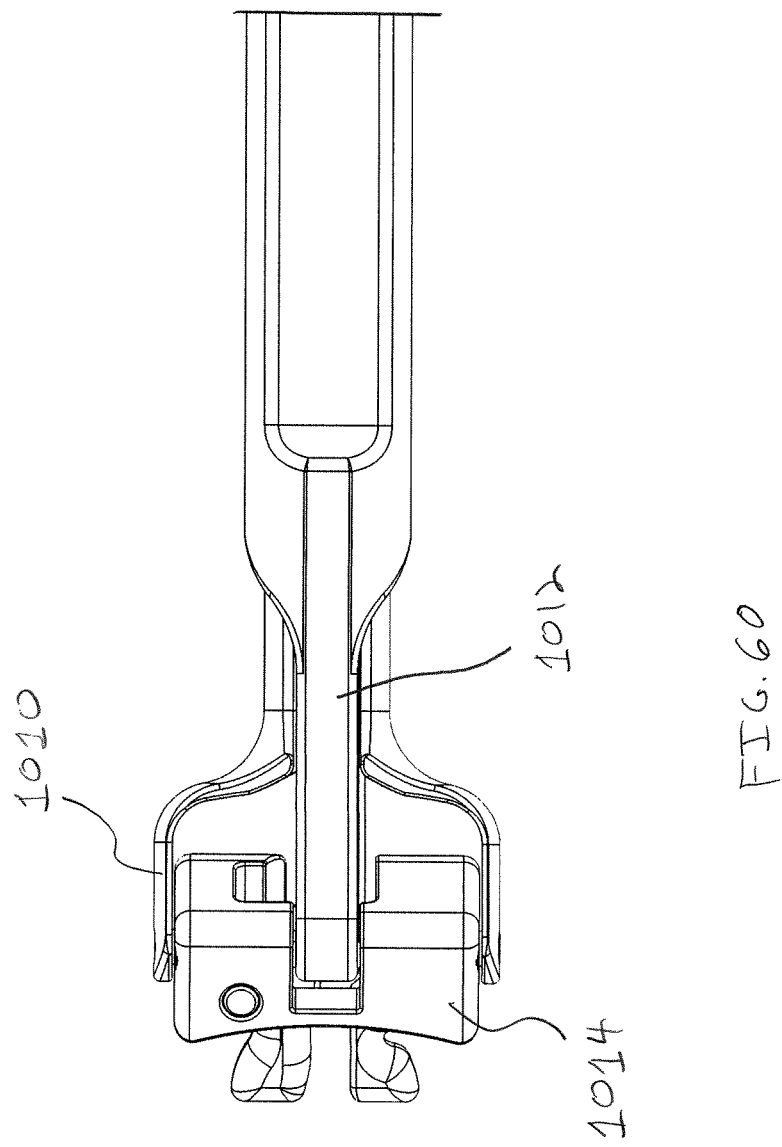
Figure 61:
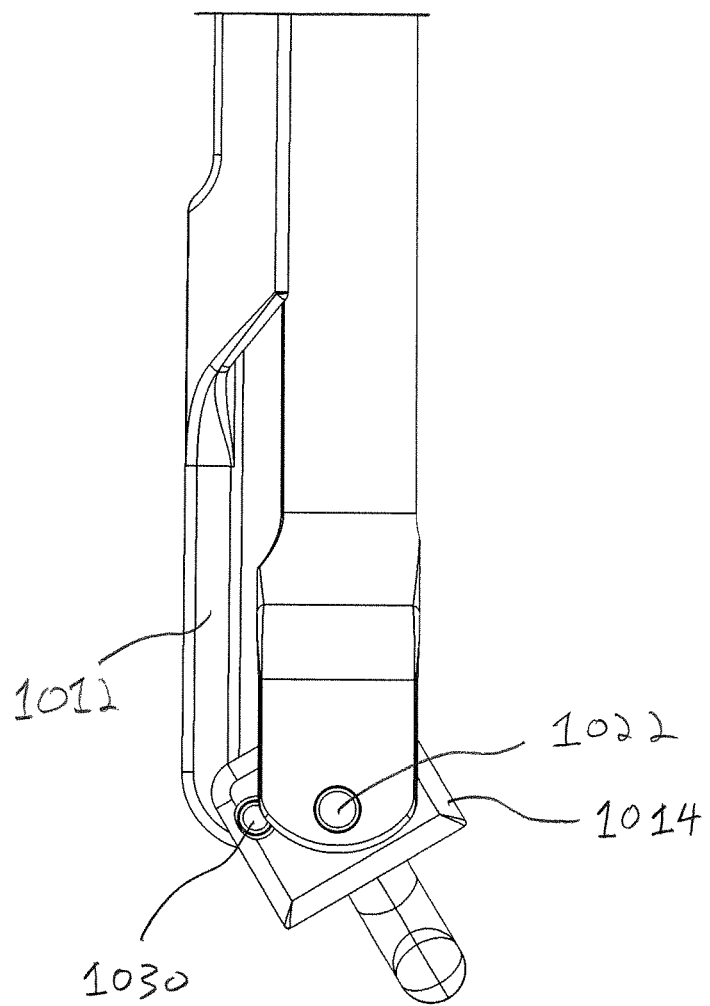
FIG. 61 is an enlarged plan view of the distal end of the inserter showing the pivot body pivoted relative to the body shaft.

The lever 1016 is connected to the handle 1018 by a pin 1060 received within a slot 1062 of the handle 1018 (see FIGS. 55, 57). The lever 1016 has a transmission end 1070 with a recess 1072 sized to receive a tab 1074 of the pivot sleeve 1012, as shown in FIG. 56. The tab 1074 of the pivot sleeve 1012 rides in the recess 1072 during back and forth movement of the pivot sleeve 1012. During disassembly of the inserter tool 1000, the lever 1016 can be shifted in direction 1064 (see FIG. 53) to disengage the transmission end 1070 of the lever 1016 from the tab 1074 of the pivot sleeve 1012. With the lever transmission end 1070 disengaged from the pivot sleeve 1012, a proximal end 1073 of the pivot sleeve 1012 can be pivoted in direction 1075 away from the pivot body 1014, as shown in FIG. 54. Pivoting the pivot sleeve 1012 in direction 1075 moves the pivot sleeve 1012 about the pin 1030 which connects the pivot sleeve 1012 to the pivot body 1014.

Another difference between the inserter tools 500, 1000 is that the inserter tool 1000 has a grip control shaft 1050 and a grip adjustment member 1090 engaged with threads 1092 of the grip control shaft 1050. The grip adjustment member 1090 is captured by the threads 1092 between an enlarged knob 1094 of the grip control shaft 1050 and a collar 1096 of the body shaft 1010. The grip adjustment member 1090 is turned clockwise or counterclockwise to produce proximal or distal longitudinal movement of the grip control shaft 1050 by way of the engagement between internal threads of the grip adjustment member 1090 and the threads 1092 on the grip control shaft 1050.

During disassembly, the knob 1094 is turned ninety degrees clockwise to rotate a foot 1095 of the grip control shaft 1050 into a recess 1097 of the pivot body 1014 (see FIGS. 55 and 57). The grip adjustment member 1090 is then turned to produce longitudinal movement of the grip control shaft 1050 toward the proximal end of the inserter tool 1000 until the threads 1092 of the grip control shaft 1050 disengage the internal threads of the grip adjustment member 1090. Next, the knob 1094 is grasped and pulled in direction 1099 (see FIG. 54) to withdraw the grip control shaft 1050 from within the outer body shaft 1010. At this point, the pivot sleeve 1012 is pivoted away from the outer body shaft 1010 and the grip control shaft 1050 has been withdrawn from the outer body shaft 101. Because both the pivot sleeve 1012 and grip control shaft 1050 are separated from the body shaft 1010, the surfaces of the body shaft 1010, pivot sleeve 1012, and grip control shaft 1050 may be easily accessed and cleaned. Further, as shown in FIG. 55, the body shaft 1010 has a generally C-shaped cross section with an opening 1100 along one side thereof and the pivot shaft 1012 has a generally U-shaped cross section with an opening 1102 along one side thereof. The cross sections of the body shaft 1010 and the pivot shaft 1012 provide ready access to the internal surfaces of the body shaft 1010 and the pivot shaft 1012 so that the internal surfaces may be easily cleaned.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A method of implanting a bone plate in a patient, the method comprising:
advancing distal, spaced-apart gripping members of an inserter tool into an opening of the bone plate, each of the gripping members including a proximal portion and a distal portion, the gripping members including a pivotal gripping member that is pivotal relative to a pivot body of the inserter tool and a fixed gripping member that is fixed relative to the pivot body, the proximal portion of the pivotal gripping member being pivotally coupled to the pivot body by a pivot pin and supported thereon and the proximal portion of the fixed gripping member being fixedly coupled to the pivot body and supported thereon;

shifting a grip control shaft of the inserter tool coupled to the pivot body in a first direction along a longitudinal axis of an elongated shaft of the inserter tool to pivot the pivotal gripping member relative to the pivot body of the inserter tool and away from the fixed gripping member to grip the bone plate with the distal portions of the gripping members and connect the bone plate to the pivot body of the inserter tool in a first orientation relative to the inserter tool;

advancing the bone plate in the first orientation through a surgical channel formed in tissue toward at least one bone of the patient;

pivoting a gripping portion of a proximal pivot lever of the inserter tool, the pivot lever being pivotally connected to a fixed distal handle of the inserter tool and pivotal about a first pivot axis defined by the connection between the pivot lever and the fixed distal handle, the pivot lever being connected to the pivot body by an elongated pivot member, the pivot body being pivotally connected to the elongated shaft of the inserter tool and pivotal about a second pivot axis defined by the connection between the pivot body and the elongated shaft of the inserter tool;

wherein pivoting the gripping portion includes pivoting the gripping portion distally toward the fixed distal handle of the inserter tool about the first pivot axis extending perpendicular to the longitudinal axis of the elongated shaft of the inserter tool which causes the pivot body, the pivotal gripping member, and the fixed gripping member to pivot together about the second pivot axis extending perpendicular to the longitudinal axis of the elongated shaft of the inserter tool and pivots the bone plate connected to the pivot body from the first orientation to a second orientation relative to the inserter tool, the second orientation being different than the first orientation;

positioning the bone plate in the second orientation in contact with the at least one bone;

securing the bone plate to the at least one bone, wherein securing the bone plate to the at least one bone includes driving a shank of at least one bone anchor through at least one opening of the bone plate and into the at least one bone; and shifting the grip control shaft of the inserter tool in a second direction opposite to the first direction along the longitudinal axis to pivot the pivotal gripping member relative to the pivot body and toward the fixed gripping member to release the gripping members and disconnect the pivot body of the inserter tool from the bone plate secured to the at least one bone.

2. The method of claim 1, wherein the bone plate is elongated and connecting the bone plate to the pivot body of the inserter tool in the first orientation includes connecting the bone plate to the pivot body of the inserter tool so that a longitudinal axis of the bone plate extends substantially parallel to the longitudinal axis of the inserter tool shaft.

3. The method of claim 2, wherein pivoting the gripping portion of the proximal pivot lever to pivot the bone plate to the second orientation relative to the inserter tool includes pivoting the bone plate so that the longitudinal axis of the bone plate extends substantially perpendicular to the longitudinal axis of the inserter tool shaft.

4. The method of claim 1, wherein pivoting the gripping portion of the proximal pivot lever to pivot the bone plate to the second orientation includes pivoting the bone plate from the first orientation wherein the bone plate is substantially parallel to the shaft of the inserter tool to the second orientation wherein the bone plate is transverse to the inserter tool shaft.

5. The method of claim 1, wherein the at least one bone includes a pair of vertebrae and the method further includes inserting an implant through the surgical channel and into an intervertebral space between the vertebrae.

6. The method of claim 1, wherein
pivoting the gripping portion of the proximal pivot lever to pivot the bone plate to the second orientation relative to the inserter tool includes pivoting the gripping portion of the proximal pivot lever outside of the surgical channel.

7. The method of claim 1, wherein shifting the grip control shaft in the first direction along the longitudinal axis includes turning a knob of the inserter tool.

8. The method of claim 1, wherein the at least one bone includes first and second bones and driving the shank of the at least one bone anchor includes driving a shank of a first bone anchor through a first opening of the bone plate and into the first bone and driving a shank of a second bone anchor through a second opening of the bone plate and into the second bone to secure the bone plate to the first and second bones.

9. The method of claim 1, further comprising locking the bone plate in the second orientation relative to the inserter tool.

10. The method of claim 1, further comprising retracting the tissue using a plurality of blades of a retractor to form the surgical channel.

11. The method of claim 10, further comprising pivoting distal ends of the blades apart to retract the tissue adjacent the at least one bone.

12. The method of claim 10, wherein advancing the bone plate through the surgical channel toward the at least one bone includes advancing the bone plate through the channel while the bone plate extends substantially parallel to the blades of the retractor.

13. The method of claim 10, wherein pivoting the gripping portion of the proximal pivot lever to pivot the bone plate to the second orientation relative to the inserter tool includes pivoting the bone plate to extend generally perpendicular to the blades of the retractor.

14. The method of claim 1, wherein securing the bone plate to the at least one bone includes:
advancing a pin through an opening of the bone plate and into engagement with a first bone; and
advancing a bone anchor through another opening of the bone plate and into engagement with a second bone.

15. The method of claim 1, further comprising moving a resilient support member along an elongated throughbore of the bone plate and securing the bone plate to the at least one bone includes advancing a shank of a bone anchor into a through opening of the support member and into the at least one bone.

16. The method of claim 1, wherein pivoting the gripping portion of the proximal pivot lever includes pivoting the gripping portion of the lever distally and pivoting a transmission portion of the proximal pivot lever on an opposite side of the pivot connection proximally about the pivot connection with the fixed distal handle to shift proximally the elongated pivot member of the inserter tool connecting the transmission portion and the pivot body.

17. The method of claim 16, wherein shifting proximally the elongated pivot member of the inserter tool causes pivoting of the pivot body of the inserter tool which supports the bone plate.

18. The method of claim 1, wherein pivoting the gripping portion of the proximal pivot lever distally toward the fixed distal handle of the inserter tool includes loading a spring disposed between the gripping portion of the proximal pivot lever and the fixed distal handle.

19. The method of claim 1, wherein securing the bone plate to the at least one bone further includes:
   advancing a shank of a bone anchor assembly into an opening of a resilient support member that is disposed in an elongated throughbore of the bone plate and into the at least one bone;
   seating a head portion of the bone anchor assembly in the opening of the resilient support member; and
   driving a locking member of the seated head portion of the bone anchor between unlocked and locked positions to radially expand the resilient support member and engage portions of the resilient support member and the bone plate which fixes the resilient support member along the elongated throughbore relative to the bone plate.

20. The method of claim 19, wherein driving the locking member of the seated head portion of the bone anchor between unlocked and locked positions includes driving the locking member along the bone anchor and radially expanding a locking cap of the bone anchor assembly to radially expand the resilient support member.

21. The method of claim 19, wherein advancing the shank of the bone anchor assembly into the opening of the resilient support member includes connecting the bone anchor to a first tool and advancing the bone anchor using the first tool; and
   driving the locking member of the seated head portion includes driving the locking member using a second tool.

* * * * *